United States Patent
Wang et al.

(10) Patent No.: US 10,961,222 B2
(45) Date of Patent: Mar. 30, 2021

(54) CHEMICAL COMPOUND OF ISOCITRATE DEHYDROGENASE INHIBITOR, AND APPLICATION THEREOF

(71) Applicant: NANJING SANHOME PHARMACEUTICAL CO., LTD., Nanjing, Jiangsu (CN)

(72) Inventors: Yong Wang, Nanjing (CN); Liwen Zhao, Nanjing (CN); Xiaorong Liu, Nanjing (CN); Yan Zhang, Nanjing (CN); Dandan Huang, Nanjing (CN); Chunhuan Jiang, Nanjing (CN); Xinsheng Shi, Nanjing (CN); Hongfeng Gu, Nanjing (CN); Silin Pang, Nanjing (CN); Wei Hai, Nanjing (CN); Bingyang Ge, Nanjing (CN)

(73) Assignee: NANJING SANHOME PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 16/312,666

(22) PCT Filed: Jul. 20, 2017

(86) PCT No.: PCT/CN2017/093597
§ 371 (c)(1),
(2) Date: Dec. 21, 2018

(87) PCT Pub. No.: WO2018/014852
PCT Pub. Date: Jan. 25, 2018

(65) Prior Publication Data
US 2019/0161473 A1    May 30, 2019

(30) Foreign Application Priority Data
Jul. 21, 2016    (CN) .......................... 201610580910.0

(51) Int. Cl.
| | |
|---|---|
| *C07D 401/14* | (2006.01) |
| *C07D 417/14* | (2006.01) |
| *A61P 35/00* | (2006.01) |
| *A61K 31/53* | (2006.01) |
| *A61K 31/444* | (2006.01) |

(52) U.S. Cl.
CPC .......... *C07D 401/14* (2013.01); *A61K 31/444* (2013.01); *A61K 31/53* (2013.01); *A61P 35/00* (2018.01); *C07D 417/14* (2013.01)

(58) Field of Classification Search
CPC ..................................................... C07D 401/14
USPC ......................................................... 514/210.2
See application file for complete search history.

(56) References Cited

FOREIGN PATENT DOCUMENTS

| | | |
|---|---|---|
| EP | 3330258 | 6/1918 |
| WO | WO 2016/177347 | 11/1916 |
| WO | WO 2017/016513 | 2/1917 |
| WO | WO 2013/102431 | 7/2013 |
| WO | WO-2013102431 A1 * | 7/2013 |
| WO | WO 2015/003360 | 1/2015 |
| WO | WO 2015/003640 | 1/2015 |
| WO | WO 2015/006592 | 1/2015 |
| WO | WO-2016177347 A1 * | 11/2016 ........... C07D 401/14 |

OTHER PUBLICATIONS

English translation of PCT International Search Report issued in International Application No. PCT/CN2017/093597, dated Sep. 20, 2017.

\* cited by examiner

*Primary Examiner* — Kahsay Habte
(74) *Attorney, Agent, or Firm* — Parker Highlander PLLC

(57) ABSTRACT

Provided are a chemical compound of an isocitrate dehydrogenase inhibitor, and an application thereof, belonging to the field of medicinal chemistry; specifically provided is the chemical compound represented by formula I,

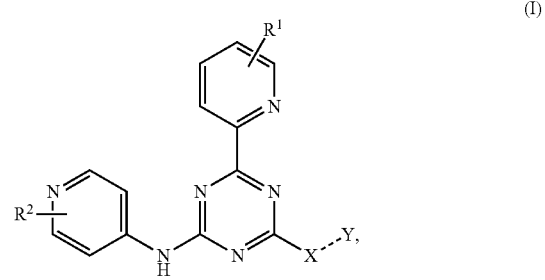

(I)

or its isomer, pharmaceutically acceptable salt, crystal, solvate, or prodrug, as well as their preparation methods and pharmaceutical compositions containing said chemical compound, and an application of said chemical compound or composition. The chemical compound has very good ability to inhibit mutant IDH2 enzyme activity and to inhibit mutant IDH2 neoplastic cells, and may be used for preventing and/or treating a tumor characterized by the presence of mutant IDH2.

10 Claims, 1 Drawing Sheet

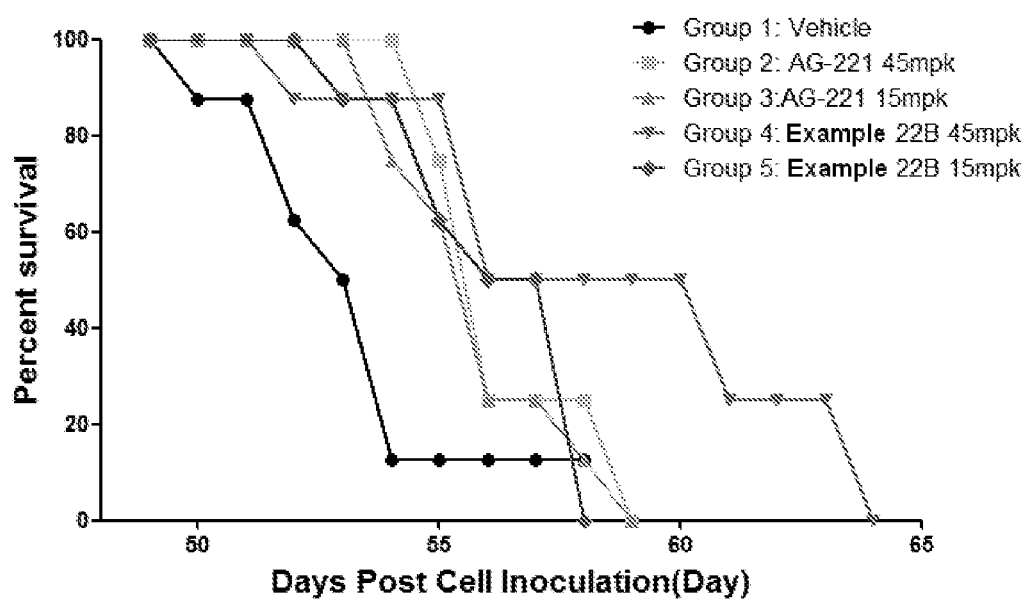

CHEMICAL COMPOUND OF ISOCITRATE DEHYDROGENASE INHIBITOR, AND APPLICATION THEREOF

CROSS REFERENCE TO RELATED APPLICATIONS

This application is a US national phase application based upon PCT Application No. PCT/CN2017/093597 filed on Jul. 20, 2017, which claims the priority of Chinese Patent Application No. 201610580910.0, filed on Jul. 21, 2016, and the disclosures of which are hereby incorporated by reference.

FIELD

The present disclosure belongs to the field of medical chemistry, specifically, to a compound or an isomer, a pharmaceutically acceptable salt, crystal, solvate or prodrug thereof as an isocitrate dehydrogenase 2 inhibitor, methods for producing the same, and pharmaceutical compositions comprising the compounds, and use of the compounds or compositions for treating cancer characterized by the presence of mutant isocitrate dehydrogenase 2.

BACKGROUND

Isocitrate dehydrogenase (IDH) is a rate-limiting enzyme of the tricarboxylic acid cycle, and there are three members in this family: IDH1, IDH2 and IDH3. With $NAD^+$ (nicotinamide adenine dinucleotide, coenzyme I) or $NADP^+$ (nicotinamide adenine dinucleotide phosphate, coenzyme II) as cofactor, IDH catalyzes the oxidative decarboxylation of isocitrate to form α-ketoglutarate (α-KG), and meanwhile, NADH (reduced coenzyme I) or NADPH (reduced coenzyme II) are generated repspectively. IDH isozymes have three forms: NADP-dependent IDH1 located in cytoplasm, NADP-dependent IDH1 located in mitochondria, and NAD-dependent IDH3 located in mitochondria. The gene of IDH1 is located on chromosome 2q33.3, and the protein localizes in the cytoplasm and peroxisomes; the gene of IDH2 is located on chromosome 15q26.1, and the protein localizes in the cellular mitochondria.

IDH2 mutations have been identified in a variety of cancers, such as glioma, glioblastoma multiforme, acute myeloid leukemia (AML). IDH2 mutations include R140 and R172, etc., which occur at or near the critical residues of the active site (see L. Dang et al., Nature, 2009, 462, 739-44). Studies have shown that IDH2 mutations present in cancer cells result in gaining a new ability to catalyze the NAPH-dependent reduction of alpha-ketoglutarate to R(−)-2-hydroxyglutarate (2-HG). High levels of 2-HG have been detected in tumors containing the mutations. For example, high levels of 2-HG have been detected in the plasma of AML patients containing mutant IDH (see S. Gross et al., J. Exp. Med., 2010, 207(2), 339). It is believed that the production of high level of 2-HG caused by IDH2 mutations contributes to the formation and development of cancer (see L. Dang et al., Nature, 2009, 462, 739-44). Thus, treatment of the cancer characterized by the presence of mutant IDH2 by inhibiting the mutant IDH2 and its nascent activity has entered the field of drug researchers. Developing a safe and effective IDH inhibitor has become an important way to treat cancer.

At present, research on drugs that inhibit mutant IDH2 for the treatment of cancer has achieved some success. However, there is still a need to develop more superior IDH2 inhibitors for the treatment of diseases associated with IDH2-mediated events.

SUMMARY

It is an object of the present disclosure to provide a compound represented by formula (I) having an IDH2 inhibitory activity, or an isomer, a pharmaceutically acceptable salt, crystal, solvate or prodrug thereof,

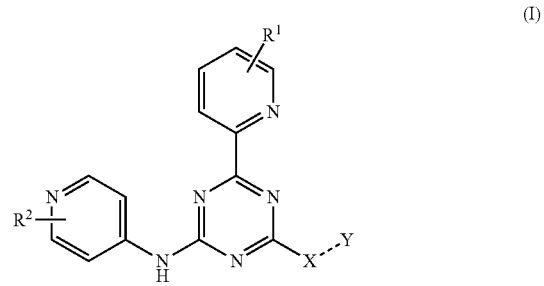

(I)

wherein, $R^1$ and $R^2$ are each independently selected from the group consisting of hydrogen, halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;

X is selected from the group consisting of $N(R^3)$, O, S, and $C(R^4)$, wherein $R^3$ is selected from the group consisting of hydrogen, alkyl, haloalkyl, hydroxyalkyl, aminoalkyl, mercaptoalkyl, and aminomercaptoalkyl, or $R^3$ and Y together with the nitrogen atom to which they are attached form optionally substituted heterocyclyl, and $R^4$ is selected from the group consisting of hydrogen, alkyl, alkenyl, haloalkyl, hydroxyl, hydroxyalkyl, halogen, oxo group, alkoxy, carboxyl, cyano, amino and aminoalkyl, or $R^4$ and Y together with the carbon atom to which they are attached form optionally substituted carbocyclyl or heterocyclyl, wherein the alkyl, haloalkyl, hydroxyalkyl, aminoalkyl, mercaptoalkyl, aminomercaptoalkyl, alkenyl, hydroxyl, halogen, oxo group, alkoxy, carboxyl, cyano, amino are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;

Y is selected from the group consisting of optionally substituted alkyl, $O(R^5)$, $N(R^6R^7)$, cycloalkyl, heterocyclyl, haloalkyl, hydroxyalkyl, alkoxy, haloalkoxy, alkylamino, alkylacylamino, alkylacyl, aminoacyl and alkylaminoacyl, wherein $R^5$, $R^6$ and $R^7$ are each independently selected from the group consisting of optionally substituted alkyl, cycloalkyl and heterocyclyl, or $R^6$ and $R^7$ together with the nitrogen atom to which they are attached form heterocyclyl; and when X is N(R³) and R³ is hydrogen, Y is selected from the group consisting of optionally substituted O(R⁵) and N(R⁶R⁷), and the dotted line between X and Y represents a single bond;

when X is N(R³) and R³ is selected from the group consisting of alkyl, haloalkyl and hydroxyalkyl, mercaptoalkyl and aminomercaptoalkyl, Y is selected from the group consisting of optionally substituted alkyl, O(R⁵) and N(R⁶R⁷), and the dotted line between X and Y represents a single bond, or R³ and Y together with the nitrogen atom to which they are attached form optionally substituted heterocyclyl;

when X is selected from the group consisting of O and S, Y is selected from the group consisting of optionally substituted alkyl, cycloalkyl, heterocyclyl, haloalkyl, hydroxyalkyl, alkoxy, haloalkoxy, alkylamino, alkylacylamino, alkylacyl, aminoacyl and alkylaminoacyl, and the dotted line between X and Y represents a single bond;

when X is C(R⁴), Y is selected from the group consisting of optionally substituted alkyl, cycloalkyl, heterocyclyl, haloalkyl, hydroxyalkyl, alkoxy, haloalkoxy, alkylamino, alkylacylamino, alkylacyl, aminoacyl and alkylaminoacyl, and the dotted line between X and Y represents a single bond, a double bond or a triple bond, or R⁴ and Y together with the carbon atom to which they are attached form optionally substituted carbocyclyl or heterocyclyl.

Another object of the present disclosure is to provide a method for preparing the compound represented by formula (I) of the present disclosure, or an isomer, a pharmaceutically acceptable salt, crystal, solvate or prodrug thereof.

A further object of the present disclosure is to provide a composition comprising the compound of the formula I of the present disclosure or the isomer, pharmaceutically acceptable salt, crystal, solvate or prodrug thereof and a pharmaceutically acceptable carrier, and a composition comprising the compound represented by formula (I) of the present disclosure or the isomer, pharmaceutically acceptable salt, crystal, solvate or prodrug thereof and another one or more IDH2 inhibitors.

It is still another object of the present disclosure to provide a method for treating a cancer characterized by the presence of mutant IDH2 by using the compound represented by the formula (I) of the present disclosure, or an isomer, a pharmaceutically acceptable salt, crystal, solvate or prodrug thereof, and use of the compound represented by the formula (I) of the present disclosure, or the isomer, pharmaceutically acceptable salt, crystal, solvate or prodrug thereof in the manufacture of a medicament for treating cancer characterized by the presence of mutant IDH2.

For the above purposes, the present disclosure provides the following technical solutions.

In a first aspect, the present disclosure provides a compound represented by formula (I), or an isomer, a pharmaceutically acceptable salt, crystal, solvate or prodrug thereof,

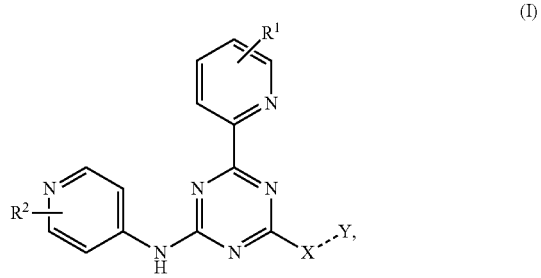

(I)

wherein

R¹ and R² are each independently selected from the group consisting of hydrogen, halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;

X is selected from the group consisting of N(R³), O, S, and C(R⁴), wherein R³ is selected from the group consisting of hydrogen, alkyl, haloalkyl, hydroxyalkyl, aminoalkyl, mercaptoalkyl, and aminomercaptoalkyl, or R³ and Y together with the nitrogen atom to which they are attached form optionally substituted heterocyclyl, and R⁴ is selected from the group consisting of hydrogen, alkyl, alkenyl, haloalkyl, hydroxyl, hydroxyalkyl, halogen, oxo group, alkoxy, carboxyl, cyano, amino and aminoalkyl, or R⁴ and Y together with the carbon atom to which they are attached form optionally substituted carbocyclyl or heterocyclyl, wherein the alkyl, haloalkyl, hydroxyalkyl, aminoalkyl, mercaptoalkyl, aminomercaptoalkyl, alkenyl, hydroxyl, halogen, oxo group, alkoxy, carboxyl, cyano, amino are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;

Y is selected from the group consisting of optionally substituted alkyl, O(R⁵), N(R⁶R⁷), cycloalkyl, heterocyclyl, haloalkyl, hydroxyalkyl, alkoxy, haloalkoxy, alkylamino, alkylacylamino, alkylacyl, aminoacyl and alkylaminoacyl, wherein R⁵, R⁶ and R⁷ are each independently selected from the group consisting of optionally substituted alkyl, cycloalkyl and heterocyclyl, or R⁶ and R⁷ together with the nitrogen atom to which they are attached form heterocyclyl; and when X is N(R³) and R³ is hydrogen, Y is selected from the group consisting of optionally substituted O(R⁵) and N(R⁶R⁷), and the dotted line between X and Y represents a single bond;

when X is N(R³) and R³ is selected from the group consisting of alkyl, haloalkyl, hydroxyalkyl, aminoalkyl, mercaptoalkyl and aminomercaptoalkyl, Y is selected from the group consisting of optionally substituted alkyl, O(R⁵) and N(R⁶R⁷), and the dotted line between X and Y represents a single bond, or R³ and Y together with the nitrogen atom to which they are attached form optionally substituted heterocyclyl;

when X is selected from the group consisting of O and S, Y is selected from the group consisting of optionally substituted alkyl, cycloalkyl, heterocyclyl, haloalkyl, hydroxyalkyl, alkoxy, haloalkoxy, alkylamino, alkylacylamino, alkylacyl, aminoacyl and alkylaminoacyl, and the dotted line between X and Y represents a single bond; and when X is C(R⁴), Y is selected from the group consisting of optionally substituted alkyl, cycloalkyl, heterocyclyl, haloalkyl, hydroxyalkyl, alkoxy, haloalkoxy, alkylamino, alkylacylamino, alkylacyl, aminoacyl and alkylaminoacyl, and the dotted line between X and Y represents a single bond, a double bond or a triple bond, or R⁴ and Y together with the carbon atom to which they are attached form optionally substituted carbocyclyl or heterocyclyl.

In some preferred embodiments, the compound of the present disclosure is a compound represented by formula (I), or an isomer, a pharmaceutically acceptable salt, crystal, solvate or prodrug thereof, wherein $R^1$ and $R^2$ are each independently selected from the group consisting of hydrogen, halogen, hydroxyl, $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, amino, $C_{1-6}$ alkylamino, $C_{1-6}$ alkylacylamino, $C_{1-6}$ alkylacyl, aminoacyl, $C_{1-6}$ alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl; and more preferably, $R^1$ and $R^2$ are each independently selected from the group consisting of hydrogen, halogen, hydroxyl, $C_{1-3}$ alkyl, $C_{3-6}$ cycloalkyl, $C_{3-6}$ heterocyclyl, halo $C_{1-3}$ alkyl, hydroxy $C_{1-3}$ alkyl, $C_{1-3}$ alkoxy, halo $C_{1-3}$ alkoxy, hydroxy $C_{1-3}$ alkoxy, amino, $C_{1-3}$ alkylamino, $C_{1-3}$ alkylacylamino, $C_{1-3}$ alkylacyl, aminoacyl, $C_{1-3}$ alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, $C_{1-6}$ alkyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, nitro, carboxyl, cyano, amino, mono $C_{1-6}$ alkylamino, di $C_{1-6}$ alkylamino, $C_{3-8}$ cycloalkyl, $C_{3-8}$ heterocyclyl, $C_{6-10}$ aryl and $C_{3-10}$ heteroaryl;

even more preferably, $R^1$ and $R^2$ are each independently selected from the group consisting of hydrogen, fluorine, chlorine, bromine, iodine, hydroxyl, methyl, ethyl, propyl, isopropyl, cyclopropyl, cyclobutyl, cyclopentyl, cyclohexyl, trifluoromethyl, trifluoroethyl, hydroxymethyl, hydroxyethyl, hydroxypropyl, 2-hydroxypropyl, trifluoromethoxy, trifluoroethoxy, hydroxymethoxy, hydroxyethoxy, hydroxypropoxy, 2-hydroxypropoxy, methoxy, ethoxy, propoxy, isopropoxy, amino, methylamino, dimethylamino, ethylamino, diethylamino, methylethylamino, methylacylamino, ethylacylamino, vinylacylamino, methylacyl, ethylacyl, vinylacyl, aminoacyl, methylaminoacyl, ethylaminoacyl, carboxyl, nitro and cyano.

In some preferred embodiments, the compound of the present disclosure is a compound represented by formula (I), or an isomer, a pharmaceutically acceptable salt, crystal, solvate or prodrug thereof, wherein X is $N(R^3)$, wherein $R^3$ is hydrogen; and Y is $O(R^5)$, wherein $R^5$ is selected from the group consisting of $C_{1-12}$ alkyl, $C_{3-8}$ cycloalkyl and $C_{3-8}$ heterocyclyl, wherein the $C_{1-12}$ alkyl, $C_{3-8}$ cycloalkyl and $C_{3-8}$ heterocyclyl are optionally substituted with one or more groups selected from the group consisting of alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, X is $N(R^3)$, wherein $R^3$ is hydrogen; and Y is $O(R^5)$, wherein $R^5$ is selected from the group consisting of $C_{1-12}$ alkyl, $C_{3-8}$ cycloalkyl and $C_{3-8}$ heterocyclyl, wherein the $C_{1-12}$ alkyl, $C_{3-8}$ cycloalkyl and $C_{3-8}$ heterocyclyl are optionally substituted with one or more groups selected from the group consisting of $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl; and even more preferably, X is $N(R^3)$, wherein $R^3$ is hydrogen; and Y is $O(R^5)$, wherein $R^5$ is selected from the group consisting of $C_{1-6}$ alkyl, $C_{3-6}$ cycloalkyl and $C_{3-6}$ heterocyclyl, wherein the $C_{1-6}$ alkyl, $C_{3-6}$ cycloalkyl and $C_{3-6}$ heterocyclyl are optionally substituted with one or more groups selected from the group consisting of $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

In some preferred embodiments, the compound of the present disclosure is a compound represented by formula (I), or an isomer, a pharmaceutically acceptable salt, crystal, solvate or prodrug thereof, wherein X is $N(R^3)$, wherein $R^3$ is hydrogen; and Y is $N(R^6R^7)$, wherein $R^6$ and $R^7$ are each independently selected from the group consisting of $C_{1-6}$ alkyl, $C_{3-8}$ cycloalkyl and $C_{3-8}$ heterocyclyl, wherein the $C_{1-6}$ alkyl, $C_{3-8}$ cycloalkyl and $C_{3-8}$ heterocyclyl are optionally substituted with one or more groups selected from the group consisting of alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, X is $N(R^3)$, wherein $R^3$ is hydrogen; and Y is $N(R^6R^7)$, wherein $R^6$ and $R^7$ are each independently selected from the group consisting of $C_{1-6}$ alkyl, $C_{3-8}$ cycloalkyl and $C_{3-8}$ heterocyclyl, wherein the $C_{1-6}$ alkyl, $C_{3-8}$ cycloalkyl and $C_{3-8}$ heterocyclyl are optionally substituted with one or more groups selected from the group consisting of $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl; and even more preferably, X is $N(R^3)$, wherein $R^3$ is hydrogen; and Y is $N(R^6R^7)$, wherein $R^6$ and $R^7$ are each independently selected from the group consisting of $C_{1-3}$ alkyl, $C_{3-6}$ cycloalkyl and $C_{3-6}$ heterocyclyl, wherein the $C_{1-3}$ alkyl, $C_{3-6}$ cycloalkyl and $C_{3-6}$ heterocyclyl are optionally substituted with one or more groups selected from the group consisting of $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

In some preferred embodiments, the compound of the present disclosure is a compound represented by formula (I), or an isomer, a pharmaceutically acceptable salt, crystal, solvate or prodrug thereof, wherein X is $N(R^3)$, wherein $R^3$ is hydrogen; and Y is $N(R^6R^7)$, wherein $R^6$ and $R^7$ together with the nitrogen atom to which they are attached form $C_{3-8}$ heterocyclyl, wherein the heterocyclyl further contains one or more heteroatoms selected from the group consisting of N, O and S, and said heterocyclyl is optionally substituted with one or more groups selected from the group consisting of oxo group, alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, X is $N(R^3)$, wherein $R^3$ is hydrogen, and Y is $N(R^6R^7)$, wherein $R^6$ and $R^7$ together with the nitrogen atom to which they are attached form $C_{3-8}$ heterocyclyl, wherein the heterocyclyl further contains one or more heteroatoms selected from the group consisting of N, O and S, and the heterocyclyl is optionally substituted with one or more groups selected from the group consisting of oxo group, $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl; and even more preferably, X is $N(R^3)$, wherein $R^3$ is hydrogen; and Y is $N(R^6R^7)$, wherein $R^6$ and $R^7$ together with the nitrogen atom to which they are attached form azacyclopropyl, azacyclobutyl, tetrahydropyrrolyl, piperidinyl, dihydropyrrolyl, tetrahydropyridyl, pyrazolidinyl, dihydropyrazolyl, imidazolidinyl, dihydroimidazolyl, pyrazolyl, dihydropyrazolyl, oxazolidinyl, dihydrooxazolyl, thiazolidinyl, dihydrothiazolyl, isoxazolidinyl, dihydroisoxazolyl, isothiazolidinyl, dihydroisothiazolyl, hexahydropyrimidinyl, tetrahydropyrimidinyl, dihydropyrimidinyl, hexahydropyridazinyl, tetrahydropyridazinyl, dihydropyridazinyl, piperazinyl, tetrahydropyrazinyl, dihydropyrazinyl, morpholinyl, thiomorpholinyl and taurultam, wherein the groups are optionally substituted with one or more groups selected from the group consisting of oxo group, $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

In some preferred embodiments, the compound of the present disclosure is a compound represented by formula (I), or an isomer, a pharmaceutically acceptable salt, crystal, solvate or prodrug thereof, wherein X is $N(R^3)$, wherein $R^3$ is selected from the group consisting of $C_{1-6}$ alkyl, halo $C_{1-6}$ alkyl, hydroxy $C_{1-6}$ alkyl, amino $C_{1-6}$ alkyl, mercapto $C_{1-6}$ alkyl and amino mercapto $C_{1-6}$ alkyl; and Y is selected from the group consisting of optionally substituted $C_{1-6}$ alkyl, $O(R^5)$ and $N(R^6R^7)$, cycloalkyl, heterocyclyl, haloalkyl, hydroxyalkyl, alkoxy, haloalkoxy, alkylamino, alkylacylamino, alkylacyl, aminoacyl and alkylaminoacyl, wherein $R^5$, $R^6$ and $R^7$ are each independently selected from the group consisting of $C_{1-6}$ alkyl, $C_{3-8}$ cycloalkyl and $C_{3-8}$ heterocyclyl, wherein the $C_{1-6}$ alkyl, halo $C_{1-6}$ alkyl, hydroxy $C_{1-6}$ alkyl, $C_{3-8}$ cycloalkyl and $C_{3-8}$ heterocyclyl are optionally substituted with one or more groups selected from the group consisting of alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, X is $N(R^3)$, wherein $R^3$ is selected from the group consisting of $C_{1-6}$ alkyl, halo $C_{1-6}$ alkyl, hydroxy $C_{1-6}$ alkyl, amino $C_{1-6}$ alkyl, mercapto $C_{1-6}$ alkyl and amino mercapto $C_{1-6}$ alkyl; and Y is selected from the group consisting of $C_{1-6}$ alkyl, $O(R^5)$, $N(R^6R^7)$, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, $C_{1-6}$ haloalkoxy, $C_{1-6}$ alkylamino, $C_{1-6}$ alkylacylamino, $C_{1-6}$ alkylacyl, aminoacyl and $C_{1-6}$ alkylaminoacyl, wherein $R^5$, $R^6$ and $R^7$ are each independently selected from the group consisting of $C_{1-6}$ alkyl, $C_{3-8}$ cycloalkyl and $C_{3-8}$ heterocyclyl, wherein the $C_{1-6}$ alkyl, halo $C_{1-6}$ alkyl, hydroxy $C_{1-6}$ alkyl, $C_{3-8}$ cycloalkyl and $C_{3-8}$ heterocyclyl are optionally substituted with one or more groups selected from the group consisting of $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl; and even more preferably, X is $N(R^3)$, wherein $R^3$ is selected from the group consisting of $C_{1-6}$ alkyl, halo $C_{1-6}$ alkyl, hydroxy $C_{1-6}$ alkyl, amino $C_{1-6}$ alkyl, mercapto $C_{1-6}$ alkyl and amino mercapto $C_{1-6}$ alkyl; and Y is selected from the group consisting of $C_{1-6}$ alkyl, $O(R^5)$, $N(R^6R^7)$, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, $C_{1-6}$ haloalkoxy, $C_{1-6}$ alkylamino, $C_{1-6}$ alkylacylamino, $C_{1-6}$ alkylacyl, aminoacyl and $C_{1-6}$ alkylaminoacyl, wherein $R^5$, $R^6$ and $R^7$ are each independently selected from the group consisting of $C_{1-6}$ alkyl, $C_{3-8}$ cycloalkyl and $C_{3-8}$ heterocyclyl, wherein the $C_{1-6}$ alkyl, halo $C_{1-6}$ alkyl, hydroxy $C_{1-6}$ alkyl, $C_{3-8}$ cycloalkyl and $C_{3-8}$ heterocyclyl are optionally substituted with one or more groups selected from the group consisting of $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

In some preferred embodiments, the compound of the present disclosure is a compound represented by formula (I), or an isomer, a pharmaceutically acceptable salt, crystal, solvate or prodrug thereof, wherein $R^3$ and Y together with the nitrogen atom to which they are attached form a $C_{3-8}$ heterocyclyl, wherein the heterocyclyl further contains one or more heteroatoms selected from the group consisting of N, O and S, and the heterocyclyl is optionally substituted with one or more groups selected from the group consisting of oxo group, alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, $R^3$ and Y together with the nitrogen atom to which they are attached form a $C_{3-8}$ heterocyclyl, wherein the heterocyclyl further contains one or more heteroatoms selected from the group consisting of N, O and S, and the heterocyclyl is optionally substituted with one or more groups selected from the group consisting of oxo group, $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl; and even more preferably, $R^3$ and Y together with the nitrogen atom to which they are attached form azacyclopropyl, azacyclobutyl, tetrahydropyrrolyl, piperidinyl, dihydropyrrolyl, tetrahydropyridyl, pyrazolidinyl, dihydropyrazolyl, imidazolidinyl, dihydroimidazolyl, pyrazolyl, dihydropyrazolyl, oxazolidinyl, dihydrooxazolyl, thiazolidinyl, dihydrothiazolyl, isoxazolidinyl, dihydroisoxazolyl, isothiazolidinyl, dihydroisothiazolyl, hexahydropyrimidinyl, tetrahydropyrimidinyl, dihydropyrimidinyl, hexahydropyridazinyl, tetrahydropyridazinyl, dihydropyridazinyl, piperazinyl, tetrahydropyrazinyl, dihydropyrazinyl, morpholinyl, thiomorpholinyl and taurultam, wherein the groups are optionally substituted with one or more groups selected from the group consisting of oxo group, $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

In some preferred embodiments, the compound of the present disclosure is a compound represented by formula (I), or an isomer, a pharmaceutically acceptable salt, crystal, solvate or prodrug thereof, wherein the compound represented by formula (I) has a structure represented by formula (Ia):

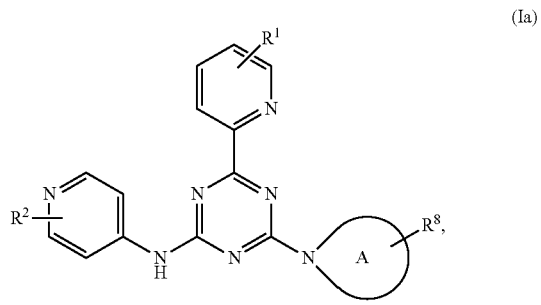

(Ia)

wherein $R^1$ and $R^2$ are each independently selected from the group consisting of hydrogen, halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;

ring A is a heterocyclyl, preferably selected from the group consisting of azaheterocyclyl, azaoxaheterocyclyl, azathiaheterocyclyl and diazaheterocyclyl; and $R^8$ is one or more groups selected from the group consisting of hydrogen, oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl, wherein the oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl or heteroaryl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl.

In some embodiments, the compound of the present disclosure is a compound represented by formula (Ia), or an isomer, a pharmaceutically acceptable salt, crystal, solvate or prodrug thereof, wherein $R^1$ and $R^2$ are each independently selected from the group consisting of hydrogen, halogen, hydroxyl, $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, amino, $C_{1-6}$ alkylamino, $C_{1-6}$ alkylacylamino, $C_{1-6}$ alkylacyl, aminoacyl, $C_{1-6}$ alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, $C_{1-6}$ alkyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, nitro, carboxyl, cyano, amino, mono $C_{1-6}$ alkylamino, di $C_{1-6}$ alkylamino, $C_{3-8}$ cycloalkyl, $C_{3-8}$ heterocyclyl, $C_{6-10}$ aryl and $C_{3-10}$ heteroaryl;

ring A is selected from the group consisting of $C_{3-8}$ azaheterocyclyl, $C_{3-8}$ azaoxaheterocyclyl, $C_{3-8}$ azathiaheterocyclyl and $C_{3-8}$ diazaheterocyclyl; and $R^8$ is one or more groups selected from the group consisting of hydrogen, oxo group, $C_{1-6}$ alkyl, halo $C_{1-6}$ alkyl, hydroxy $C_{1-6}$ alkyl, $C_{3-8}$ cycloalkyl, $C_{3-8}$ heterocyclyl, $C_{1-6}$ alkoxy, halo $C_{1-6}$ alkoxy, hydroxy $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl, wherein the oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl are optionally substituted with one or more groups selected from the group consisting of halogen, hydroxyl, $C_{1-6}$ alkyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, nitro, carboxyl, cyano, amino, mono $C_{1-6}$ alkylamino, di $C_{1-6}$ alkylamino, $C_{3-8}$ cycloalkyl, $C_{3-8}$ heterocyclyl, $C_{6-10}$ aryl and $C_{3-10}$ heteroaryl.

In some embodiments, the compound of the present disclosure is a compound represented by formula (Ia), or an isomer, a pharmaceutically acceptable salt, crystal, solvate or prodrug thereof, wherein ring A is selected from the group consisting of azacyclopropyl, azacyclobutyl, tetrahydropyrrolyl, piperidinyl, dihydropyrrolyl, tetrahydropyridyl, pyrazolidinyl, dihydropyrazolyl, imidazolidinyl, dihydroimidazolyl, pyrazolyl, dihydropyrazolyl, oxazolidinyl, dihydrooxazolyl, thiazolidinyl, dihydrothiazolyl, isoxazolidinyl, dihydroisoxazolyl, isothiazolidinyl, dihydroisothiazolyl, hexahydropyrimidinyl, tetrahydropyrimidinyl, dihydropyrimidinyl, hexahydropyridazinyl, tetrahydropyridazinyl, dihydropyridazinyl, piperazinyl, tetrahydropyrazinyl, dihydropyrazinyl, morpholinyl, thiomorpholinyl and taurultam, wherein the groups are optionally substituted with one or more groups selected from the group consisting of oxo group, $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

In some preferred embodiments, the compound of the present disclosure is a compound represented by the formula (I), or an isomer, a pharmaceutically acceptable salt, crystal, solvate or prodrug thereof, wherein the compound represented by the formula (I) has a structure represented by the following formula (Iaa):

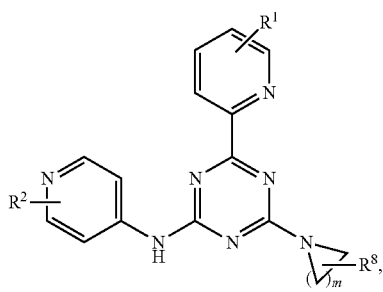

(Iaa)

wherein R¹ and R² are each independently selected from the group consisting of hydrogen, halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;

R⁸ is one or more groups selected from the group consisting of hydrogen, oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl; wherein the oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl; and m is 1, 2, 3, 4, 5 or 6.

In some embodiments, the compound of the present disclosure is a compound represented by the formula (Iaa), or an isomer, a pharmaceutically acceptable salt, crystal, solvate or prodrug thereof, wherein R¹ and R² are each independently selected from the group consisting of hydrogen, halogen, hydroxyl, $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, amino, $C_{1-6}$ alkylamino, $C_{1-6}$ alkylacylamino, $C_{1-6}$ alkylacyl, aminoacyl, $C_{1-6}$ alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, $C_{1-6}$ alkyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, nitro, carboxyl, cyano, amino, mono $C_{1-6}$ alkylamino, di $C_{1-6}$ alkylamino, $C_{3-8}$ cycloalkyl, $C_{3-8}$ heterocyclyl, $C_{6-10}$ aryl and heteroaryl;

R⁸ is one or more groups selected from the group consisting of hydrogen, oxo group, $C_{1-6}$ alkyl, halo $C_{1-6}$ alkyl, hydroxy $C_{1-6}$ alkyl, $C_{3-8}$ cycloalkyl, $C_{3-8}$ heterocyclyl, $C_{1-6}$ alkoxy, halo $C_{1-6}$ alkoxy, hydroxy $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl, wherein the oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl; and m is 1, 2, 3, 4, 5 or 6.

In some embodiments, the compound of the present disclosure is a compound represented by the formula (Iaa), or an isomer, a pharmaceutically acceptable salt, crystal, solvate or prodrug thereof, wherein R¹ and R² are each independently selected from the group consisting of hydrogen, halogen, hydroxyl, $C_{1-3}$ alkyl, $C_{3-6}$ cycloalkyl, $C_{3-6}$ heterocyclyl, halo $C_{1-3}$ alkyl, hydroxy $C_{1-3}$ alkyl, $C_{1-3}$ alkoxy, halo $C_{1-3}$ alkoxy, hydroxy $C_{1-3}$ alkoxy, amino, $C_{1-3}$ alkylamino, $C_{1-3}$ alkylacylamino, $C_{1-3}$ alkylacyl, aminoacyl, $C_{1-3}$ alkylaminoacyl, carboxyl, nitro and cyano, wherein the halogen, hydroxyl, alkyl, cycloalkyl, heterocyclyl, haloalkyl, hydroxyalkyl, alkoxy, haloalkoxy, hydroxyalkoxy, amino, alkylamino, alkylacylamino, alkylacyl, aminoacyl, alkylaminoacyl, carboxyl, nitro and cyano are optionally substituted with one or more groups selected from the group consisting of halogen, hydroxyl, $C_{1-6}$ alkyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, nitro, carboxyl, cyano, amino, mono $C_{1-6}$ alkylamino, di $C_{1-6}$ alkylamino, $C_{3-8}$ cycloalkyl, $C_{3-8}$ heterocyclyl, $C_{6-10}$ aryl and $C_{3-10}$ heteroaryl;

R⁸ is one or more groups selected from the group consisting of hydrogen, oxo group, $C_{1-3}$ alkyl, halo $C_{1-3}$ alkyl, hydroxy $C_{1-3}$ alkyl, $C_{3-6}$ cycloalkyl, $C_{3-6}$ heterocyclyl, $C_{1-3}$ alkoxy, halo $C_{1-3}$ alkoxy, hydroxy $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, aryl and heteroaryl, wherein the oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl are optionally substituted with one or more groups selected from the group consisting of halogen, hydroxyl, $C_{1-6}$ alkyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, nitro, carboxyl, cyano, amino, mono $C_{1-6}$ alkylamino, di $C_{1-6}$ alkylamino, $C_{3-8}$ cycloalkyl, $C_{3-8}$ heterocyclyl, $C_{6-10}$ aryl and $C_{3-10}$ heteroaryl; and m is 1, 2, 3, 4, 5 or 6.

In some embodiments, the compound of the present disclosure is a compound represented by the formula (Iaa), or an isomer, a pharmaceutically acceptable salt, crystal, solvate or prodrug thereof, wherein the group

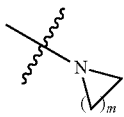

is selected from the group consisting of azacyclopropyl, azacyclobutyl, tetrahydropyrrolyl, and piperidinyl, and $R^8$ is one or more groups selected from the group consisting of hydrogen, oxo group, $C_{1-6}$ alkyl, halo $C_{1-6}$ alkyl, hydroxy $C_{1-6}$ alkyl, $C_{3-8}$ cycloalkyl, $C_{3-8}$ heterocyclyl, $C_{1-6}$ alkoxy, halo $C_{1-6}$ alkoxy, hydroxy $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl, wherein the oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl are optionally substituted with one or more groups selected from the group consisting of halogen, hydroxyl, $C_{1-6}$ alkyl, halo $C_{1-6}$ alkyl, hydroxy $C_{1-6}$ alkyl, $C_{1-6}$ alkoxy, halo $C_{1-6}$ alkoxy, hydroxy $C_{1-6}$ alkoxy, nitro, carboxyl, cyano, amino, mono $C_{1-6}$ alkylamino, di $C_{1-6}$ alkylamino, $C_{3-8}$ cycloalkyl, $C_{3-8}$ heterocyclyl, $C_{6-10}$ aryl and $C_{3-10}$ heteroaryl.

In some specific embodiments, the compound of the present disclosure is a compound represented by the formula (Iaa), or an isomer, a pharmaceutically acceptable salt, crystal, solvate or prodrug thereof, wherein $R^8$ is one or more groups selected from the group consisting of hydrogen, oxo group, fluorine, chlorine, bromine, iodine, hydroxyl, methyl, ethyl, propyl, isopropyl, trifluoromethyl, trifluoroethyl, cyano, amino, carboxyl, nitro, hydroxymethyl, hydroxyethyl, hydroxypropyl, 2-hydroxypropyl, trifluoromethoxy, trifluoroethoxy, hydroxymethoxy, hydroxyethoxy, hydroxypropoxy, 2-hydroxypropoxy, methoxy, ethoxy, propoxy, isopropoxy, amino, methylamino, dimethylamino, ethylamino, diethylamino, methylethylamino, methylacylamino, ethylacylamino, vinylacylamino, methylacyl, ethylacyl, vinylacyl, aminoacyl, methylaminoacyl, ethylaminoacyl, cyclopropyl, cyclobutyl, cyclopentyl and cyclohexyl. In some specific embodiments, the compound of the present disclosure is a compound represented by the formula (Iaa), or an isomer, a pharmaceutically acceptable salt, crystal, solvate or prodrug thereof, wherein the group

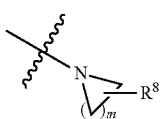

is selected from the group consisting of

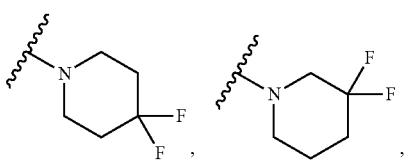

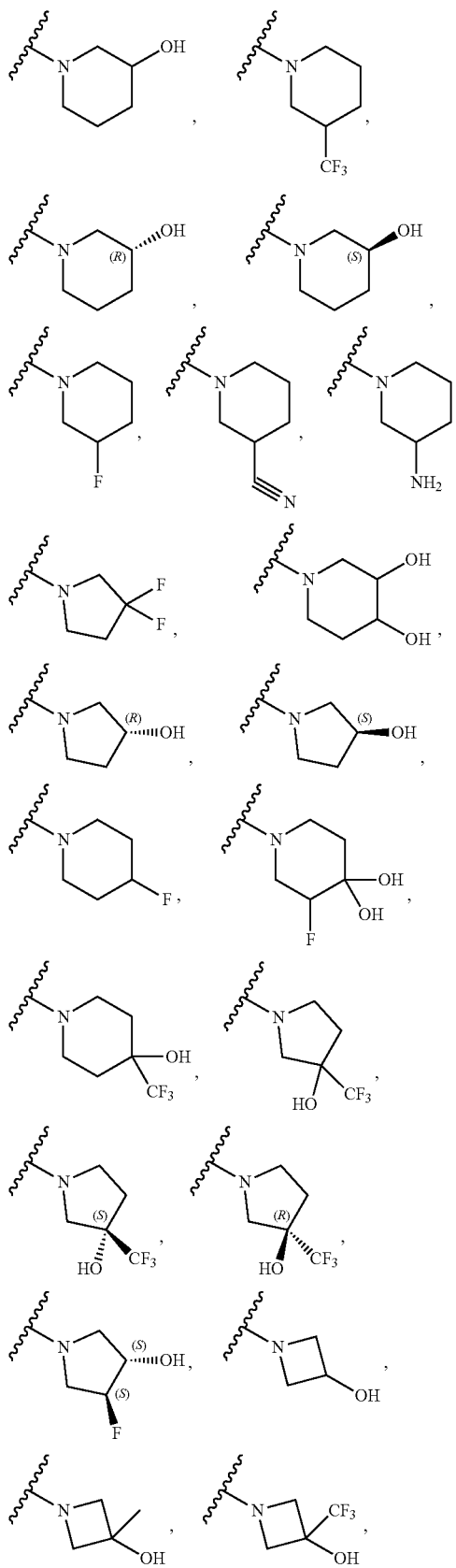

-continued

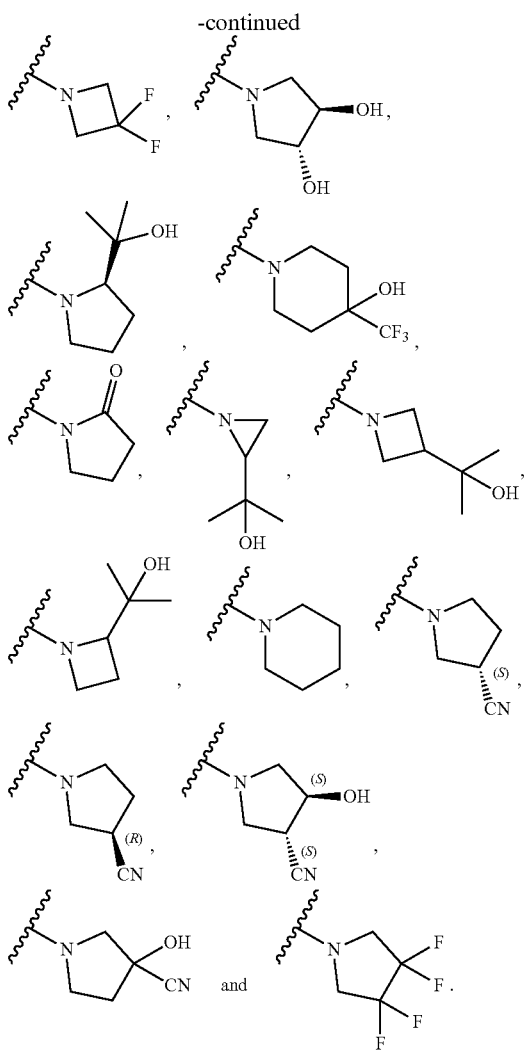

In some preferred embodiments, the compound of the present disclosure is a compound represented by the formula (I), or an isomer, a pharmaceutically acceptable salt, crystal, solvate or prodrug thereof, wherein X is selected from the group consisting of O and S; and Y is selected from the group consisting of $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, $C_{1-6}$ haloalkoxy, $C_{1-6}$ alkylamino, $C_{1-6}$ alkylacylamino, $C_{1-6}$ alkylacyl, aminoacyl and $C_{1-6}$ alkylaminoacyl, wherein the $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, $C_{1-6}$ haloalkoxy, $C_{1-6}$ alkylamino, $C_{1-6}$ alkylacylamino, $C_{1-6}$ alkylacyl, aminoacyl and $C_{1-6}$ alkylaminoacyl are optionally substituted with one or more groups selected from the group consisting of alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, X is selected from the group consisting of O and S; and Y is selected from the group consisting of $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, $C_{1-6}$ haloalkoxy, $C_{1-6}$ alkylamino, $C_{1-6}$ alkylacylamino, $C_{1-6}$ alkylacyl, aminoacyl and $C_{1-6}$ alkylaminoacyl, wherein the $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, $C_{1-6}$ haloalkoxy, $C_{1-6}$ alkylamino, $C_{1-6}$ alkylacylamino, $C_{1-6}$ alkylacyl, aminoacyl and $C_{1-6}$ alkylaminoacyl are optionally substituted with one or more groups selected from the group consisting of $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl; and even more preferably, X is selected from the group consisting of O and S; and Y is selected from the group consisting of $C_{1-3}$ alkyl, $C_{3-6}$ cycloalkyl, $C_{3-6}$ heterocyclyl, halo $C_{1-3}$ alkyl, hydroxy $C_{1-3}$ alkyl, $C_{1-3}$ alkoxy, halo $C_{1-3}$ alkoxy, $C_{1-3}$ alkylamino, $C_{1-3}$ alkylacylamino, $C_{1-3}$ alkylacyl, aminoacyl and $C_{1-3}$ alkylaminoacyl, wherein the $C_{1-3}$ alkyl, $C_{3-6}$ cycloalkyl, $C_{3-6}$ heterocyclyl, halo $C_{1-3}$ alkyl, hydroxy $C_{1-3}$ alkyl, $C_{1-3}$ alkoxy, $C_{1-3}$ haloalkoxy, $C_{1-3}$ alkylamino, $C_{1-3}$ alkylacylamino, $C_{1-3}$ alkylacyl, aminoacyl and $C_{1-3}$ alkylaminoacyl are optionally substituted with one or more groups selected from the group consisting of $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

Without wishing to be bound by the present theory, the inventors of the present disclosure have unexpectedly found that a compound represented by the formula (I) according to the present disclosure, or an isomer, a pharmaceutically acceptable salt, crystal, solvate or prodrug thereof wherein X is O, that is, a compound represented by the following formula (Ib) has an excellent function of inhibiting the enzyme activity of mutant IDH2 and inhibiting tumor cells with mutant IDH2,

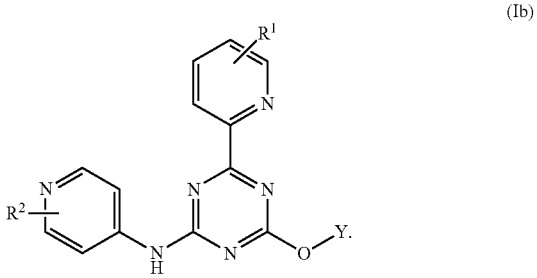

(Ib)

In some embodiments, the compound of the present disclosure is a compound represented by the formula (Ib), or an isomer, a pharmaceutically acceptable salt, crystal, solvate or prodrug thereof, wherein $R^1$ and $R^2$ are each independently selected from the group consisting of hydrogen, halogen, hydroxyl, $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, $C_{1-6}$ haloalkoxy, amino, $C_{1-6}$ alkylamino, $C_{1-6}$ alkylacylamino, $C_{1-6}$ alkylacyl, aminoacyl, $C_{1-6}$ alkylaminoacyl, carboxyl, nitro and cyano; and Y is selected from the group consisting of $C_{1-6}$ alkyl, halo $C_{1-6}$ alkyl, hydroxy $C_{1-6}$ alkyl, $C_{1-6}$ alkoxy, $C_{1-6}$ haloalkoxy, $C_{1-6}$ alkylamino, $C_{1-6}$ alkylacylamino, $C_{1-6}$ alkylacyl, aminoacyl and $C_{1-6}$ alkylaminoacyl. In some specific embodiments, the compound of the present disclosure is a compound of Formula Ib or an isomer, a pharmaceutically acceptable salt, crystal, solvate or prodrug thereof, wherein Y is selected from the group consisting of methyl, ethyl, propyl, isopropyl, trifluoromethyl, trifluoroethyl, trifluoropropyl, trifluoroisopropyl, 2,2,3,3,3-pentafluoropropyl.

In some preferred embodiments, the compound of the present disclosure is a compound represented by the formula (I), or an isomer, a pharmaceutically acceptable salt, crystal, solvate or prodrug thereof, wherein X is $C(R^4)$, wherein $R^4$ is selected from the group consisting of hydrogen, $C_{1-6}$ alkyl, halo $C_{1-6}$ alkyl, hydroxyl, hydroxy $C_{1-6}$ alkyl, halogen, oxo group, $C_{1-6}$ alkoxy, carboxyl, cyano and amino; and Y is selected from the group consisting of $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, halo$C_{1-6}$ alkoxy, $C_{1-6}$ alkylamino, $C_{1-6}$ alkylacylamino, $C_{1-6}$ alkylacyl, aminoacyl and $C_{1-6}$ alkylaminoacyl, wherein the $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, halo $C_{1-6}$ alkoxy, $C_{1-6}$ alkylamino, $C_{1-6}$ alkylacylamino, $C_{1-6}$ alkylacyl, aminoacyl and $C_{1-6}$ alkylaminoacyl are optionally substituted with one or more groups selected from the group consisting of alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, X is $C(R^4)$, wherein $R^4$ is selected from the group consisting of hydrogen, $C_{1-6}$ alkyl, halo $C_{1-6}$ alkyl, hydroxyl, hydroxy $C_{1-6}$ alkyl, halogen, oxo group, $C_{1-6}$ alkoxy, carboxyl, cyano and amino; and Y is selected from the group consisting of $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, halo $C_{1-6}$ alkoxy, $C_{1-6}$ alkylamino, $C_{1-6}$ alkylacylamino, $C_{1-6}$ alkylacyl, aminoacyl and $C_{1-6}$ alkylaminoacyl, wherein the $C_{1-6}$ alkyl, $C_{3-8}$ cycloalkyl, $C_{3-8}$ heterocyclyl, halo $C_{1-6}$ alkyl, hydroxy $C_{1-6}$ alkyl, $C_{1-6}$ alkoxy, halo $C_{1-6}$ alkoxy, $C_{1-6}$ alkylamino, $C_{1-6}$ alkylacylamino, $C_{1-6}$ alkylacyl, aminoacyl and $C_{1-6}$ alkylaminoacyl are optionally substituted with one or more groups selected from the group consisting of $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylaminoacyl, sulfonyl, sulfinyl, mercapto, aryl and heteroaryl; and even more preferably, X is $C(R^4)$, wherein $R^4$ is selected from the group consisting of hydrogen, $C_{1-3}$ alkyl, halo $C_{1-3}$ alkyl, hydroxyl, hydroxy $C_{1-3}$ alkyl, halogen, oxo group, $C_{1-3}$ alkoxy, carboxyl, cyano and amino; and Y is selected from the group consisting of $C_{1-3}$ alkyl, $C_{3-6}$ cycloalkyl, $C_{3-6}$ heterocyclyl, halo $C_{1-3}$ alkyl, hydroxy $C_{1-3}$ alkyl, $C_{1-3}$ alkoxy, halo $C_{1-3}$ alkoxy, $C_{1-3}$ alkylamino, $C_{1-3}$ alkylacylamino, $C_{1-3}$ alkylacyl, aminoacyl and $C_{1-3}$ alkylaminoacyl, wherein the $C_{1-3}$ alkyl, $C_{3-6}$ cycloalkyl, $C_{3-6}$ heterocyclyl, halo $C_{1-3}$ alkyl, hydroxy $C_{1-3}$ alkyl, $C_{1-3}$ alkoxy, $C_{1-3}$ haloalkoxy, $C_{1-3}$ alkylamino, $C_{1-3}$ alkylacylamino, $C_{1-3}$ alkylacyl, aminoacyl and $C_{1-3}$ alkylaminoacyl are optionally substituted with one or more groups selected from the group consisting of $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

In some preferred embodiments, the compound of the present disclosure is a compound represented by the formula (I), or an isomer, a pharmaceutically acceptable salt, crystal, solvate or prodrug thereof, wherein $R^4$ and Y together with the carbon atom to which they are attached form $C_{3-8}$ carbocyclyl or $C_{3-8}$ heterocyclyl, wherein the heterocyclyl further contains one or more heteroatoms selected from the group consisting of N, O and S, and the carbocyclyl and heterocyclyl are optionally substituted with one or more groups selected from the group consisting of oxo group, alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

more preferably, $R^4$ and Y together with the carbon atom to which they are attached form $C_{3-8}$ carbocyclyl or $C_{3-8}$ heterocyclyl, wherein the heterocyclyl further contains one or more heteroatoms selected from the group consisting of N, O and S, and the carbocyclyl and heterocyclyl are optionally substituted with one or more groups selected from the group consisting of oxo group, $C_{1-6}$ alkyl, $C_{3-8}$ cycloalkyl, $C_{3-8}$ heterocycloalkyl, $C_{1-6}$ alkoxy, $C_{1-6}$ alkylamino, halogen, hydroxyl, amino, carboxyl, nitro, cyano, $C_{1-6}$ alkylacyl, aminoacyl, $C_{1-6}$ alkylamino, sulfonyl, sulfinyl, mercapto, aryl and heteroaryl; and even more preferably, $R^4$ and Y together with the carbon atom to which they are attached form cyclopropyl, cyclobutyl, cyclopentyl, cyclohexyl, cyclopropenyl, cyclobutenyl, cyclopentenyl, cyclohexenyl, azacyclopropyl, azacyclobutyl, tetrahydropyrrolyl, piperidinyl, dihydropyrrolyl, tetrahydropyridyl, epoxypropyl, tetrahydrofuranyl, tetrahydropyranyl, dihydrofuranyl, dihydropyranyl, thiorenyl, thietanyl, tetrahydrothienyl, thiacyclohexanyl, dihydrothienyl, pyrazolidinyl, dihydropyrazolyl, imidazolidinyl, dihydroimidazolyl, pyrazolyl, dihydropyrazolyl, oxazolidinyl, dihydrooxazolyl, thiazolidinyl, dihydrothiazolyl, isoxazolidinyl, dihydroisoxazolyl, isothiazolidinyl, dihydroisothiazolyl, hexahydropyrimidinyl, tetrahydropyrimidinyl, dihydropyrimidinyl, hexahydropyridazinyl, tetrahydropyridazinyl, dihydropyridazinyl, piperazinyl, tetrahydropyrazinyl, dihydropyrazinyl, morpholinyl, thiomorpholinyl, dioxanyl, dithianyl, taurultam, bicyclo[2.2.1]heptyl and oxobicyclo[3.1.0]hexyl, wherein the groups are optionally substituted with one or more groups selected from the group consisting of oxo group, $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

The present disclosure provides the following specific compounds:

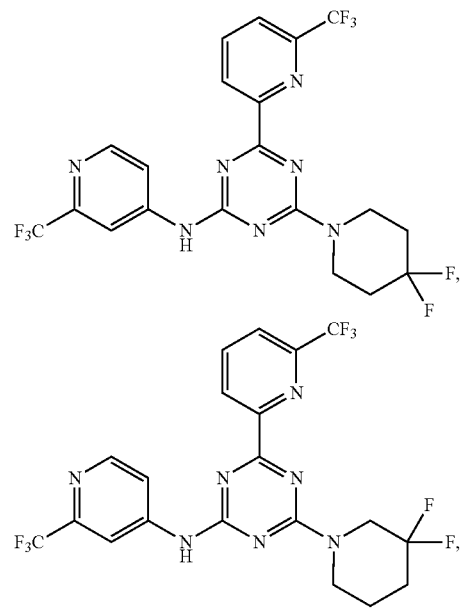

-continued
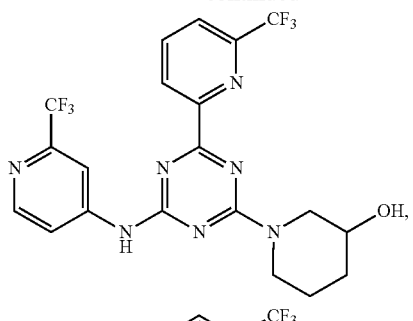
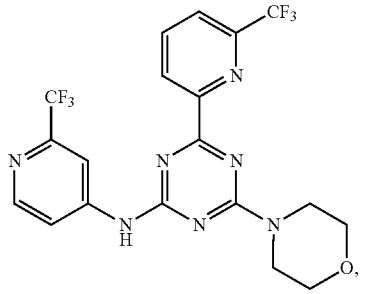
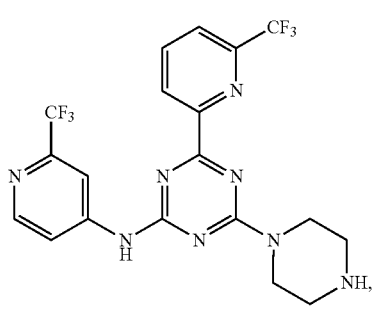
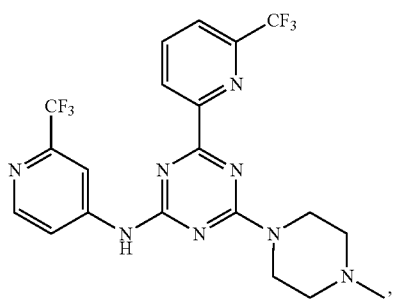
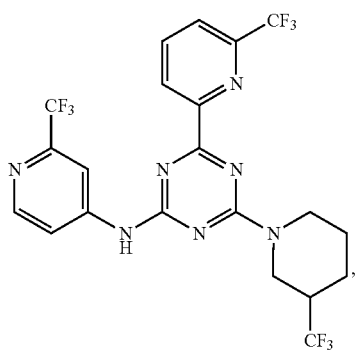
-continued
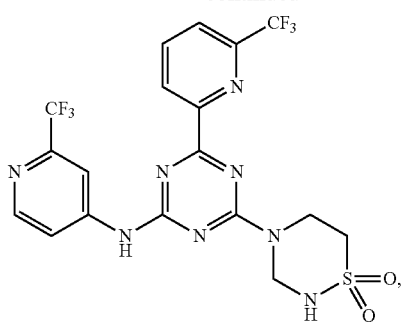
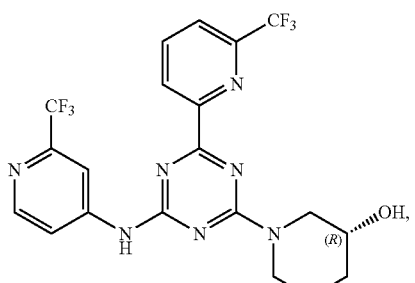
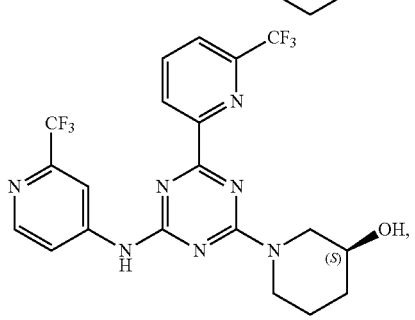
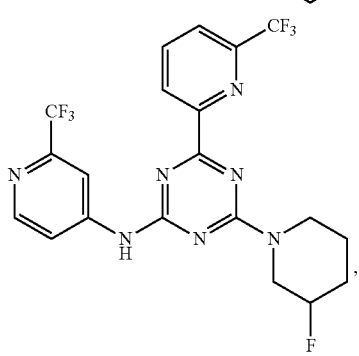
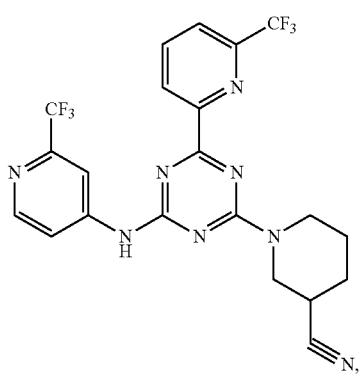

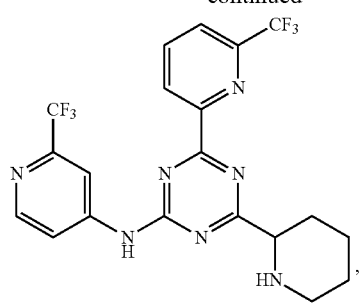
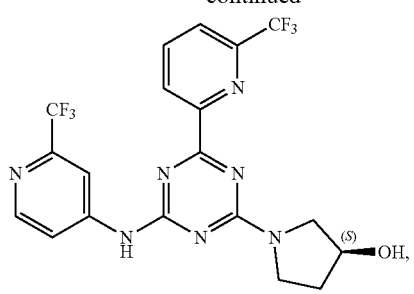
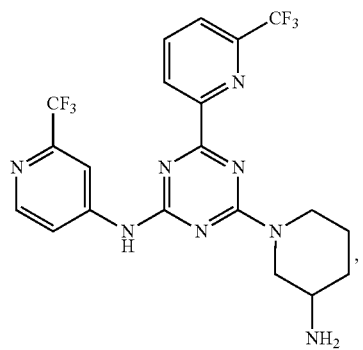
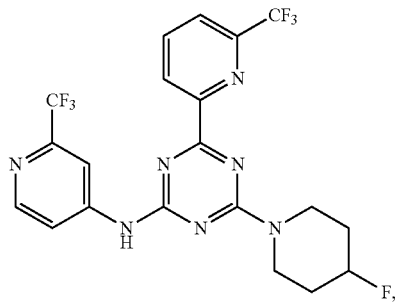
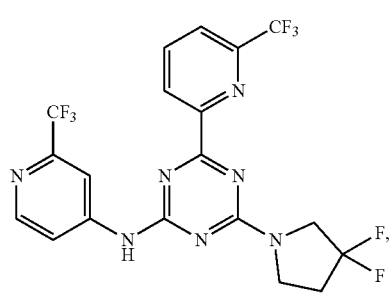
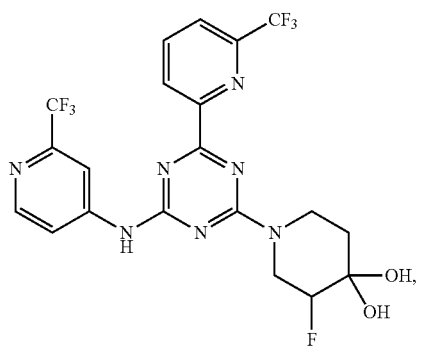
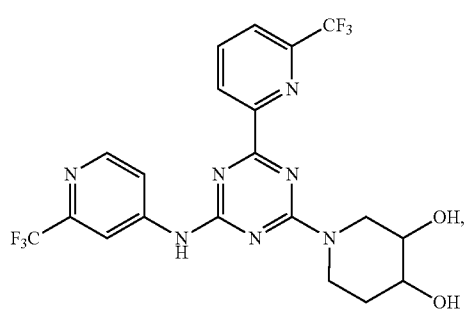
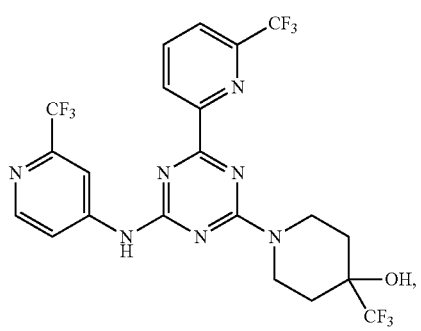
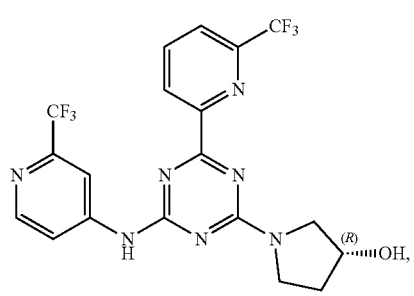
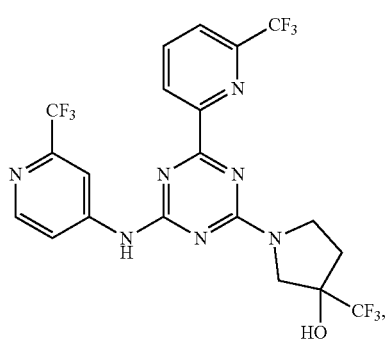

-continued
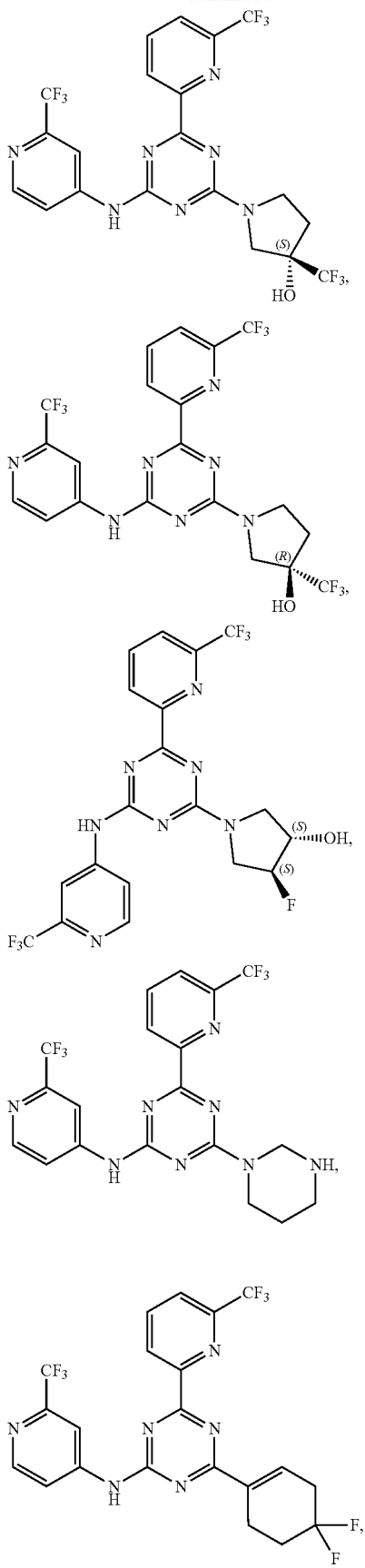
-continued
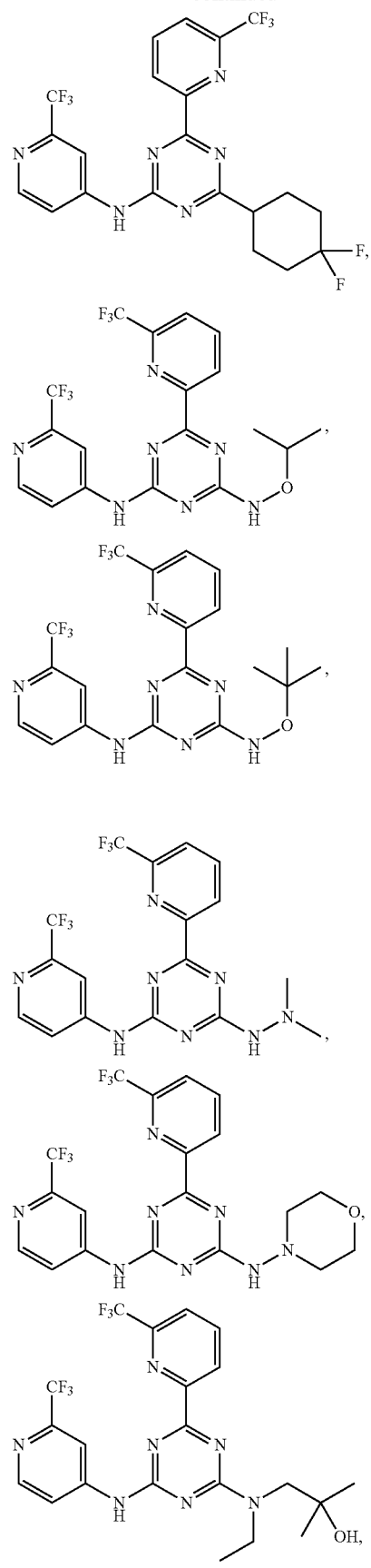

-continued
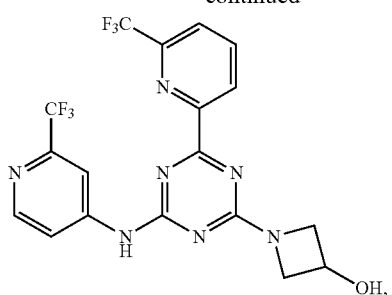
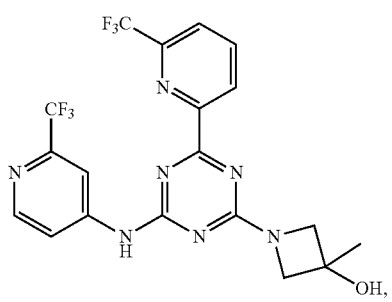
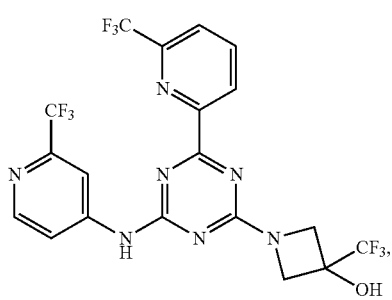
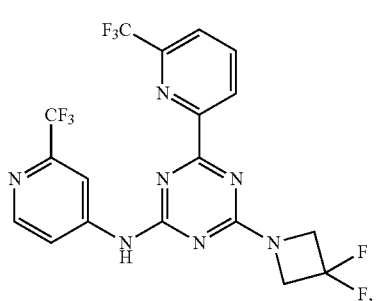
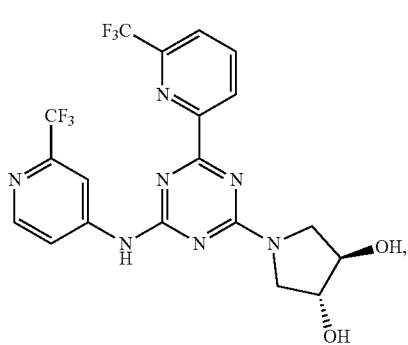
-continued
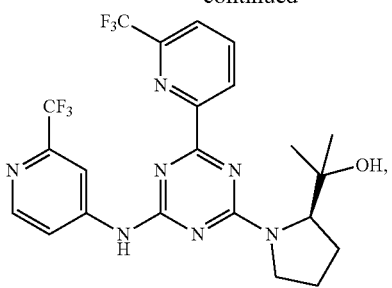
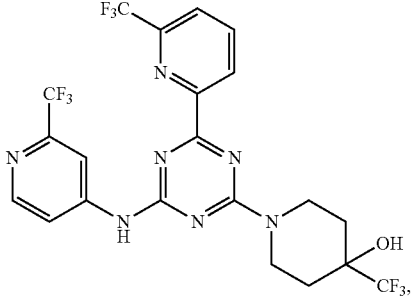
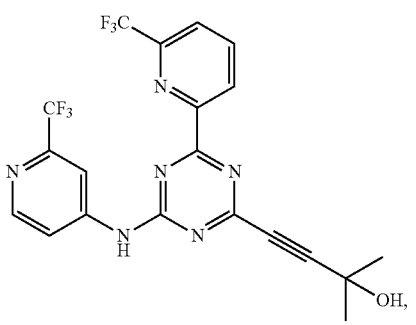
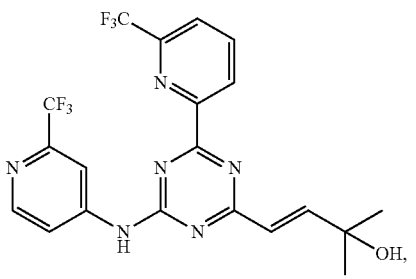
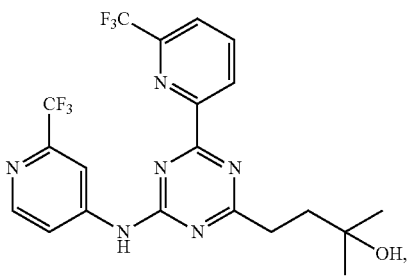
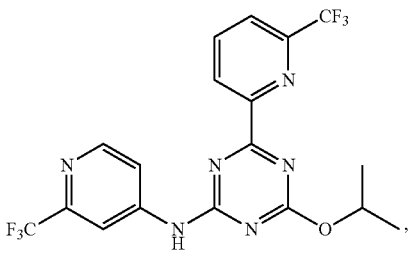

-continued
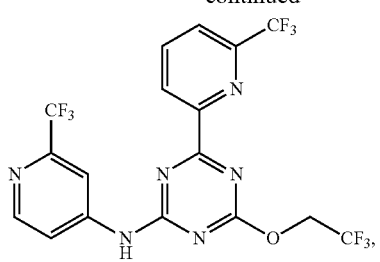
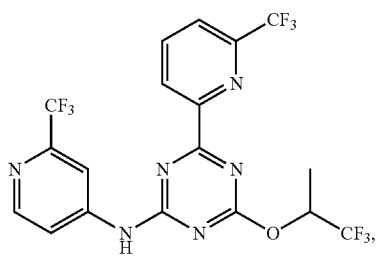
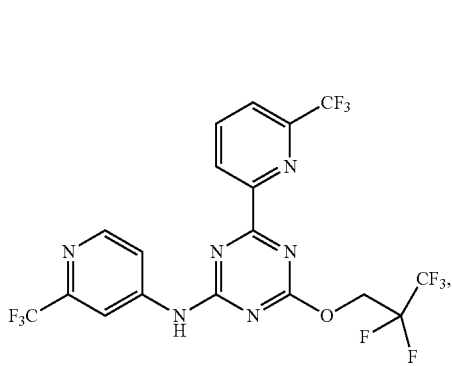
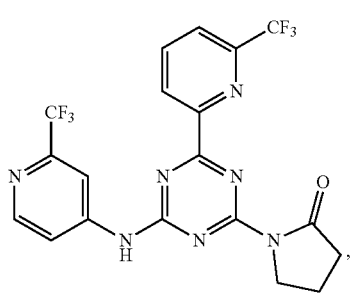
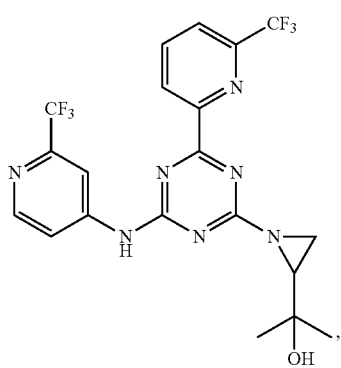
-continued
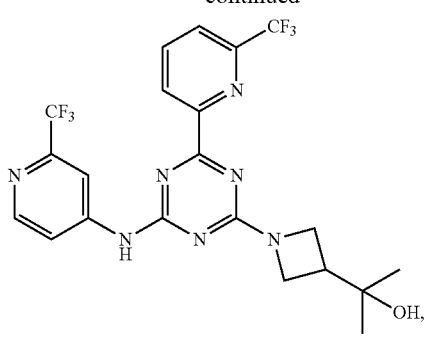
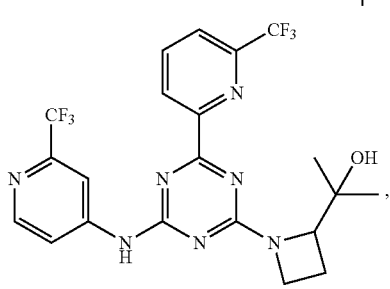
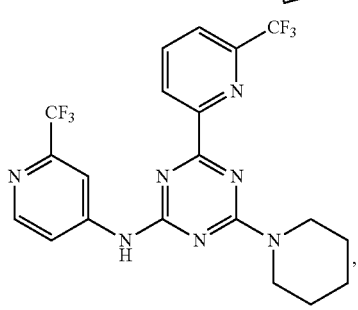
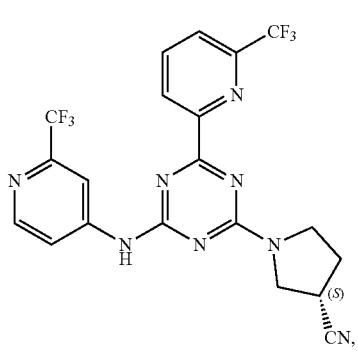
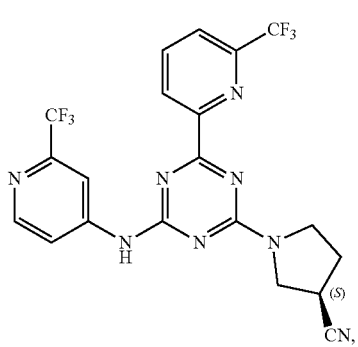

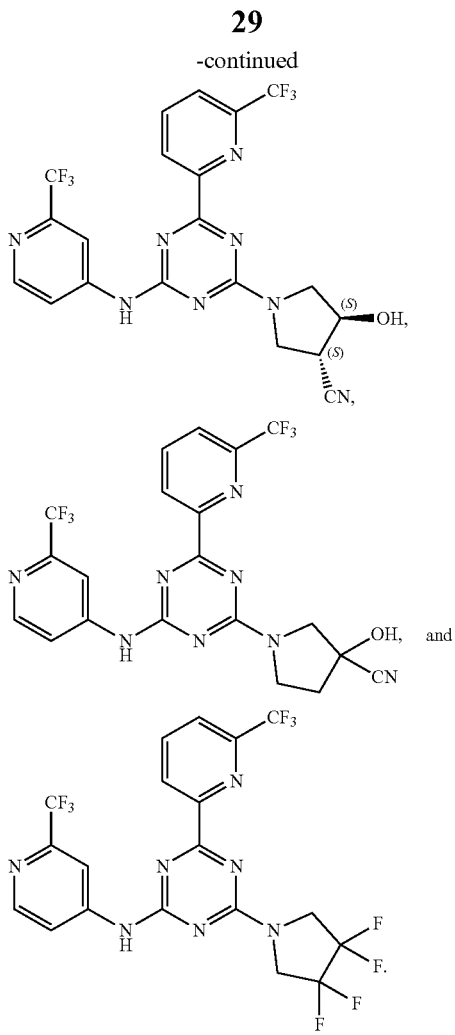

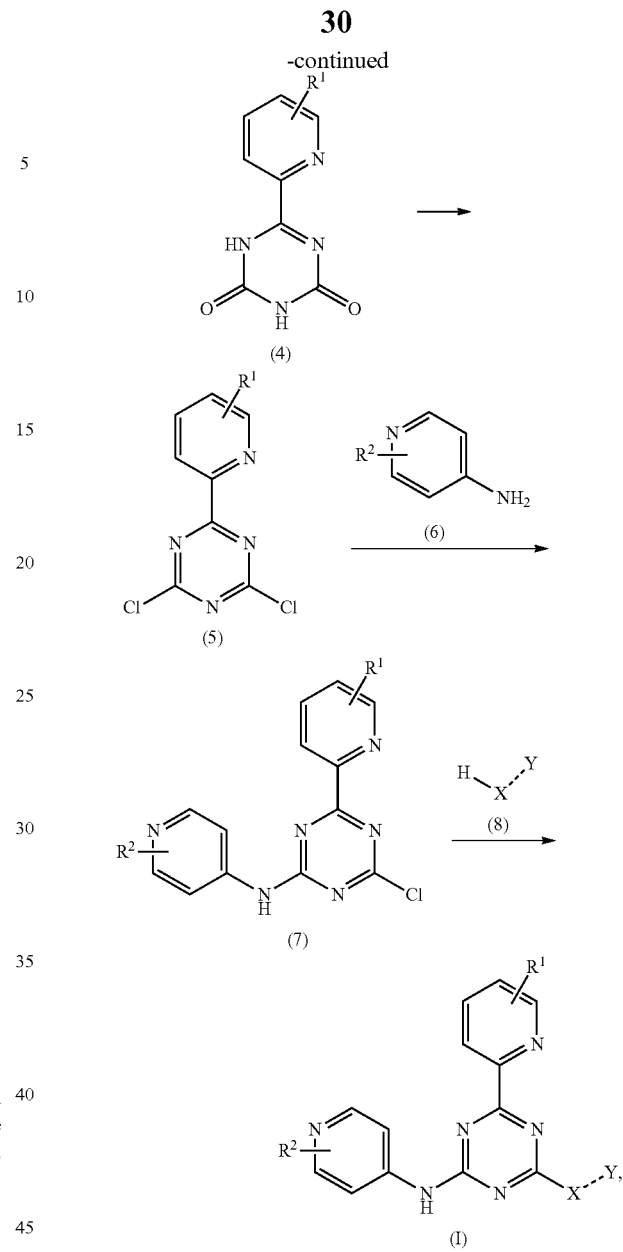

In another aspect, the present disclosure provides a method for preparing the compound represented by the formula (I) of the present disclosure, comprising the steps of:

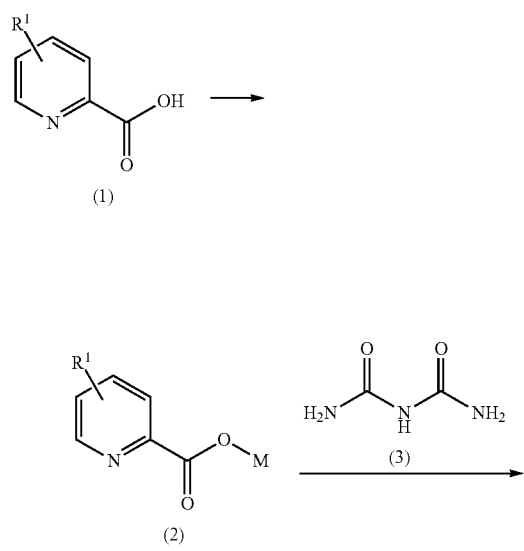

a) esterifying the compound of formula (I) with MOH under the action of thionyl chloride to obtain the compound of formula (2);
b) reacting the compound of formula (2) with the compound of formula (3) under the action of strong base to obtain the compound of formula (4);
c) reacting the compound of formula (4) with phosphorus pentachloride to obtain the compound of formula (5);
d) reacting the compound of formula (5) with the compound of formula (6) to obtain the compound of formula (7); and
e) reacting the compound of formula (7) with the compound of formula (8) or the salt of formula (8) to obtain the compound of formula (I).

Wherein $R^1$, $R^2$, X and Y have the meanings as in the formula (I); M represents alkyl, preferably $C_{1-6}$ alkyl, and more preferably $C_{1-3}$ alkyl.

In a third aspect, the present disclosure provides a pharmaceutical composition, which comprises the compound of the present disclosure or an isomer, a pharmaceutically acceptable salt, crystal, solvate or prodrug thereof.

In some embodiments, the present disclosure provides a pharmaceutical composition, which comprises the compound of the present disclosure or an isomer, a pharmaceutically acceptable salt, crystal, solvate or prodrug thereof, and further comprises one or more selected from IDH1 inhibitor, IDH2 inhibitor, tyrosine protease inhibitor, EGFR inhibitor, VEGFR inhibitor, Bcr-Abl inhibitor, c-kit inhibitor, c-Met inhibitor, Raf inhibitor, MEK inhibitor, histone deacetylase inhibitor, VEGF antibody, EGF antibody, HIV protein kinase inhibitor, HMG-CoA reductase inhibitor and the like.

In some embodiments, the present disclosure provides a compound of the present disclosure or an isomer, a pharmaceutically acceptable salt, crystal, solvate or prodrug thereof, and a pharmaceutical composition comprising the compound of the present disclosure or the isomer, pharmaceutically acceptable salt, crystal, solvate or prodrug thereof, wherein the compound or the pharmaceutical composition is used for treating cancer characterized by the presence of mutant IDH2.

The compound of the present disclosure, or the isomer, pharmaceutically acceptable salt, crystal, solvate or prodrug thereof, may be mixed with a pharmaceutically acceptable carrier, diluent or excipient to prepare a pharmaceutical preparation suitable for oral or parenteral administration. Methods of administration include, but are not limited to, intradermal, intramuscular, intraperitoneal, intravenous, subcutaneous, intranasal, and oral routes. The preparations may be administered via any route, for example, via infusion or bolus, by a route of absorption through epithelium or skin mucosa (e.g., oral mucosa or rectum, etc.). Administration can be systemic or topical. Examples of the orally administered preparation include solid or liquid dosage forms, specifically, tablets, pills, granules, powders, capsules, syrups, emulsions, suspensions and the like. The preparations may be prepared by methods known in the art, and carriers, diluents or excipients conventionally used in the field of pharmaceutical preparations may be included.

In a fourth aspect, the present disclosure provides the use of the compound represented by the formula (I), or the isomer, pharmaceutically acceptable salt, crystal, solvate or prodrug thereof in treatment, for example, as inhibitor of mutant IDH2 having 2-HG neomorphic activity. The present disclosure further provides the use of the compound represented by the formula (I), or the isomer, pharmaceutically acceptable salt, crystal, solvate or prodrug thereof, as inhibitor of IDH2 having mutation at residue 140 or 172, such as R140Q, R140G, R172K, R172M, R172S, R172G and R172W. In some embodiments, the treatment is for a cancer associated with mutant IDH2 having 2-HG neomorphic activity. In other embodiments, the cancer is associated with mutant IDH2 having 2-HG neomorphic activity, wherein the mutation is at residue R140 or 172, such as R140Q, R140G, R172K, R172M, R172S, R172G, and R172W. The present disclosure provides use of the compound represented by the formula (I) of the present disclosure, or the isomer, pharmaceutically acceptable salt, crystal, solvate or prodrug thereof, or the pharmaceutical composition comprising the same in the manufacture of a medicament for treating cancer characterized by the presence of mutant IDH2, wherein the cancer is selected from melanoma, papillary thyroid tumor, cholangiocarcinoma, colon cancer, ovarian cancer, lung cancer, malignant lymphoma, cancers and sarcomas of liver, kidney, bladder, prostate, breast and pancreas, as well as primary and recurrent solid tumors of skin, colon, thyroid, lungs and ovaries, or leukemias and the like. In a specific embodiment, the cancer to be treated is glioblastoma (glioma), myelodysplastic syndrome (MDS), myeloid proliferative neoplasm (MPN), acute myeloid leukemia (AML), sarcoma, melanoma, non-small cell lung cancer, chondrosarcoma, cholangiocarcinoma or angioimmunoblastic lymphoma. In a more specific embodiment, the cancer to be treated is glioblastoma (glioma), myelodysplastic syndrome (MDS), myeloid proliferative neoplasm (MPN), acute myeloid leukemia (AML), melanoma, chondrosarcoma, or vascular immunoblastic non-Hodgkin's lymphoma (NHL). In some embodiments, the present disclosure relates to a method for treating cancer characterized by the presence of mutant IDH2, comprising administering to a subject in need thereof a therapeutically effective amount of the compound represented by the formula (I), or an isomer, a pharmaceutically acceptable salt, crystal, solvate or prodrug thereof, or a pharmaceutical composition comprising the same, wherein the cancer is selected from melanoma, papillary thyroid tumor, cholangiocarcinoma, colon cancer, ovarian cancer, lung cancer, malignant lymphoma, cancers and sarcomas of liver, kidney, bladder, prostate, breast and pancreas, as well as primary and recurrent solid tumors of skin, colon, thyroid, lungs and ovaries, and leukemias.

Terminology

Unless stated to the contrary, terms used in the specification and claims have the following meanings.

The "halogen" of the present disclosure refers to fluorine, chlorine, bromine or iodine.

The "alkyl group" of the present disclosure refers to a linear or branched saturated aliphatic hydrocarbon group, preferably a linear or branched group having 1 to 6 carbon atoms, and more preferably a linear or branched group having 1 to 3 carbon atoms. The non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, and the like. The alkyl can be substituted or unsubstituted, and when the alkyl is a substituted alkyl, the substituent can be at any point of junction which is applicable. The "haloalkyl" of the present disclosure refers to an alkyl substituted with at least one halogen. The "hydroxyalkyl" of the present disclosure refers to an alkyl substituted with at least one hydroxyl. The "carbocyclyl" of the present disclosure refers to a non-aromatic monocyclic, bicyclic or tricyclic hydrocarbon ring system. Carbocyclyl includes fully saturated cyclic systems (such as cycloalkyl) and partially saturated cyclic systems.

The "cycloalkyl" of the present disclosure includes a saturated cyclic, bicyclic, tricyclic or polycyclic hydrocarbon group having 3 to 12 carbons. Any ring atom can be substituted (e.g., substituted with one or more substituents). Examples of cycloalkyl include, but are not limited to, cyclopropyl, cyclohexyl, methylcyclohexyl, adamantyl and norbornyl.

The "alkoxy" of the present disclosure refers to —O-alkyl.

The "alkylamino" of the present disclosure refers to —NH-alkyl or —N-(alkyl)(alkyl).

The "alkylacyl" of the present disclosure refers to —C(O)-alkyl.

The "aminoacyl" of the present disclosure refers to —C(O)—NH$_2$, and the term "alkylaminoacyl" refers to —C(O)—NH-alkyl or —C(O)—N-(alkyl)(alkyl).

The "heterocyclyl" of the present disclosure refers to non-aromatic 3-10 membered monocyclic ring system containing 1 to 3 heteroatoms, 8-12 membered bicyclic ring system containing 1 to 6 heteroatoms or 11-14 membered tricyclic ring system containing 1 to 9 heteroatoms, wherein the heteroatoms are selected from the group consisting of O, N and S (or an oxidized form such as $N^+$—$O^-$, S(O) and $S(O)_2$). The heteroatom can optionally be the attachment point of the heterocyclyl. Examples of heterocyclyl include, but are not limited to, tetrahydrofuranyl, tetrahydropyranyl, piperidinyl, morpholinyl, pyrrolinyl, pyrimidinyl and pyrrolidinyl. Heterocyclyl includes fully saturated cyclic systems and partially saturated cyclic systems.

The "alkoxy" of the present disclosure refers to —O-alkyl. Non-limiting examples of alkoxy include methoxy, ethoxy, propoxy, n-propoxy, isopropoxy, isobutoxy, sec-butoxy, and the like. The alkoxy can be optionally substituted or unsubstituted, and when the alkoxy is substituted, the substituent can be at any point of junction which is applicable.

The "aryl" of the present disclosure refers to aromatic system which may comprise a monocyclic or fused polycyclic ring, preferably a monocyclic or fused bicyclic aromatic system containing 6 to 18 carbon atoms, more preferably about 6 to about 14 carbon atoms. Suitable aryl group includes, but is not limited to, phenyl, naphthyl, anthracenyl, tetrahydronaphthyl, anthracenyl and indanyl.

The "heteroaryl" of the present disclosure refers to aryl having at least one carbon atom substituted with heteroatom, wherein the heteroatom is O, S or N. Suitable heteroaryl includes, but is not limited to, imidazolyl, benzimidazolyl, imidazopyridyl, quinazolinone, pyrrolyl, imidazolyl ketone, furyl, thienyl, pyrazolyl, oxazolyl, thiazolyl, isoxazolyl, isothiazolyl, oxadiazolyl, triazolyl and the like.

The "$C_3$-$C_8$ heterocycly" of the present disclosure refers to substituted or unsubstituted, saturated, partially saturated and fully unsaturated heterocyclic group containing at least one heteroatom and a total ring number of 3, 4, 5, 6, 7, or 8. For example, $C_{3-8}$ azaheterocyclyl, $C_{3-8}$ azaoxaheterocyclyl, $C_{3-8}$ azathiaheterocyclyl and $C_{3-8}$ diazaheterocyclyl refer to substituted or unsubstituted, saturated, partially saturated and fully unsaturated nitrogen-containing heterocyclyl, nitrogen and oxygen-containing heterocyclyl, nitrogen and sulphur-containing heterocyclyl, and dinitrogen-containing heterocyclyl, with a total ring number of 3, 4, 5, 6, 7, or 8.

The "$C_{3-10}$ heteroaryl" of the present disclosure refers to a heteroaryl having at least one heteroatom and a total ring number of 3, 4, 5, 6, 7, 8, 9, or 10. Similarly, $C_{3-6}$ heteroaryl refers to a heteroaryl having at least one heteroatom and a total ring number of 3, 4, 5 or 6.

The compound of the present disclosure contains a plurality of asymmetric centers, therefore, it may present in the forms of single enantiomer, enantiomer, mixture of single enantiomers, diastereomer, mixture of diastereomers, and single diastereomer. "Isomer" of the present disclosure includes, for example, tautomer, cis-trans-isomer, enantiomer, and conformational isomer. Thus, single stereoisomer as well as mixture of enantiomers, diastereomers of the compounds of the present disclosure are within the scope of the present disclosure. All tautomeric forms of the compounds of the present disclosure are within the scope of the present disclosure unless otherwise indicated. "Optionally substituted" refers to a group such as alkyl, O ($R^5$), N($R^6R^7$), cycloalkyl, heterocyclyl, haloalkyl, hydroxyalkyl, alkoxy, haloalkoxy, alkylamino, alkylacylamino, alkylacyl, aminoacyl, alkylaminoacyl, carbocyclyl, aminoalkyl, mercaptoalkyl, aminomercaptoalkyl may be unsubstituted or be substituted with one or more substituents as defined in formula I, for example, by one or more alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl.

The "solvate" of the present disclosure refers to a general definition of a complex formed by a combination of a solute (such as an active compound, a salt of an active compound) and a solvent (such as water). Solvent refers to a solvent known or readily determinable by those skilled in the art. In the case of water, the solvate often refers to a hydrate such as a monohydrate, a dihydrate, a trihydrate and the like.

The "prodrug" of the present disclosure refers to a compound which can be converted into a compound of the formula (I) by a reaction with an enzyme, gastric acid and the like under physiological conditions in a living body, that is, a compound converted into a compound of the formula (I) by oxidation, reduction, hydrolysis and the like of an enzyme, and/or by a hydrolysis reaction of gastric acid and the like.

The "pharmaceutical composition" of the present disclosure refers to a compound comprising any one of the compounds described herein, including the corresponding isomer, prodrug, solvate, pharmaceutically acceptable salt or chemically protected form thereof, and one or more pharmaceutically acceptable carriers. The pharmaceutical composition is aimed to facilitate the administration of a compound to an organism. The compositions are typically used in the manufacture of a medicament for the treatment and/or prevention of a disease mediated by one or more kinases.

The "pharmaceutically acceptable carrier" of the present disclosure refers to a carrier which does not cause significant irritation to an organism and does not interfere with the biological activity and properties of the administered compound, and includes all solvents, diluents or other excipients, dispersing agents, surfactants, isotonic agents, thickeners or emulsifiers, preservatives, solid binders, lubricants, and the like, unless any conventional carrier medium incompatible with the compounds of the present disclosure. Some examples of pharmaceutically acceptable carriers include, but are not limited to, sugars such as lactose, glucose and sucrose; starches such as corn starch and potato starch; cellulose and derivatives thereof, such as sodium carboxymethylcellulose, and cellulose and cellulose acetate; malt, gelatin and the like.

The "excipient" of the present disclosure refers to an inert substance that is added to a pharmaceutical composition to further facilitate administration of the compound. Excipients may include calcium carbonate, calcium phosphate, various sugars and various types of starches, cellulose derivatives, gelatins, vegetable oils, and polyethylene glycols.

The "neomorphic activity" of the present disclosure refers to novel protein activity which is not possessed or exhibited by the wild-type protein to a significant extent. For example, neomorphic activity associated with mutant form of IDH2 is the ability to reduce α-ketoglutarate to 2-hydroxyglutaric acid (i.e., 2-HG, especially R-2-HG). Wild type IDH2 does not have the ability to reduce α-ketoglutaric acid to 2-hydroxyglutaric acid (i.e., 2-HG, especially R-2-HG), or if it has the ability, but it does not produce a significant amount (i.e., harmful or disease-causing) of 2-HG.

The "treating a cancer characterized by the presence of mutant IDH2" of the present disclosure refers to improving the cancer having IDH2 mutation, for example, a mutation at the residue R140 or 172, inhibiting the growth, development and/or metastasis of the cancer, or reducing the risk of cancer, by administering a therapeutically and/or prophylactically effective amount of a compound of the present disclosure to a human or animal in need thereof to inhibit, slow or reverse the growth, progression or spread of cancer, thereby treating cancer or reducing the risk of cancer. The tumours include cancers, such as bladder cancer, breast cancer, kidney cancer, liver cancer, lung cancer (including small cell lung cancer), esophageal cancer, gallbladder cancer, ovarian cancer, pancreatic cancer, stomach cancer, cervix cancer, thyroid cancer, prostate cancer, and skin cancer (including squamous cell carcinoma); hematopoietic tumors of the lymphoid line, including, for example, leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, and Burkitt's lymphoma; mesenchymal-derived tumors, including, for example, fibrosarcoma, rhabdomyosarcoma; hematopoietic tumors of the myeloid line, including, for example, acute and chronic myeloid leukemia, myelodysplastic syndrome, and promyelocytic leukemia; central and peripheral nervous system tumors, including, for example, astrocytoma, neuroblastoma, glial tumors and schwannomas; and other tumors, including, for example, melanoma, seminoma, teratocarcinoma, osteosarcoma, xeroderma pigmentosum, keratoacanthoma, thyroid follicular carcinoma, and Kaposi's sarcoma.

The "pharmaceutically acceptable salt" of the present disclosure refers to a salt of the compound of the present disclosure, which is safe and effective for use in mammals and has the desired biological activity.

"Hydrogen" and "carbon" in the compound of the present disclosure include all isotopes thereof. Isotope should be understood to include those atoms having the same atom number but having different mass numbers, such as hydrogen isotopes including tritium and deuterium, carbon isotopes including $^{13}C$ and $^{14}C$, and oxygen isotopes including $^{16}O$ and $^{18}O$ and the like.

BRIEF DESCRIPTION OF DRAWINGS

FIG. 1 shows the survival rate of mice in each group after inoculating with AM7577 cells in a human acute myeloid leukemia NOD/SCID animal model, wherein the horizontal ordinate is the time (days) after cell inoculation and the vertical ordinate is the percentage of survival (%), including control group , groups of example 22B at 15 mg/kg and 45 mg/kg ( , ) and groups of AG-221 at 15 mg/kg and 45 mg/kg ( , ).

DETAILED DESCRIPTION

The following representative examples are intended to better illustrate the present disclosure and are not intended to limit the scope of the present disclosure. The materials used in the following examples are commercially available unless otherwise specified.

Example 1: 4-(4,4-Difluoropiperidin-1-yl)-6-(6-(trifluoromethyl)pyridin-2-yl)-N-(2-(trifluoromethyl)pyridin-4-yl)-1,3,5-triazin-2-amine

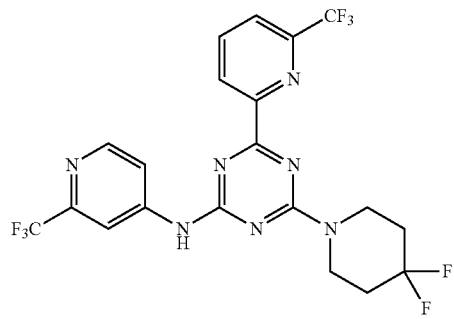 [SMILES: FC1(F)CCN(c2nc(Nc3ccnc(C(F)(F)F)c3)nc(-c3cccc(C(F)(F)F)n3)n2)CC1]

Step 1 Preparation of methyl 6-(trifluoromethyl)picolinate

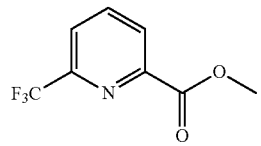

6-Trifluoromethylpyridine-2-carboxylic acid (25 g, 130.8 mmol) was dissolved in 300 mL of methanol, and thionyl chloride (23.3 g, 196.2 mmol) was added dropwise. After addition, the mixture was refluxed for reaction for 12 h. The resultant solution was concentrated until dry, and saturated sodium hydrogen carbonate solution was added to adjust the pH, and then the resultant was extracted with ethyl acetate, dried over anhydrous sodium sulfate to give the title compound.

Step 2 Preparation of 6-(6-(trifluoromethyl)pyridin-2-yl)-1,3,5-triazin-2,4-(1H,3H)-dione

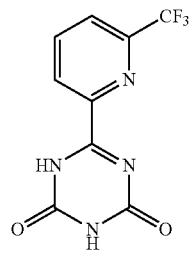 [SMILES: O=c1nc(-c2cccc(C(F)(F)F)n2)[nH]c(=O)[nH]1]

Biuret (13 g, 126.3 mmol) was dissolved in 300 mL of ethylene glycol dimethyl ether, and sodium hydride (42 g, 1053 mmol) was added in batches. The mixture was stirred at 50° C. for 1 h. Methyl 6-(trifluoromethyl)picolinate (21.6 g, 105.3 mmol) was added and the mixture was heated at 85° C. for 16 h. The resultant solution was poured into water, and the pH was adjusted with concentrated hydrochloric acid. The resultant was filtered, and the filter cake was dried to give the title compound.

Step 3 Preparation of 2,4-dichloro-6-(6-(trifluoromethyl)pyridin-2-yl)-1,3,5-triazine

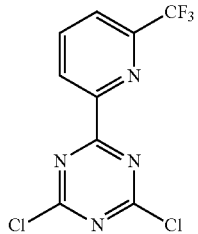 [SMILES: FC(F)(F)c1cccc(-c2nc(Cl)nc(Cl)n2)n1]

6-(6-(Trifluoromethyl)pyridin-2-yl)-1,3,5-triazin-2,4-(1H,3H)-dione (35 g, 135.6 mmol) was dissolved in 200 mL of phosphorus oxychloride, and phosphorus pentachloride (100 g, 542.3 mmol) was added. The mixture was heated at 105° C. for 12 h. The resultant solution was poured into water, extracted with dichloromethane, dried over anhydrous sodium sulfate, and concentrated to give the title compound.

Step 4 Preparation of 4-chloro-6-(6-(trifluoromethyl)pyridin-2-yl)-N-(2-(trifluoromethyl)pyridin-4-yl)-1,3,5-triazin-2-amine

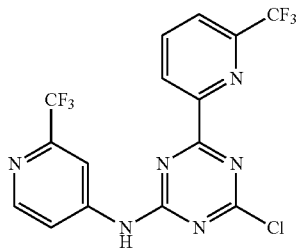 [SMILES: FC(F)(F)c1cc(Nc2nc(Cl)nc(-c3cccc(C(F)(F)F)n3)n2)ccn1]

2,4-Dichloro-6-(6-(trifluoromethyl)pyridin-2-yl)-1,3,5-triazine (7 g, 23.72 mmol) was dissolved in 50 mL of tetrahydrofuran, and 2-(trifluoromethyl)pyridin-4-amine (4.2 g, 26.1 mmol) and sodium carbonate (3.8 g, 35.6 mmol) were added. The mixture was heated under reflux for 72 h. The resultant solution was filtered, and the filtrate was purified by column chromatography, to give the title compound.

Step 5 Preparation of 4-(4,4-difluoropiperidin-1-yl)-6-(6-(trifluoromethyl)pyridin-2-yl)-N-(2-(trifluoromethyl)pyridine-4-yl)-1,3,5-triazin-2-amine

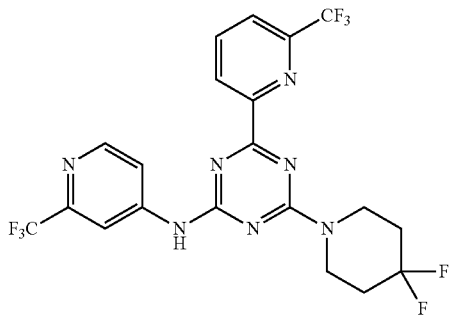 [SMILES: FC1(F)CCN(c2nc(Nc3ccnc(C(F)(F)F)c3)nc(-c3cccc(C(F)(F)F)n3)n2)CC1]

4-Chloro-6-(6-(trifluoromethyl)pyridin-2-yl)-N-(2-(trifluoromethyl)pyridin-4-yl)-1,3,5-triazine-2-amine (43 mg, 0.10 mmol) was dissolved in 5 mL of tetrahydrofuran, and 3,3-difluoropiperidine (15 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ10.80 (s, 1H), 8.59-8.70 (m, 3H), 8.32 (s, 1H), 8.11-8.13 (m, 1H), 7.93 (s, 1H), 4.01-4.11 (m, 4H), 2.15 (s, 4H). ES: m/z 506.1 [M+H]$^+$.

Example 2: 4-(3,3-Difluoropiperidin-1-yl)-6-(6-(trifluoromethyl)pyridin-2-yl)-N-(2-(trifluoromethyl)pyridin-4-yl)-1,3,5-triazin-2-amine

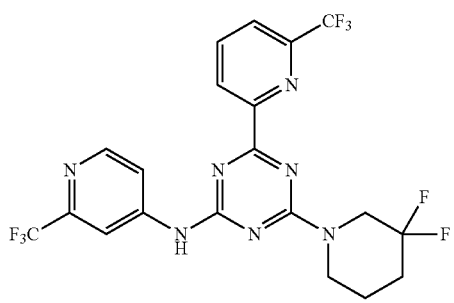 [SMILES: FC1(F)CCCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3,3-difluoropiperidine (15 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ10.69-10.71 (m, 1H), 8.58-8.68 (m, 3H), 8.30-8.35 (m, 1H), 8.11-8.13 (m, 1H), 7.89-7.98 (m, 1H), 4.19-4.33 (m, 1.5H), 3.63 (s, 1H), 3.31-3.49 (m, 1.5H), 1.86-1.95 (m, 2H), 1.54-1.56 (m, 2H). ES: m/z 506.1 [M+H]$^+$.

Example 3: 4-(3-Hydroxypiperidin-1-yl)-6-(6-(trifluoromethyl)pyridin-2-yl)-N-(2-(trifluoromethyl)pyridin-4-yl)-1,3,5-triazin-2-amine

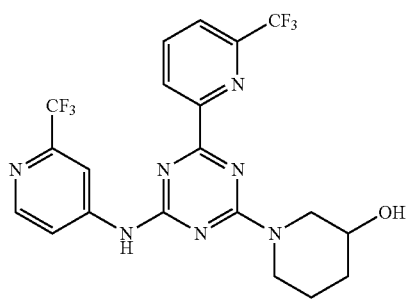 [SMILES: OC1CCCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3-hydroxypiperidine (12 mg, 0.12 mmol) and sodium carbonate (16 mg, 0.15 mmol) were added. The mixture was heated under reflux for 16 h. The resultant solution was filtered, and the filtrate was purified by column chromatography to give the title compound. ¹H NMR (500 MHz, DMSO-d₆): δ10.84 (s, 1H), 8.59-8.71 (m, 3H), 8.31-8.34 (m, 1H), 8.11-8.13 (m, 1H), 7.83-7.90 (m, 1H), 4.22-4.36 (m, 2H), 3.95-4.06 (m, 2H), 2.18-2.22 (m, 2H), 1.83 (s, 2H). ES: m/z 486.1 [M+H]⁺.

Example 4: 4-Morpholinyl-6-(6-(trifluoromethyl)pyridin-2-yl)-N-(2-(trifluoromethyl) pyridin-4-yl)-1,3,5-triazin-2-amine

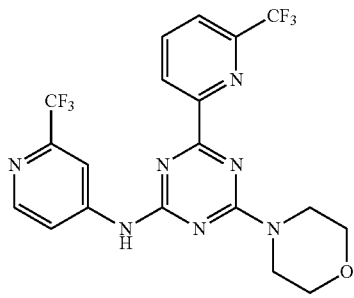 [SMILES: FC(F)(F)c1cc(Nc2nc(-c3cccc(C(F)(F)F)n3)nc(N3CCOCC3)n2)ccn1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and morpholine (10 mg, 0.12 mmol) and sodium carbonate (16 mg, 0.15 mmol) were added. The mixture was heated under reflux for 16 h. The resultant solution was filtered, and the filtrate was purified by column chromatography to give the title compound. ¹H NMR (500 MHz, DMSO-d₆): δ10.74 (s, 1H), 8.56-8.67 (m, 3H), 8.27-8.30 (m, 1H), 8.08-8.10 (m, 1H), 7.94 (s, 1H), 3.74-3.96 (m, 8H). ES: m/z 472.2 [M+H]⁺.

Example 5: 4-(Piperazin-1-yl)-6-(6-(trifluoromethyl)pyridin-2-yl)-N-(2-(trifluoromethyl) pyridin-4-yl)-1,3,5-triazin-2-amine

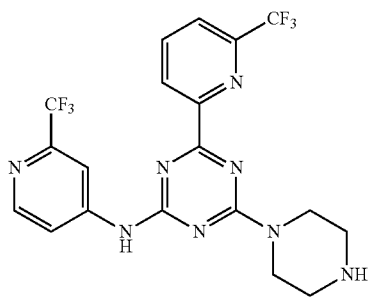 [SMILES: FC(F)(F)c1cc(Nc2nc(-c3cccc(C(F)(F)F)n3)nc(N3CCNCC3)n2)ccn1]

Step 1 Preparation of 4-(piperazin-4-carboxylic acid tert-butyl ester-1-yl)-6-(6-(trifluoromethyl)pyridin-2-yl)-N-(2-(trifluoromethyl)pyridin-4-yl)-1,3,5-triazin-2-amine

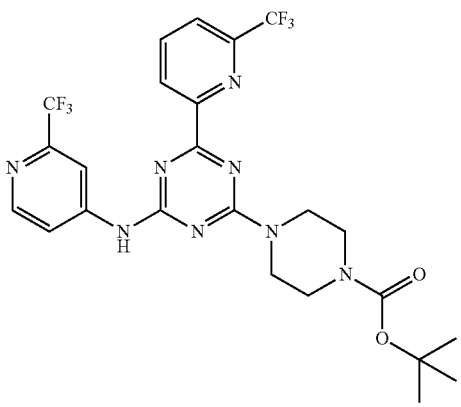 [SMILES: CC(C)(C)OC(=O)N1CCN(c2nc(Nc3ccnc(C(F)(F)F)c3)nc(-c3cccc(C(F)(F)F)n3)n2)CC1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and piperazine-1-carboxylic acid tert-butyl ester (22 mg, 0.12 mmol) and sodium carbonate (16 mg, 0.15 mmol) were added. The mixture was heated under reflux for 16 h. The resultant solution was filtered, and the filtrate was concentrated and dried to give the title compound.

Step 2 Preparation of 4-(piperazin-1-yl)-6-(6-(trifluoromethyl)pyridin-2-yl)-N-(2-(trifluoromethyl) pyridin-4-yl)-1,3,5-triazin-2-amine

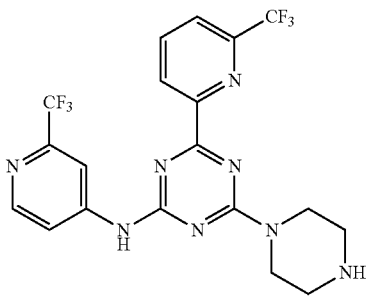 [SMILES: FC(F)(F)c1cc(Nc2nc(-c3cccc(C(F)(F)F)n3)nc(N3CCNCC3)n2)ccn1]

Tert-butyl 4-(4-(6-(trifluoromethyl)pyridin-2-yl)-(6-(2-(trifluoromethyl)pyridin-4-yl) amino)-1,3,5-triazin-2-yl) piperazine (45 mg, 0.08 mmol) was dissolved in 5 mL of dichloromethane, and 3 mL of trifluoroacetic acid was added. The mixture was stirred at room temperature for 12 h. The resultant solution was poured into water, and the pH was adjusted with saturated sodium hydrogen carbonate solution. The mixture was extracted with dichloromethane and dried over anhydrous sodium sulfate. The organic phase was concentrated to give a crude product, which was purified by column chromatography to give the title compound. ¹H NMR (500 MHz, DMSO-d₆): δ10.72 (br, 1H), 8.54-8.66 (m, 3H), 8.25-8.30 (m, 1H), 8.07-8.10 (m, 1H), 7.88-7.89 (m, 1H), 3.78-3.89 (m, 4H), 2.80 (s, 4H). ES: m/z 471.1 [M+H]⁺.

Example 6: 4-(4-Methylpiperazin-1-yl)-6-(6-(trifluoromethyl)pyridin-2-yl)-N-(2-(trifluoromethyl)pyridin-4-yl)-1,3,5-triazin-2-amine

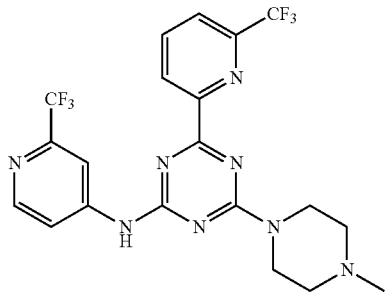 [SMILES: CN1CCN(c2nc(Nc3ccnc(C(F)(F)F)c3)nc(-c3cccc(C(F)(F)F)n3)n2)CC1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and N-methylpiperazine (12 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ10.75 (s, 1H), 8.59-8.70 (m, 3H), 8.30-8.33 (m, 1H), 8.12-8.13 (m, 1H), 7.92-7.93 (m, 1H), 3.90-4.00 (m, 4H), 2.48 (s, 4H), 2.28 (s, 3H). ES: m/z 485.2 [M+H]$^+$.

Example 7: 4-(3-(Trifluoromethyl)piperidin-1-yl)-6-(6-(trifluoromethyl)pyridin-2-yl)-N-(2-(trifluoromethyl) pyridin-4-yl)-1,3,5-triazin-2-amine

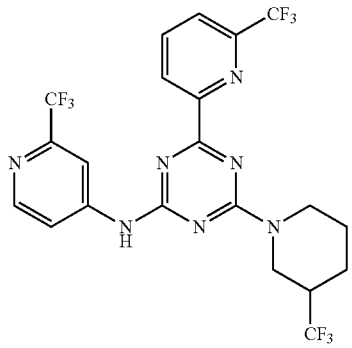 [SMILES: FC(F)(F)c1cc(Nc2nc(-c3cccc(C(F)(F)F)n3)nc(N3CCCC(C(F)(F)F)C3)n2)ccn1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3-trifluoromethylpiperidine (18 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ 10.76 (s, 1H), 8.52-8.64 (m, 3H), 8.26-8.30 (m, 1H), 8.08-8.09 (m, 1H), 7.86-7.87 (m, 1H), 4.48-4.92 (m, 2H), 3.11-3.24 (m, 2H), 2.61 (s, 1H), 2.01-2.02 (m, 1H), 1.83-1.85 (m, 1H), 1.57-1.65 (m, 2H). ES: m/z 538.2 [M+H]$^+$.

Example 8: 4-(1,2,4-Thiadiazol-1,1-dioxo-4-yl)-6-(6-(trifluoromethyl)pyridin-2-yl)-N-(2-(trifluoromethyl)pyridin-4-yl)-1,3,5-triazin-2-amine

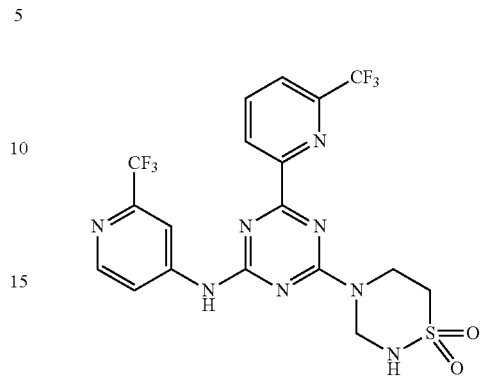

4-Chloro-6-(6-(trifluoromethyl)pyridinyl)N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and sulfonamide (16 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ 10.94 (s, 1H), 8.59-8.74 (m, 3H), 8.31-8.34 (m, 1H), 8.12-8.14 (m, 1H), 7.93 (s, 1H), 7.60-7.68 (m, 1H), 5.20-5.31 (m, 2H), 4.37-4.47 (m, 2H), 3.29 (s, 2H). ES: m/z 521.1 [M+H]$^+$.

Example 9: 4-((R)-3-hydroxypiperidin-1-yl)-6-(6-(trifluoromethyl)pyridin-2-yl)-N-(2-(trifluoromethyl)pyridin-4-yl)-1,3,5-triazin-2-amine

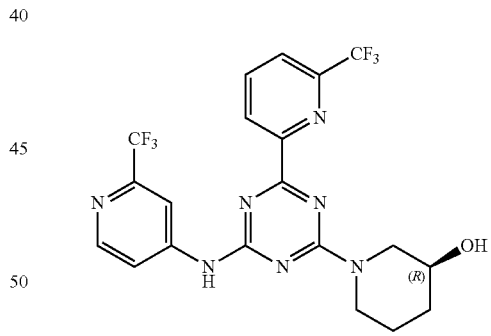

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (R)-3-hydroxypiperidine (12 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ 10.70 (br, 1H), 8.55-8.66 (m, 3H), 8.26-8.33 (m, 1H), 8.08-8.11 (m, 1H), 7.85-7.96 (m, 1H), 4.97-4.98 (m, 1H), 4.16-4.49 (m, 2H), 3.26-3.60 (m, 3H), 1.83-1.92 (m, 2H), 1.51-1.54 (m, 2H). ES: m/z 486.1 [M+H]$^+$.

Example 10: 4-((S)-3-hydroxypiperidin-1-yl)-6-(6-(trifluoromethyl)pyridin-2-yl)-N-(2-(trifluoromethyl)pyridin-4-yl)-1,3,5-triazin-2-amine

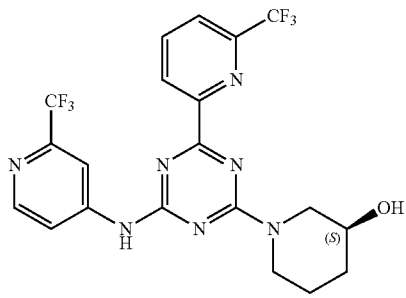

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (S)-3-hydroxypiperidine (12 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.70 (br, 1H), 8.55-8.66 (m, 3H), 8.26-8.33 (m, 1H), 8.08-8.11 (m, 1H), 7.85-7.96 (m, 1H), 4.97-4.98 (m, 1H), 4.16-4.49 (m, 2H), 3.26-3.60 (m, 3H), 1.83-1.92 (m, 2H), 1.51-1.54 (m, 2H). ES: m/z 486.1 [M+H]$^+$.

Example 11: 4-(3-Fluoropiperidin-1-yl)-6-(6-(trifluoromethyl)pyridin-2-yl)-N-(2-(trifluoromethyl)pyridin-4-yl)-1,3,5-triazin-2-amine

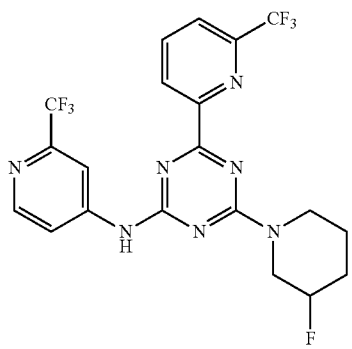 [SMILES: FC1CCCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3-fluoropiperidine (12 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.76 (s, 1H), 8.57-8.68 (m, 3H), 8.28-8.33 (m, 1H), 8.10-8.12 (m, 1H), 7.87-7.89 (m, 1H), 4.23-4.99 (m, 3H), 3.54-3.89 (m, 2H), 1.67-1.98 (m, 4H). ES: m/z 488.1 [M+H]$^+$.

Example 12

4-(3-Cyanopiperidin-1-yl)-6-(6-(trifluoromethyl)pyridin-2-yl)-N-(2-(trifluoromethyl)pyridin-4-yl)-1,3,5-triazin-2-amine

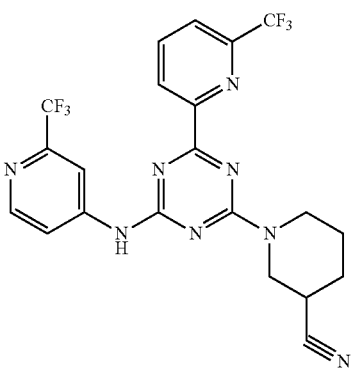 [SMILES: N#CC1CCCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3-cyanopiperidine (13 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.81 (s, 1H), 8.57-8.68 (m, 3H), 8.28-8.39 (m, 1H), 8.09-8.12 (m, 1H), 7.87 (s, 1H), 3.77-4.37 (m, 4H), 3.23 (s, 1H), 2.00 (s, 2H), 1.72 (s, 2H). ES: m/z 495.2 [M+H]$^+$.

Example 13: 4-(Piperidin-2-yl)-6-(6-(trifluoromethyl)pyridin-2-yl)-N-(2-(trifluoromethyl)pyridin-4-yl)-1,3,5-triazin-2-amine

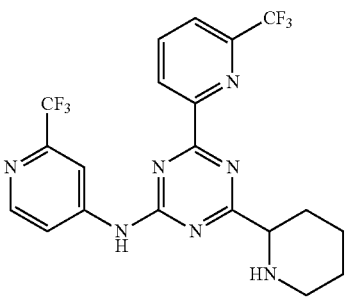 [SMILES: FC(F)(F)c1cc(Nc2nc(-c3cccc(C(F)(F)F)n3)nc(C3CCCCN3)n2)ccn1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of dioxane, and piperidin-2-boronic acid pinacol ester (21 mg, 0.10 mmol), 1,1'-bis-diphenylphosphinoferrocene palladium dichloride (7 mg, 0.01 mmol) and sodium carbonate (16 mg, 0.15 mmol) were added. The mixture was heated to react at 100° C. for 12 h. The resultant solution was filtered, and the filtrate was purified by column chromatography to give the title compound. $^1$H NMR (500 MHz, DMSO-d$_6$): δ 10.70 (s, 1H), 8.55-8.68 (m, 3H), 8.27-8.32

(m, 1H), 8.09-8.11 (m, 1H), 7.86-7.87 (m, 1H), 3.87-3.96 (m, 3H), 1.63-1.69 (m, 6H). ES: m/z 470.2 [M+H]⁺.

Example 14: 4-(3-Aminopiperidin-1-yl)-6-(6-(trifluoromethyl)pyridin-2-yl)-N-(2-(trifluoromethyl)pyridin-4-yl)-1,3,5-triazin-2-amine

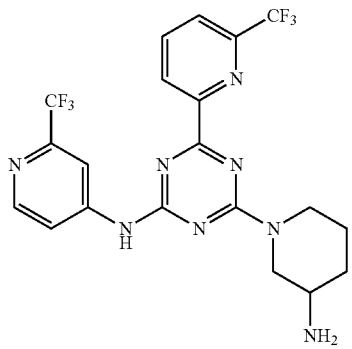 [SMILES: NC1CCCN(c2nc(Nc3ccnc(C(F)(F)F)c3)nc(-c3cccc(C(F)(F)F)n3)n2)C1]

Step 1 Preparation of tert-butyl (1-(4-(6-(trifluoromethyl)pyridin-2-yl)-(6-(2-(trifluoromethyl)pyridin-4-yl)amino)-1,3,5-triazin-2-yl)-3-piperidinyl)carbamate

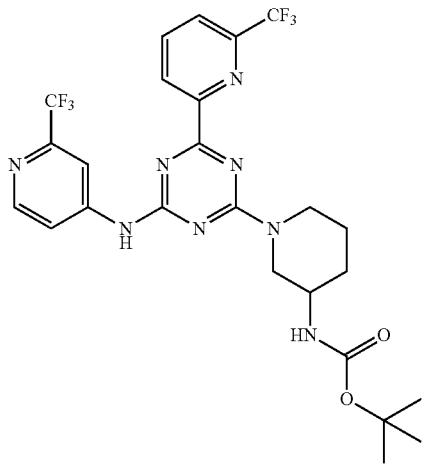 [SMILES: CC(C)(C)OC(=O)NC1CCCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and tert-butyl piperidin-3-carbamate (24 mg, 0.12 mmol) and sodium carbonate (16 mg, 0.15 mmol) were added. The mixture was heated under reflux for 16 h. The resultant solution was filtered, and the filtrate was concentrated and dried to give the title compound.

Step 2 Preparation of 4-(3-aminopiperidin-1-yl)-6-(6-(trifluoromethyl)pyridin-2-yl)-N-(2-(trifluoromethyl)pyridin-4-yl)-1,3,5-triazin-2-amine

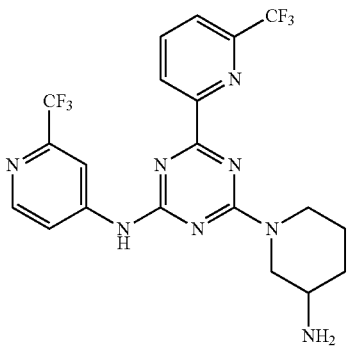 [SMILES: NC1CCCN(c2nc(Nc3ccnc(C(F)(F)F)c3)nc(-c3cccc(C(F)(F)F)n3)n2)C1]

Tert-butyl (1-(4-(6-(trifluoromethyl)pyridin-2-yl)-(6-(2-(trifluoromethyl)pyridin-4-yl) amino)-1,3,5-triazin-2-yl)-3-piperidinyl)carbamate (45 mg, 0.08 mmol) was dissolved in 5 mL of dichloromethane, and 3 mL of trifluoroacetic acid was added. The mixture was stirred at room temperature for 12 h. The resultant solution was poured into water, and the pH was adjusted with saturated sodium hydrogen carbonate solution. The mixture was extracted with dichloromethane and dried over anhydrous sodium sulfate. The organic phase was concentrated to give a crude product, which was purified by column chromatography to give the title compound. ¹H NMR (500 MHz, DMSO-d₆): δ 10.75-10.81 (m, 1H), 8.56-8.76 (m, 2H), 7.86-8.33 (m, 4H), 4.11-4.62 (m, 2H), 3.57-3.76 (m, 2H), 3.35 (s, 1H), 2.06 (s, 1H), 1.64-1.85 (m, 3H). ES: m/z 485.1 [M+H]⁺.

Example 15: 4-(3,3-Difluoropyrrolidin-1-yl)-6-(6-(trifluoromethyl)pyridin-2-yl)-N-(2-(trifluoromethyl)pyridin-4-yl)-1,3,5-triazin-2-amine

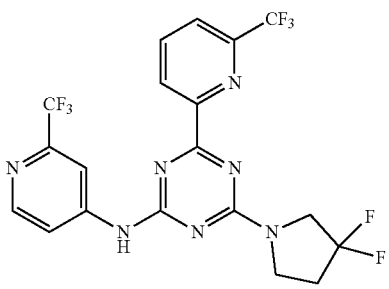 [SMILES: FC1(F)CCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3,3-difluoropyrrolidine (13 mg, 0.12 mmol) and sodium carbonate (16 mg, 0.15 mmol) were added. The mixture was heated under reflux for 16 h. The resultant solution was filtered, and the filtrate was purified by column chromatography to give the title compound. ¹H NMR (500 MHz, DMSO-d₆): δ 10.90 (s, 1H), 8.58-8.74 (m, 3H), 8.30-8.35 (m, 1H), 8.13-8.15 (m, 1H), 8.00-8.01 (m, 1H), 4.05-4.18 (m, 2H), 3.89-3.98 (m, 2H), 2.61-2.67 (m, 2H). ES: m/z 492.2 [M+H]⁺.

Example 16: 4-(3,4-Dihydroxypiperidin-1-yl)-6-(6-(trifluoromethyl)pyridin-2-yl)-N-(2-(trifluoromethyl)pyridin-4-yl)-1,3,5-triazin-2-amine

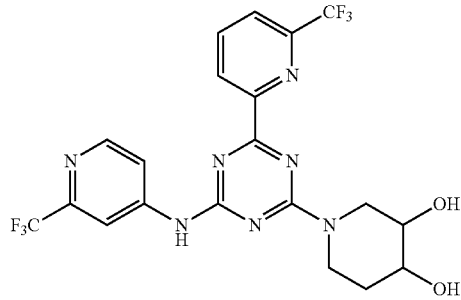 [SMILES: OC1CCN(c2nc(Nc3ccnc(C(F)(F)F)c3)nc(-c3cccc(C(F)(F)F)n3)n2)CC1O]

Step 1 Preparation of 3,4-dihydroxypiperidine

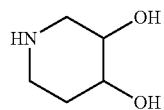

Tert-butyl 7-oxa-3-azabicyclo[4.1.0]heptane-3-carboxylate (100 mg, 0.50 mmol) was dissolved in 5 mL of dichloromethane, and 3 mL of trifluoroacetic acid was added. The mixture was stirred at room temperature for 12 h. The resultant solution was concentrated and dried to give the title compound.

Step 2 Preparation of 1-(4-(6-(trifluoromethyl)pyridin-2-yl)-(6-(2-(trifluoromethyl) pyridin-4-yl)amino)-1,3,5-triazin-2-yl)piperidin-3,4-diol

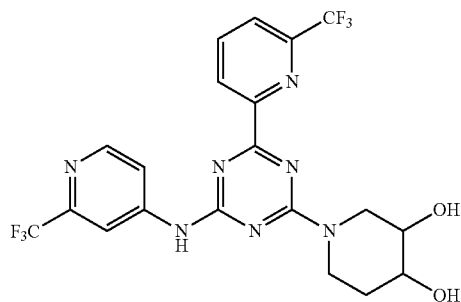 [SMILES: OC1CCN(c2nc(Nc3ccnc(C(F)(F)F)c3)nc(-c3cccc(C(F)(F)F)n3)n2)CC1O]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3,4-dihydroxypiperidine (14 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ 10.70 (br, 1H), 8.55-8.66 (m, 3H), 8.27-8.32 (m, 1H), 8.09-8.11 (m, 1H), 7.86-7.92 (m, 1H), 4.93-5.03 (m, 2H), 4.20-4.37 (m, 2H), 3.45-3.55 (m, 2H), 1.94-1.98 (m, 1H), 1.44-1.48 (m, 1H). ES: m/z 502.2 [M+H]$^+$.

Example 17: 4-((R)-3-hydroxypyrrolidin-1-yl)-6-(6-(trifluoromethyl)pyridin-2-yl)-N-(2-(trifluoromethyl)pyridin-4-yl)-1,3,5-triazin-2-amine

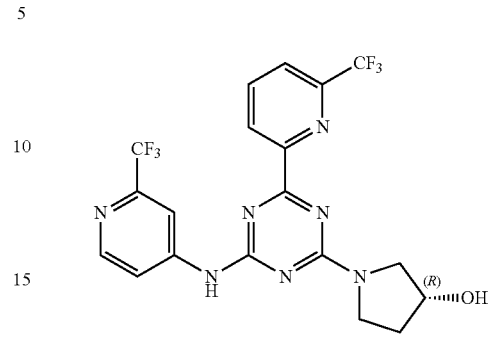

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (R)-3-hydroxypyrrolidine (10 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ 10.70 (s, 1H), 8.53-8.71 (m, 3H), 8.25-8.30 (m, 1H), 8.06-8.09 (m, 1H), 7.95 (s, 1H), 5.10 (br, 1H), 4.42-4.43 (m, 1H), 3.55-3.84 (m, 4H), 1.94-2.10 (m, 2H). ES: m/z 472.2 [M+H]$^+$.

Example 18: 4-((S)-3-hydroxypyrrolidin-1-yl)-6-(6-(trifluoromethyl)pyridin-2-yl)-N-(2-(trifluoromethyl)pyridin-4-yl)-1,3,5-triazin-2-amine

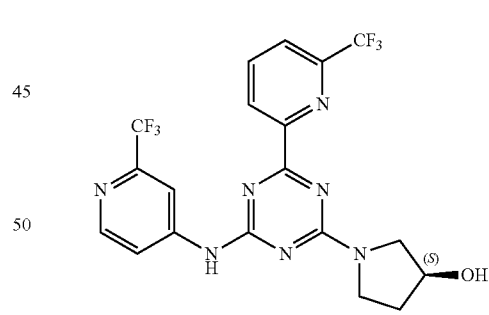

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (S)-3-hydroxypyrrolidine (10 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ 10.70 (s, 1H), 8.53-8.71 (m, 3H), 8.25-8.30 (m, 1H), 8.06-8.09 (m, 1H), 7.95 (s, 1H), 5.10 (br, 1H), 4.42-4.43 (m, 1H), 3.55-3.84 (m, 4H), 1.94-2.10 (m, 2H). ES: m/z 472.2 [M+H]$^+$.

Example 19: 4-(4-Fluoropiperidin-1-yl)-6-(6-(trifluoromethyl)pyridin-2-yl)-N-(2-(trifluoromethyl)pyridin-4-yl)-1,3,5-triazin-2-amine

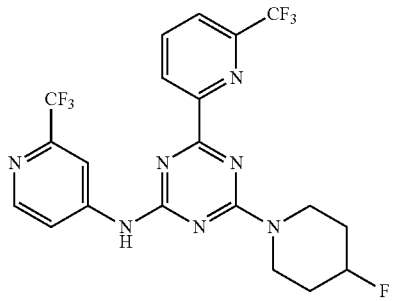 [SMILES: FC1CCN(c2nc(Nc3ccnc(C(F)(F)F)c3)nc(-c3cccc(C(F)(F)F)n3)n2)CC1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 4-fluoropiperidine (12 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ10.71 (s, 1H), 8.54-8.66 (m, 3H), 8.25-8.30 (m, 1H), 8.07-8.09 (m, 1H), 7.87-7.89 (m, 1H), 4.90-5.06 (m, 1H), 3.93-4.03 (m, 4H), 1.83-2.07 (m, 4H). ES: m/z 488.2 [M+H]$^+$.

Example 20: 4-(3-Fluoro-4,4-dihydroxypiperidin-1-yl)-6-(6-(trifluoromethyl)pyridin-2-yl)-N-(2-(trifluoromethyl)pyridin-4-yl)-1,3,5-triazin-2-amine

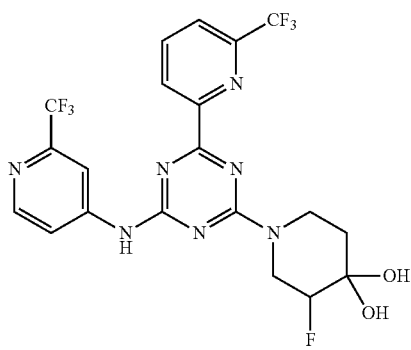 [SMILES: OC1(O)CCN(c2nc(Nc3ccnc(C(F)(F)F)c3)nc(-c3cccc(C(F)(F)F)n3)n2)CC1F]

Step 1 Preparation of 3-fluoro-4,4-dihydroxypiperidine

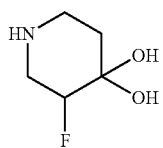

Tert-butyl 3-fluoro-4,4-dihydroxypiperidin-1-carboxylic acid (200 mg, 0.85 mmol) was dissolved in 5 mL dichloromethane, and 5 mL of trifluoroacetic acid was added. The mixture was stirred at room temperature for 12 h. The resultant solution was concentrated and dried to give the title compound.

Step 2 Preparation of 4-(3-Fluoro-4,4-dihydroxypiperidin-1-yl)-6-(6-(trifluoromethyl)pyridin-2-yl)-N-(2-(trifluoromethyl)pyridin-4-yl)-1,3,5-triazin-2-amine

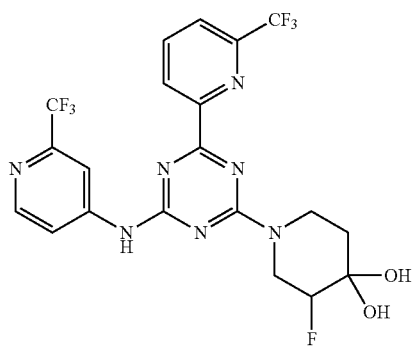 [SMILES: OC1(O)CCN(c2nc(Nc3ccnc(C(F)(F)F)c3)nc(-c3cccc(C(F)(F)F)n3)n2)CC1F]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3-fluoro-4,4-dihydroxypiperidine (16 mg, 0.12 mmol) prepared in step 1 of Example 20 and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ8.64-8.67 (m, 2H), 8.54-8.56 (m, 1H), 8.27-8.30 (m, 1H), 8.07-8.09 (m, 1H), 7.78-7.80 (m, 1H), 4.37-5.11 (m, 3H), 3.28-3.59 (m, 2H), 1.75-1.90 (m, 2H). ES: m/z 520.1 [M+H]$^+$.

Example 21: 4-(4-Trifluoromethyl-4-hydroxypiperidin-1-yl)-6-(6-(trifluoromethyl) pyridin-2-yl)-N-(2-(trifluoromethyl)pyridin-4-yl)-1,3,5-triazin-2-amine

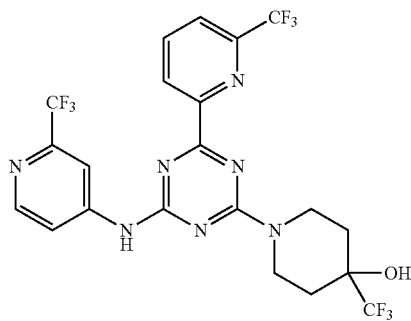 [SMILES: OC1(C(F)(F)F)CCN(c2nc(Nc3ccnc(C(F)(F)F)c3)nc(-c3cccc(C(F)(F)F)n3)n2)CC1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 4-(trifluoromethyl)piperidin-4-ol (20 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.74 (s, 1H), 8.54-8.67 (m, 3H), 8.25-8.30 (m, 1H), 8.07-8.09 (m, 1H), 7.85-7.88 (m, 1H), 6.21 (s, 1H), 4.87-4.91 (m, 1H), 4.62-4.66 (m, 1H), 3.25-3.32 (m, 2H), 1.73-1.86 (m, 4H). ES: m/z 554.2 [M+H]$^+$.

Example 22: 4-(3-Trifluoromethyl-3-hydroxypyrrolidin-1-yl)-6-(6-(trifluoromethyl)pyridin-2-yl)-N-(2-(trifluoromethyl)pyridin-4-yl)-1,3,5-triazin-2-amine

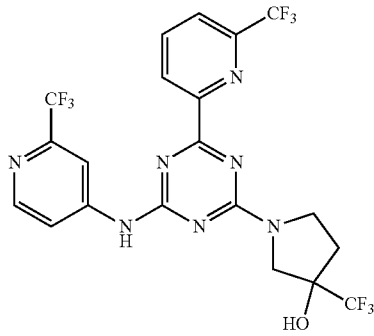 [SMILES: OC1(C(F)(F)F)CCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3-trifluoromethyl-pyrrolidin-3-ol (19 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.81 (s, 1H), 8.55-8.81 (m, 3H), 8.27-8.32 (m, 1H), 8.08-8.11 (m, 1H), 7.81-8.00 (m, 1H), 6.67 (s, 1H), 3.73-4.11 (m, 4H), 2.18-2.38 (m, 2H). ES: m/z 540.2 [M+H]$^+$.

Example 22A: (R)-4-(3-trifluoromethyl-3-hydroxypyrrolidin-1-yl)-6-(6-(trifluoromethyl) pyridin-2-yl)-N-(2-(trifluoromethyl)pyridin-4-yl)-1,3,5-triazin-2-amine

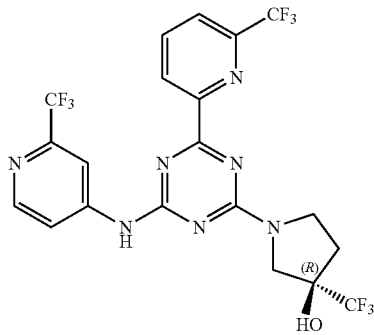

The product 4-(3-trifluoromethyl-3-hydroxypyrrolidin-1-yl)-6-(6-(trifluoromethyl) pyridin-2-yl)-N-(2-(trifluoromethyl)pyridin-4-yl)-1,3,5-triazin-2-amine (260 mg) prepared in Example 22 was dissolved in 30 mL of methanol for preparative separation. The preparative separation method was performed under conditions: instrument: MG II preparative SFC (SFC-1); preparative column: ChiralCel OD, 250×30 mm I.D., 5 m; mobile phase: A: CO$_2$, B: isopropanol (0.1% NH$_3$H$_2$O); gradient: B 30%; flow rate: 60 mL/min; pressure: 100 bar; column temperature: 38° C.; detection wavelength: 220 nm. After preparative separation, the first effluent was subjected to vacuum spin drying in a 40° C. water bath to give the title compound (115.4 mg, retention time 4.76 min), ee=99.6%, $^1$H NMR (500 MHz, DMSO-d$_6$): δ 10.81 (s, 1H), 8.55-8.81 (m, 3H), 8.27-8.32 (m, 1H), 8.08-8.11 (m, 1H), 7.81-8.00 (m, 1H), 6.67 (s, 1H), 3.73-4.11 (m, 4H), 2.18-2.38 (m, 2H), ES: m/z 540.2 [M+H]$^+$.

Example 22B: (S)-4-(3-trifluoromethyl-3-hydroxypyrrolidin-1-yl)-6-(6-(trifluoromethyl) pyridin-2-yl)-N-(2-(trifluoromethyl)pyridin-4-yl)-1,3,5-triazin-2-amine

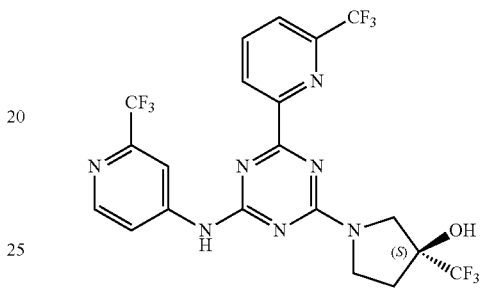

The product 4-(3-trifluoromethyl-3-hydroxypyrrolidin-1-yl)-6-(6-(trifluoromethyl)pyridin-2-yl)-N-(2-(trifluoromethyl)pyridin-4-yl)-1,3,5-triazin-2-amine (260 mg) prepared in Example 22 was dissolved in 30 mL of methanol for preparative separation. The preparative separation method was performed under conditions: instrument: MG II preparative SFC (SFC-1); preparative column: ChiralCel OD, 250×30 mm I.D., 5 am; mobile phase: A: CO$_2$, B: isopropanol (0.1% NH$_3$H$_2$O); gradient: B 30%; flow rate: 60 mL/min; pressure: 100 bar; column temperature: 38° C.; detection wavelength: 220 nm. After preparative separation, the first effluent was subjected to vacuum spin drying in a 40° C. water bath to give the title compound (135.0 mg, retention time 5.09 min), ee=99.7%, $^1$H NMR (500 MHz, DMSO-d$_6$): δ 10.81 (s, 1H), 8.55-8.81 (m, 3H), 8.27-8.32 (m, 1H), 8.08-8.11 (m, 1H), 7.81-8.00 (m, 1H), 6.67 (s, 1H), 3.73-4.11 (m, 4H), 2.18-2.38 (m, 2H), ES: m/z 540.2 [M+H]$^+$.

Example 23: 4-((3S,4S)-3-hydroxy-4-fluoropyrrolidin-1-yl)-6-(6-(trifluoromethyl) pyridin-2-yl)-N-(2-(trifluoromethyl)pyridin-4-yl)-1,3,5-triazin-2-amine

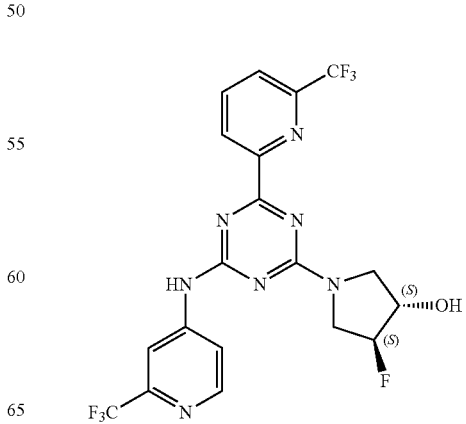

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (3S,4S)-4-fluoropyrrolidin-3-ol (13 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.79 (s, 1H), 8.56-8.70 (m, 3H), 8.28-8.33 (m, 1H), 8.09-8.11 (m, 1H), 7.97-8.02 (m, 1H), 5.68-5.72 (m, 1H), 5.06-5.27 (m, 1H), 4.43 (s, 1H), 3.77-4.07 (m, 4H). ES: m/z 490.2 [M+H]$^+$.

Example 24: 4-(Tetrahydropyrimidin-1(2H)-yl)-6-(6-(trifluoromethyl) pyridin-2-yl)-N-(2-(trifluoromethyl)pyridin-4-yl)-1,3,5-triazin-2-amine

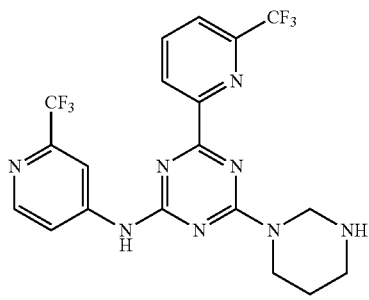 [SMILES: FC(F)(F)c1cc(Nc2nc(-c3cccc(C(F)(F)F)n3)nc(N3CCCNC3)n2)ccn1]

Step 1 Preparation of tert-butyl 3-(4-(6-(trifluoromethyl)pyridin-2-yl)-(6-(2-(trifluoromethyl)pyridin-4-yl)amino)-1,3,5-triazin-2-yl)tetrahydropyrimidin-1(2H)-carboxy late

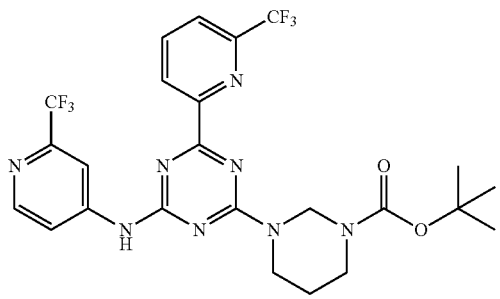 [SMILES: CC(C)(C)OC(=O)N1CCCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and tert-butyl tetrahydropyrimidin-1(2H)-carboxylic acid (22 mg, 0.12 mmol) and sodium carbonate (16 mg, 0.15 mmol) were added. The mixture was heated under reflux for 16 h. The resultant solution was filtered, and the filtrate was concentrated and dried to give the title compound.

Step 2 Preparation of 4-(tetrahydropyrimidin-1(2H)-yl)-6-(6-(trifluoromethyl) pyridin-2-yl)-N-(2-(trifluoromethyl)pyridin-4-yl)-1,3,5-triazin-2-amine

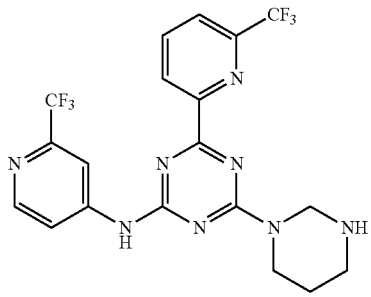 [SMILES: FC(F)(F)c1cc(Nc2nc(-c3cccc(C(F)(F)F)n3)nc(N3CCCNC3)n2)ccn1]

Tert-butyl 3-(4-(6-(trifluoromethyl)pyridin-2-yl)-(6-(2-(trifluoromethyl)pyridin-4-yl) amino)-1,3,5-triazin-2-yl)tetrahydropyrimidin-1(2H)-carboxylate (45 mg, 0.08 mmol) was dissolved in 5 mL of dichloromethane, and 3 mL of trifluoroacetic acid was added. The mixture was stirred at room temperature for 12 h. The resultant solution was poured into water, and the pH was adjusted with saturated sodium hydrogen carbonate solution. The mixture was extracted with dichloromethane and dried over anhydrous sodium sulfate. The organic phase was concentrated to give a crude product, which was purified by column chromatography to give the title compound. $^1$H NMR (500 MHz, DMSO-d$_6$): δ 10.98 (s, 1H), 9.14 (br, 1H), 8.54-9.12 (m, 3H), 8.28-8.36 (m, 1H), 8.08-8.15 (m, 1H), 7.92 (s, 1H), 5.16-5.31 (m, 2H), 4.04-4.15 (m, 2H), 3.33-3.51 (m, 2H), 1.89 (s, 2H). /z 471.1 [M+H]$^+$.

Example 25: 4-(4,4-Difluorocyclohexyl-1-en-1-yl)-6-(6-(trifluoromethyl) pyridin-2-yl)-N-(2-(trifluoromethyl)pyridin-4-yl)-1,3,5-triazin-2-amine

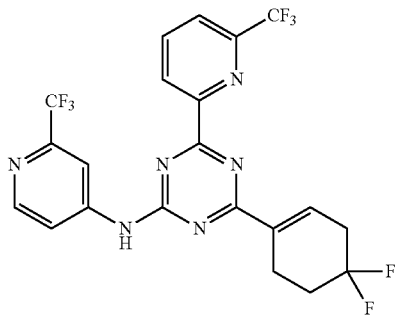 [SMILES: FC1(F)CC=C(c2nc(Nc3ccnc(C(F)(F)F)c3)nc(-c3cccc(C(F)(F)F)n3)n2)CC1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of dioxane, and 2-(4,4-difluorocyclohex-1-en-1-yl)-4,4,5,5-tetramethyl-1,3,2-dioxaborane (24.4 mg, 0.01 mmol), 1,1'-bis-diphenylphosphinoferrocene palladium dichloride (7 mg, 0.01 mmol) and sodium carbonate (16 mg, 0.15 mmol) were added. The mixture was heated to react at 100° C. for 12 h. The resultant solution was filtered, and the filtrate was purified by column chromatography to give the title compound. $^1$H NMR (500 MHz, DMSO-d$_6$): δ 10.68 (s, 1H), 8.54-8.71 (m, 3H), 8.15-8.28 (m, 1H), 7.82-8.10 (m, 1H), 7.85-7.87 (m, 1H), 5.93-6.05 (m, 1H), 1.85-2.34 (m, 6H). ES: m/z 503.1 [M+H]⁺.

Example 26: 4-(4,4-Difluorocyclohexyl)-6-(6-(trifluoromethyl)pyridin-2-yl)-N-(2-(trifluoromethyl)pyridin-4-yl)-1,3,5-triazin-2-amine

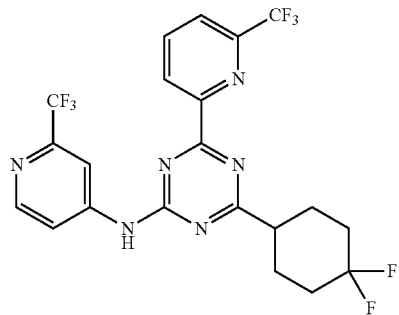 [SMILES: FC1(F)CCC(c2nc(Nc3ccnc(C(F)(F)F)c3)nc(-c3cccc(C(F)(F)F)n3)n2)CC1]

4-(4,4-Difluorocyclohexyl-1-en-1-yl)-6-(6-(trifluoromethyl)pyridin-2-yl)-N-(2-(trifluoromethyl)pyridin-4-yl)-1,3,5-triazin-2-amine (15 mg, 0.03 mmol) prepared in Example 25 was dissolved in 5 mL of methanol, and 10 mg of 10% palladium carbon was added. The mixture was hydrogenated at normal temperature and pressure for 2 h. The resultant solution was filtered, and the filtrate was purified by column chromatography to give the title compound. ¹H NMR (500 MHz, DMSO-d₆): δ 10.68 (s, 1H), 8.54-8.71 (m, 3H), 8.15-8.28 (m, 1H), 7.82-8.10 (m, 1H), 7.85-7.87 (m, 1H), 2.65-2.73 (m, 1H), 1.61-2.30 (m, 8H). ES: m/z 505.2 [M+H]⁺.

Example 27: 6-(6-(Trifluoromethoxy)pyridin-2-yl)-N²-(2-(trifluoromethoxy) pyridin-4-yl)-N⁴-(isopropoxy)-1,3,5-triazin-2,4-diamine

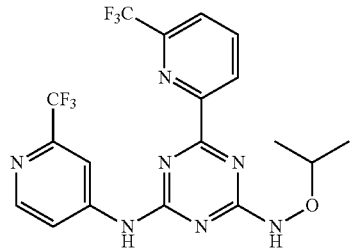 [SMILES: CC(C)ONc1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (430 mg, 1.02 mmol) prepared in step 4 of Example 1 was dissolved in 10 mL of tetrahydrofuran, and 2-(aminooxy)propane hydrochloride (136 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. ¹H NMR (300 MHz, DMSO-d₆): δ 11.28 (s, 1H), 10.81 (s, 1H), 8.65 (s, 1H), 8.58 (d, 2H), 8.33 (t, 1H), 8.12 (d, 1H), 8.05 (d, 1H), 4.23-4.15 (d, 1H), 1.27 (d, 6H). ES: m/z 460.1 [M+H]⁺.

Example 28: 4-(Tert-Butoxyamino)-6-(6-(trifluoromethyl)pyridin-2-yl)-N-(2-(trifluoromethyl)pyridin-4-yl)-1,3,5-triazin-2-amine

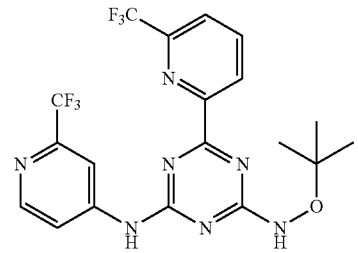 [SMILES: CC(C)(C)ONc1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and O-tert-butyl hydroxyamine hydrochloride (153 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. ¹H NMR (300 MHz, DMSO-d₆): δ 10.95 (s, 1H), 10.81 (s, 1H), 8.72 (s, 1H), 8.59 (d, 2H), 8.33 (t, 1H), 8.12 (d, 1H), 8.05 (d, 1H), 1.31 (s, 9H). ES: m/z 474.1 [M+H]⁺.

Example 29: 4-(2,2-Dimethylindenyl)-6-(6-(trifluoromethyl)pyridin-2-yl)-N-(2-(trifluoromethyl)pyridin-4-yl)-1,3,5-triazin-2-amine

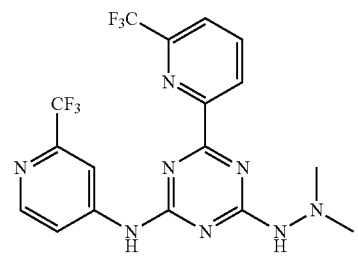 [SMILES: CN(C)Nc1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and 1,1-dimethylhydrazine hydrochloride (117.8 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. ¹H NMR (300 MHz, DMSO-d₆): δ 10.84 (s, 1H), 9.35 (s, 1H), 8.90 (s, 1H), 8.56 (d, 2H), 8.32 (t, 1H), 8.11 (d, 1H), 7.94 (d, 1H), 2.62 (s, 6H). ES: m/z 445.1 [M+H]⁺.

Example 30: N²-morpholinyl-6-(6-(trifluoromethyl)pyridin-2-yl)-N⁴-(2-(trifluoromethyl) pyridin-4-yl)-1,3,5-triazin-2-amine

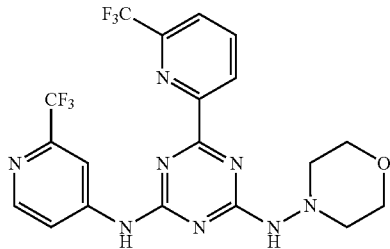 [SMILES: FC(F)(F)c1cc(Nc2nc(NN3CCOCC3)nc(-c3cccc(C(F)(F)F)n3)n2)ccn1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and 4-aminomorpholine (124.4 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-d$_6$): δ 10.79 (s, 1H), 9.50 (s, 1H), 8.87 (s, 1H), 8.56 (d, 2H), 8.35-8.30 (t, 1H)), 8.12 (d, 1H), 7.98 (d, 1H), 3.72 (m, 4H), 2.89 (s, 4H). ES: m/z 487.1 [M+H]$^+$.

Example 31: 1-(Ethyl(4-(6-(trifluoromethyl)pyridin-2-yl)-6-((2-(trifluoromethyl) pyridin-4-yl)amino)-1,3,5-triazin-2-yl)amino)-2-methylpropan-2-ol

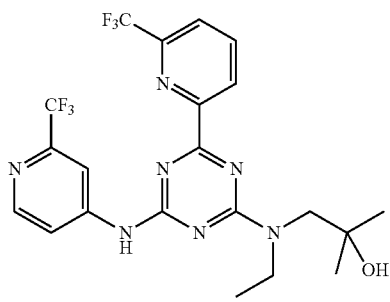 [SMILES: CCN(CC(C)(C)O)c1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and 1-ethylamino-2-methylisopropanol (142.7 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-d$_6$): δ 10.78 (s, 1H), 8.75 (s, 1H), 8.56 (d, 2H), 8.32 (t, 1H), 8.11 (d, 1H), 7.95 (d, 1H), 4.59 (s, 1H), 3.80-3.74 (m, 4H), 1.17-1.15 (m, 9H). ES: m/z 502.1 [M+H]$^+$.

Example 32: 1-(4-(6-(Trifluoromethyl)pyridin-2-yl)-6-(2-(trifluoromethyl)pyridin-4-yl-1,3,5-triazin-2-yl))azetidin-3-ol

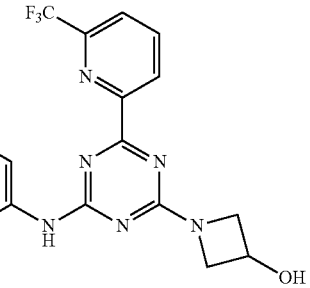

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and azetidin-3-ol hydrochloride (133.6 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-d$_6$): δ 10.79 (s, 1H), 8.77 (d, 1H), 8.61 (d, 1H), 8.56 (d, 1H), 8.31 (t, 1H), 8.12 (d, 1H), 7.92 (d, 1H), 5.88-5.87 (m, 1H), 4.67-4.64 (m, 1H), 4.48-4.41 (m, 2H), 3.98-3.95 (m, 2H). ES: m/z 458.1 [M+H]$^+$.

Example 33: 3-Methyl-1-(4-(6-(trifluoromethyl)pyridin-2-yl)-6-(2-(trifluoromethyl)pyridin-4-yl-1,3,5-triazin-2-yl))azetidin-3-ol

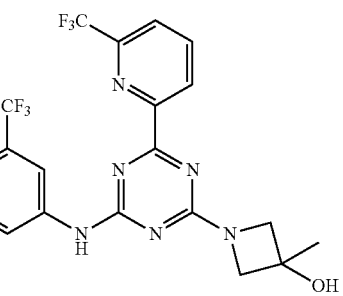

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was dissolved in 10 mL of tetrahydrofuran, and 3-methyl azetidin-3-ol hydrochloride (150.7 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-d$_6$): δ 10.77 (s, 1H), 8.74 (s, 1H), 8.61 (d, 1H), 8.56 (d, 1H), 8.31 (t, 1H), 8.11 (d, 1H), 7.94 (d, 1H), 5.80 (s, 1H) 4.15-4.05 (m, 4H), 1.49 (s, 3H). ES: m/z 472.1 [M+H]$^+$.

Example 34: 3-Trifluoromethyl-1-(4-(6-(trifluoromethyl)pyridin-2-yl)-6-(2-(trifluoromethyl) pyridin-4-yl-1,3,5-triazin-2-yl))azetidin-3-ol

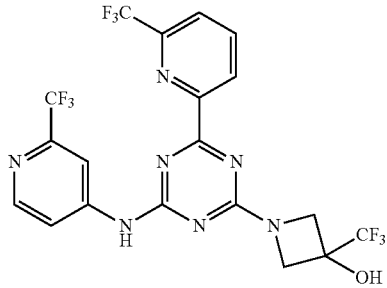 [SMILES: OC1(C(F)(F)F)CN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and 3-trifluoromethyl azetidin-3-ol hydrochloride (143 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-d$_6$): δ 10.89 (s, 1H), 8.66 (d, 2H), 8.58 (d, 1H), 8.33 (t, 1H), 8.12 (d, 1H), 7.99 (d, 1H), 7.60 (s, 1H), 4.50 (d, 2H), 4.27 (d, 2H). ES: m/z 526.1 [M+H]$^+$.

Example 35: 4-(3,3-Difluoroazetidin-1-yl)-6-(6-(trifluoromethyl)pyridin-2-yl)-N-(2-(trifluoromethyl)pyridin-4-yl)-1,3,5-triazin-2-amine

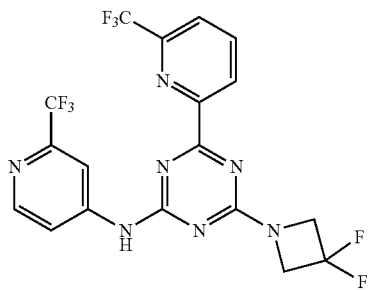 [SMILES: FC1(F)CN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and 3,3-difluoroazetidine hydrochloride (158 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-d$_6$): δ 10.89 (s, 1H), 8.65 (d, 2H), 8.58 (d, 1H), 8.34 (t, 1H), 8.13 (d, 1H), 7.80 (d, 1H), 4.26 (d, 2H), 4.12 (d, 2H). ES: m/z 478.1 [M+H]$^+$.

Example 36: (3R,4R)-1-(4-(6-(trifluoromethyl)pyridin-2-yl)-6-((2-(trifluoromethyl) pyridine-4-yl)amino)-1,3,5-triazin-2-yl)pyrrolidin-3,4-diol

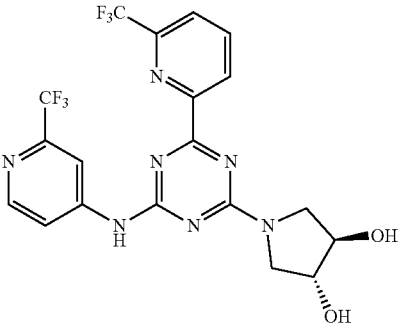 [SMILES: O[C@@H]1CN(c2nc(Nc3ccnc(C(F)(F)F)c3)nc(-c3cccc(C(F)(F)F)n3)n2)C[C@H]1O]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and (3R,4R)-pyrrolidin-3,4-diol (126 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-d$_6$): δ 10.89 (s, 1H), 8.64 (d, 2H), 8.57 (d, 1H), 8.31 (t, 1H), 8.11 (d, 1H), 7.99 (d, 1H), 5.11 (s, 2H), 3.55-3.38 (m, 6H). ES: m/z 488.1 [M+H]$^+$.

Example 37: (R)-2-(1-(4-(6-(trifluoromethyl)pyridin-2-yl)-6-((2-(trifluoromethyl) pyridin-4-yl)amino)-1,3,5-triazin-2-yl)pyrrolidin-2-yl)isopropan-2-ol

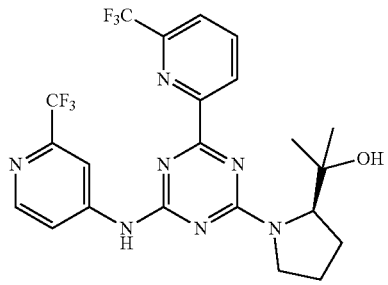 [SMILES: CC(C)(O)[C@H]1CCCN1c1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and D-valine methyl ester hydrochloride (201.2 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give intermediate (4-(6-(trifluoromethyl)pyridin-2-yl)-6-((2-(trifluoromethyl)pyridin-4-yl)amino)-1,3,5-triazin-2-yl)-D-valine methyl ester.

The intermediate (4-(6-(trifluoromethyl)pyridin-2-yl)-6-((2-(trifluoromethyl)pyridin-4-yl)amino)-1,3,5-triazin-2-yl)-D-valine methyl ester was added to 10 mL of tetrahydrofuran and the temperature was lowered to 0° C. 3 mL of methyl magnesium bromide solution (1 M) was added and stirred for 1 h. Then, the temperature was rinsed to room temperature and the stirring was continued for 1 hour. Silica gel was added to the resultant solution to make a mixture for chromatography. The resultant mixture was purified by column chromatography to give the title compound. $^1$H NMR (300 MHz, DMSO-$d_6$): δ 10.89 (s, 1H), 8.65 (d, 2H), 8.58 (d, 1H), 8.32 (t, 1H), 8.12 (d, 1H), 7.98 (d, 1H), 4.69 (s, 1H), 3.31-3.32 (m, 2H), 3.11 (t, 1H), 1.64-1.58 (m, 4H), 1.33 (s, 6H). ES: m/z 514.2 [M+H]$^+$.

Example 38: 4-(Trifluoromethyl)-1-(4-(6-(trifluoromethyl)pyridin-2-yl)-6-((2-(trifluoromethyl)pyridin-4-yl)amino)-1,3,5-triazin-2-yl)piperidin-4-ol

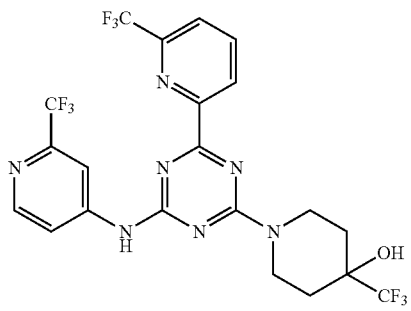

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and 4-(trifluoromethyl)piperidin-4-ol hydrochloride (250 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-$d_6$): δ 10.89 (s, 1H), 8.65 (d, 2H), 8.58 (d, 1H), 8.32 (t, 1H), 8.12 (d, 1H), 7.98 (d, 1H), 7.59 (s, 1H), 3.31-3.26 (m, 4H), 1.86-1.70 (m, 4H). ES: m/z 554.1 [M+H]$^+$.

Example 39: 2-Methyl-4-(4-(6-(trifluoromethyl)pyridin-2-yl)-6-((2-(trifluoromethyl)pyridin-4-yl)amino)-1,3,5-triazin-2-yl)-3-butyn-2-ol

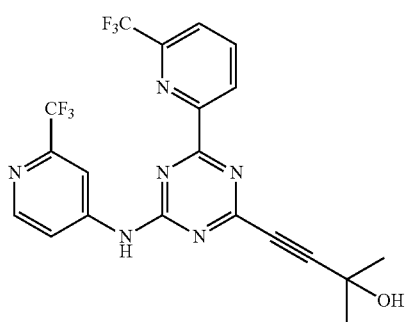 [SMILES: CC(C)(O)C#Cc1nc(Nc2ccnc(C(F)(F)F)c2)nc(-c2cccc(C(F)(F)F)n2)n1]

4-Chloro-6-(6-(trifluoromethyl)pyridin-2-yl)-N-(2-trifluoromethyl)pyridin-4-yl)-1,3,5-triazin-2-amine (1.0 g, 2.37 mmol) prepared in step 4 of Example 1 was added to 30 mL of tetrahydrofuran, and 2-methyl-3-butyn-2-ol (240 mg, 2.85 mmol), tetra(triphenylphosphine)palladium (275 mg, 0.237 mmol), cuprous iodide (45 mg, 0.237 mmol) and N,N-diisopropylethylamine (768 mg, 2.5 mmol) were added sequentially. The temperature was rinsed to 40° C. under argon to react for 5 h, and then cooled to room temperature. 30 mL of water was added to the resultant solution to quench the reaction. The mixture was extracted with ethyl acetate (30 mL×3), dried over anhydrous sodium sulfate, concentrated to make a mixture for chromatography, and then purified by column chromatography to give the title compound. $^1$H NMR (300 MHz, DMSO-$d_6$): δ 11.44 (s, 1H), 8.71 (d, 1H), 8.65 (d, 1H), 8.37 (t, 1H), 8.19 (d, 1H), 7.94 (d, 1H), 7.50 (d, 1H), 5.86 (s, 1H), 1.54 (s, 6H). ES: m/z 469.0 [M+H]$^+$.

Example 40: 2-Methyl-4-(4-(6-(trifluoromethyl)pyridin-2-yl)-6-((2-(trifluoromethyl)pyridin-4-yl)amino)-1,3,5-triazin-2-yl)-3-buten-2-ol

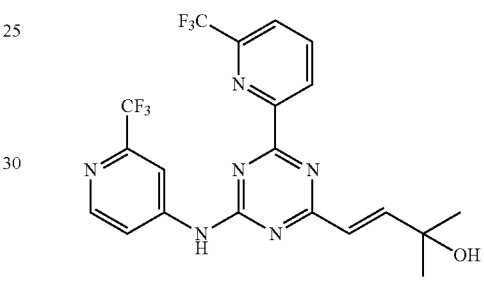

The compound 2-methyl-4-(4-(6-(trifluoromethyl)pyridin-2-yl)-6-((2-(trifluoromethyl) pyridin-4-yl)amino)-1,3,5-triazin-2-yl)-3-butyn-2-ol (468 mg, 1 mmol) prepared in Example 39 was dissolved in 15 mL of methanol, followed by addition of 100 mg of Pd/CaCO$_3$, and then subjected to a displacement with hydrogen for three times, and reacted at room temperature for 2 h. Silica gel was added to make a mixture for chromatography and the resultant mixture was purified by column chromatography to give the title compound. $^1$H NMR (300 MHz, DMSO-$d_6$): δ 11.35 (s, 1H), 8.83 (d, 1H), 8.68 (d, 1H), 8.35 (t, 1H), 8.18 (d, 1H), 7.94 (d, 1H), 7.50 (d, 1H), 6.81 (d, 1H), 6.66 (d, 1H), 4.35 (s, 1H), 1.48 (s, 6H). ES: m/z 471.1 [M+H]$^+$.

Example 41: 2-Methyl-4-(4-(6-(trifluoromethyl)pyridin-2-yl)-6-((2-(trifluoromethyl)pyridin-4-yl)amino)-1,3,5-triazin-2-yl)-3-butan-2-ol

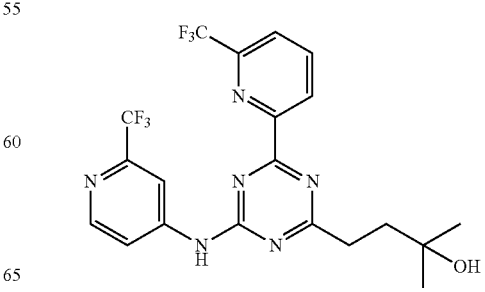

The compound 2-methyl-4-(4-(6-(trifluoromethyl)pyridin-2-yl)-6-((2-(trifluoromethyl) pyridin-4-yl)amino)-1,3,5-triazin-2-yl)-3-butyn-2-ol (410 mg, 0.88 mmol) prepared in example 39 was added to 15 mL of methanol, followed by addition of 10% Pd/C (94 mg, 0.088 mmol), and then reacted at room temperature under a hydrogen atmosphere overnight. The resultant solution was filtered by suction, and silica gel was added to the filtrate to make a mixture for chromatography. The resultant mixture was purified by column chromatography to give the title compound. $^1$H NMR (300 MHz, DMSO-$d_6$): δ 11.24 (s, 1H), 8.80 (s, 1H), 8.73 (d, 1H), 8.62 (d, 1H), 8.36 (t, 1H), 8.17 (d, 1H), 7.96 (d, 1H), 4.35 (s, 1H), 2.96 (t, 2H), 1.96 (t, 2H), 1.19 (s, 6H). ES: m/z 473.1 [M+H]$^+$.

Example 42: 4-Isopropoxy-6-(6-(trifluoromethyl) pyridin-2-yl)-N-(2-(trifluoromethyl) pyridin-4-yl)-1,3,5-triazin-2-amine

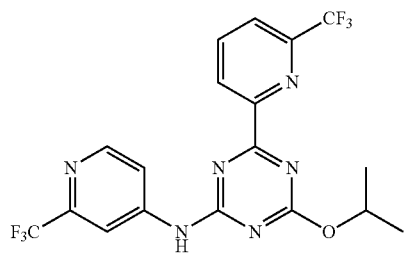 [SMILES: CC(C)Oc1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, stirred and dissolved to prepare a solution 1. To another reaction flask, isopropanol (91 mg, 1.5 mmol) and 5 mL of tetrahydrofuran were added, and the temperature was cooled to 0° C. 60% NaH (200 mg, 5 mmol) was added in batches, and stirred for 10 min after the addition. The solution 1 was slowly dropwise added to the mixture, and reaction was carried out at 0° C. for 1 h with an addition at room temperature for 1 h. After the reaction was completed, 1 g of crushed ice was slowly added to quench the reaction. Silica gel was added to the resultant solution to make a mixture for chromatography and then purified by column chromatography to give the title compound. $^1$H NMR (300 MHz, DMSO-$d_6$): δ 11.21 (s, 1H), 8.65 (t, 3H), 8.35 (t, 1H), 8.15 (d, 1H), 7.97 (d, 1H), 5.46-5.38 (m, 1H), 1.14 (s, 6H). ES: m/z 445.1 [M+H]$^+$.

Example 43: 4-(2,2,2-Trifluoroethoxy)-6-(6-(trifluoromethyl)pyridin-2-yl)-N-(2-(trifluoromethyl)pyridin-4-yl)-1,3,5-triazin-2-amine

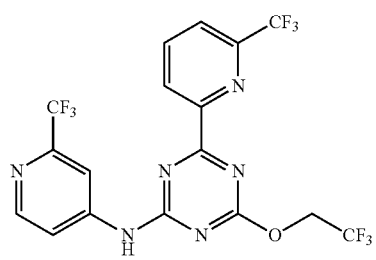 [SMILES: FC(F)(F)COc1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, stirred and dissolved to prepare a solution 1. To another reaction flask, trifluoroethanol (150 mg, 1.5 mmol) and 5 mL of tetrahydrofuran were added, and the temperature was cooled to 0° C. 60% NaH (200 mg, 5 mmol) was added in batches, and stirred for 10 min after the addition. The solution 1 was slowly dropwise added to the mixture, and reaction was carried out at 0° C. for 1 h with an addition at room temperature for 1 h. After the reaction was completed, 1 g of crushed ice was slowly added to quench the reaction. Silica gel was added to the resultant solution to make a mixture for chromatography and then purified by column chromatography to give the title compound. $^1$H NMR (300 MHz, DMSO-$d_6$): δ 11.41 (s, 1H), 8.78 (d, 2H), 8.66 (d, 1H), 8.37 (t, 1H), 8.18 (d, 1H), 7.99 (s, 1H), 5.28-5.23 (m, 2H). ES: m/z 485.1 [M+H]$^+$.

Example 44: 4-(6-(Trifluoromethyl)pyridin-2-yl)-N-(2-(trifluoromethyl)pyridin-4-yl)-6-((1,1,1-trifluoroisopropyl-2-yl)oxy)-1,3,5-triazin-2-amine

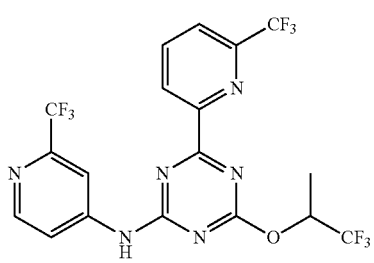 [SMILES: CC(Oc1nc(Nc2ccnc(C(F)(F)F)c2)nc(-c2cccc(C(F)(F)F)n2)n1)C(F)(F)F]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, stirred and dissolved to prepare a solution 1. To another reaction flask, trifluoroisopropanol (171 mg, 1.5 mmol) and 5 mL of tetrahydrofuran were added, and the temperature was cooled to 0° C. 60% NaH (200 mg, 5 mmol) was added in batches, and stirred for 10 min after the addition. The solution 1 was slowly dropwise added to the mixture, and reaction was carried out at 0° C. for 1 h with an addition at room temperature for 1 h. After the reaction was completed, 1 g of crushed ice was slowly added to quench the reaction. Silica gel was added to the resultant solution to make a mixture for chromatography and then purified by column chromatography to give the title compound. $^1$HNMR (300 MHz, DMSO-$d_6$): δ 11.41 (s, 1H), 8.78 (d, 2H), 8.66 (d, 1H), 8.37 (t, 1H), 8.18 (d, 1H), 7.99 (s, 1H), 5.77-5.81 (m, 1H), 1.48 (d, 3H). ES: m/z 499.1 [M+H]$^+$.

Example 45: 4-(2,2,3,3,3-pentafluoropropoxy)-6-(6-(trifluoromethyl) pyridin-2-yl)-N-(2-(trifluoromethyl) pyridin-4-yl)-1,3,5-triazin-2-amine

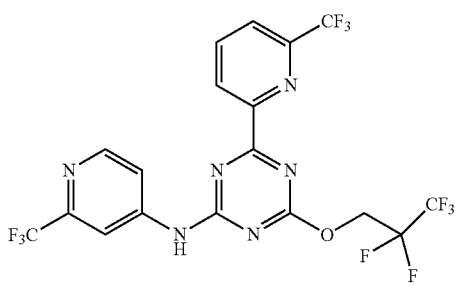 [SMILES: FC(F)(F)c1cc(Nc2nc(OCC(F)(F)C(F)(F)F)nc(-c3cccc(C(F)(F)F)n3)n2)ccn1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, stirred and dissolved to prepare a solution 1. To another reaction flask, pentafluoropropanol (225 mg, 1.5 mmol) and 5 mL of tetrahydrofuran were added, and the temperature was cooled to 0° C. 60% NaH (200 mg, 5 mmol) was added in batches, and stirred for 10 min after the addition. The solution 1 was slowly dropwise added to the mixture, and reaction was carried out at 0° C. for 1 h with an addition at room temperature for 1 h. After the reaction was completed, 1 g of crushed ice was slowly added to quench the reaction. Silica gel was added to the resultant solution to make a mixture for chromatography and then purified by column chromatography to give the title compound. $^1$HNMR (300 MHz, DMSO-$d_6$): δ 11.41 (s, 1H), 8.78 (d, 2H), 8.65 (d, 1H), 8.36 (t, 1H), 8.18 (d, 1H), 7.99 (s, 1H), 5.22-5.16 (m, 2H). ES: m/z 535.1 [M+H]$^+$.

Example 46: 4-(Pyrrolidin-2-one-1-yl)-6-(6-(trifluoromethyl)pyridin-2-yl)-N-(2-(trifluoromethyl) pyridine-4-yl)-1,3,5-triazin-2-amine

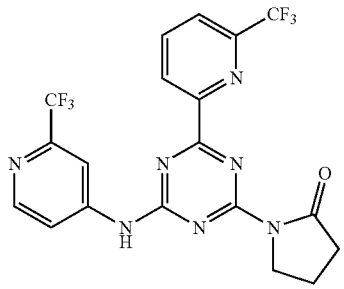 [SMILES: O=C1CCCN1c1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of dioxane, and 2-pyrrolidone (8.5 mg, 0.10 mmol), 1,1'-bis-diphenylphosphinoferrocene palladium dichloride (7 mg, 0.01 mmol), potassium acetate (15 mg, 0.15 mmol) were added. The mixture was heated to react at 100° C. for 12 h. The resultant solution was filtered, and the filtrate was purified by column chromatography to give the title compound. $^1$H NMR (500 MHz, DMSO-$d_6$): δ 10.82 (s, 1H), 8.51-8.65 (m, 3H), 8.27-8.32 (m, 1H), 8.08-8.11 (m, 1H), 7.95-8.00 (m, 1H), 3.70-3.85 (m, 2H), 2.25-2.41 (m, 2H), 1.86-2.01 (m, 2H). ES: m/z 470.1 [M+H]$^+$.

Example 47: 4-(2-(2-Propyl-2-ol)aziridin-1-yl)-6-(6-(trifluoromethyl)pyridin-2-yl)-N-(2-(trifluoromethyl)pyridin-4-yl)-1,3,5-triazin-2-amine

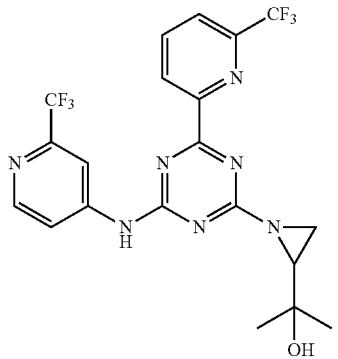 [SMILES: CC(C)(O)C1CN1c1nc(Nc2ccnc(C(F)(F)F)c2)nc(-c2cccc(C(F)(F)F)n2)n1]

Step 1 Preparation of 2-(1-tritylmethylaziridin-2-yl)propan-2-ol

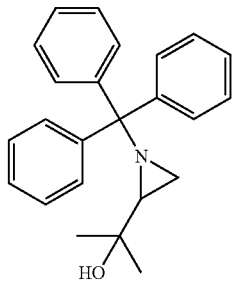 [SMILES: CC(C)(O)C1CN1C(c1ccccc1)(c1ccccc1)c1ccccc1]

Methyl 1-trityl aziridine-2-carboxylate (500 mg, 1.45 mmol) was dissolved in 10 mL of tetrahydrofuran, and methyllithium (2.91 mL, 2.91 mmol, 1 mol/L in THF) was added. The resultant was stirred at room temperature for 12 h, and then concentrated until dry to give the title compound.

Step 2 Preparation of 2-(azetidin-2-yl)propan-2-ol

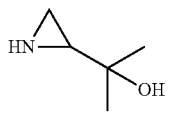

The 2-(1-tritylmethylaziridin-2-yl)propan-2-ol (100 mg, 0.29 mmol) was dissolved in 5 mL of dichloromethane, and 5 mL of trifluoroacetic acid was added. The resultant was stirred at room temperature for 12 h, and then concentrated until dry to give the title compound.

Step 3 Preparation of 4-(2-(2-propyl-2-ol)aziridin-1-yl)-6-(6-(trifluoromethyl) pyridin-2-yl)-N-(2-(trifluoromethyl)pyridin-4-yl)-1,3,5-triazin-2-amine

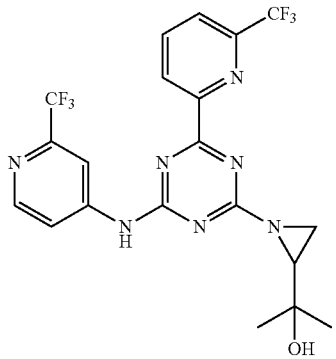 [SMILES: CC(C)(O)C1CN1c1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 2-(aziridin-2-yl)propan-2-ol (12 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.71 (br, 1H), 8.53-8.75 (m, 3H), 8.23-8.30 (m, 1H), 8.07-8.11 (m, 1H), 7.92-7.95 (m, 1H), 4.58 (s, 1H), 4.07-4.23 (m, 3H), 1.18 (s, 6H). ES: m/z 486.2 [M+H]$^+$.

Example 48: 4-(3-(2-propyl-2-ol)azetidin-1-yl)-6-(6-(trifluoromethyl)pyridin-2-yl)-N-(2-(trifluoromethyl)pyridin-4-yl)-1,3,5-triazin-2-amine

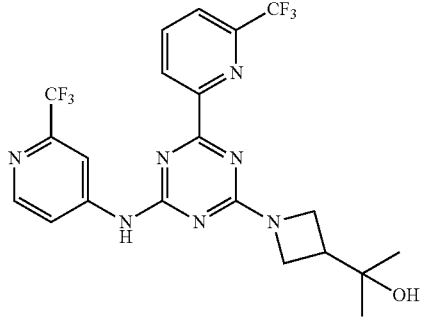 [SMILES: CC(C)(O)C1CN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 2-(azetidin-3-yl)propan-2-ol (14 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.63 (br, 1H), 8.53-8.73 (m, 3H), 8.25-8.30 (m, 1H), 8.06-8.09 (m, 1H), 7.93-7.94 (m, 1H), 4.62 (s, 1H), 4.09-4.15 (m, 4H), 2.69-2.79 (m, 1H), 1.09 (s, 6H). ES: m/z 500.2 [M+H]$^+$.

Example 49: 4-(2-(2-propyl-2-ol)azetidin-1-yl)-6-(6-(trifluoromethyl)pyridin-2-yl)-N-(2-(trifluoromethyl)pyridin-4-yl)-1,3,5-triazin-2-amine

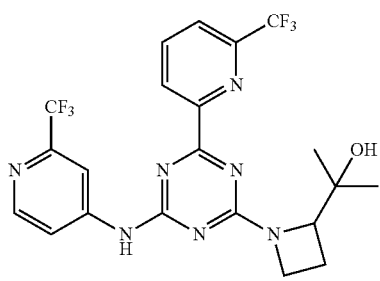 [SMILES: CC(C)(O)C1CCN1c1nc(Nc2ccnc(C(F)(F)F)c2)nc(-c2cccc(C(F)(F)F)n2)n1]

Step 1 Preparation of 2-(2-hydroxyprop-2-yl)azetidine-1-carboxylic acid tert-butyl ester

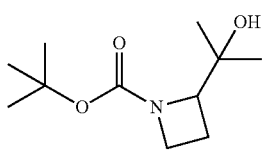

Methyl 1-tert-butoxycarbonyl azetidine-2-carboxylate (500 mg, 2.33 mmol) was dissolved in 10 mL of tetrahydrofuran, and methyllithium (4.66 mL, 4.66 mmol, 1 mol/L in THF) was added. The mixture was stirred at room temperature for 12 h, and then concentrated until dry to give the title compound.

Step 2 Preparation of 2-(azetidin-2-yl)propan-2-ol

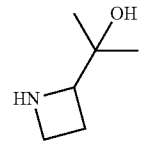

The 2-(2-hydroxyprop-2-yl)azetidin-1-carboxylic acid tert-butyl ester (100 mg, 0.46 mmol) was dissolved in 5 mL of dichloromethane, and 5 mL of trifluoroacetic acid was added. The mixture was stirred at room temperature for 12 h, and then concentrated until dry to give the title compound.

Step 3 Preparation of 4-(2-(2-propyl-2-ol)azetidin-1-yl)-6-(6-(trifluoromethyl) pyridin-2-yl)-N-(2-(trifluoromethyl)pyridin-4-yl)-1,3,5-triazin-2-amine

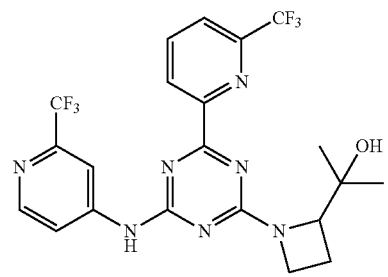 [SMILES: CC(C)(O)C1CCN1c1nc(Nc2ccnc(C(F)(F)F)c2)nc(-c2cccc(C(F)(F)F)n2)n1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 2-(azetidin-2-yl)propan-2-ol (14 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-d$_6$): δ 10.62 (br, 1H), 8.53-8.74 (m, 3H), 8.25-8.30 (m, 1H), 8.07-8.09 (m, 1H), 7.92-7.95 (m, 1H), 4.60 (s, 1H), 4.05-4.25 (m, 3H), 2.01-2.30 (m, 2H), 1.10 (s, 6H). ES: m/z 500.2 [M+H]$^+$.

Example 50: 4-(piperidin-1-yl)-6-(6-(trifluoromethyl)pyridin-2-yl)-N-(2-(trifluoromethyl) pyridin-4-yl)-1,3,5-triazin-2-amine

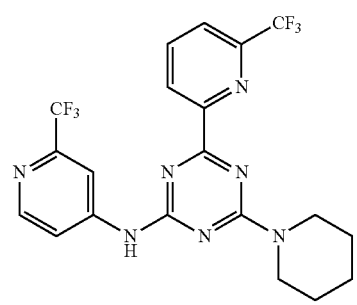 [SMILES: FC(F)(F)c1cc(Nc2nc(-c3cccc(C(F)(F)F)n3)nc(N3CCCCC3)n2)ccn1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and piperidine (10 mg, 0.12 mmol) and sodium carbonate (16 mg, 0.15 mmol) were added. The mixture was heated under reflux for 16 h. The resultant solution was filtered, and the filtrate was purified by column chromatography to give the title compound. ¹H NMR (500 MHz, DMSO-d₆): δ 10.58 (br, 1H), 8.54-8.72 (m, 3H), 8.26-8.30 (m, 1H), 8.07-8.09 (m, 1H), 7.92-7.94 (m, 1H), 3.69-3.93 (m, 4H), 1.50-1.70 (m, 6H). ES: m/z 470.1 [M+H]⁺.

Example 51: 4-((S)-3-cyanopyrrolidin-1-yl)-6-(6-(trifluoromethyl)pyridin-2-yl)-N-(2-(trifluoromethyl)pyridin-4-yl)-1,3,5-triazin-2-amine

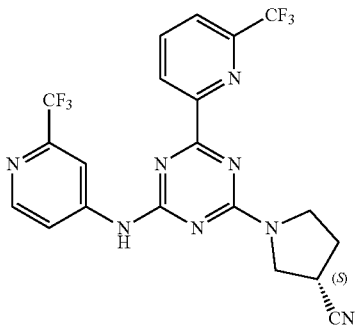

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (S)-3-cyanopyrrolidine (11.5 mg, 0.12 mmol) and sodium carbonate (16 mg, 0.15 mmol) were added. The mixture was heated under reflux for 16 h. The resultant solution was filtered, and the filtrate was purified by column chromatography to give the title compound. ¹H NMR (500 MHz, DMSO-d₆): δ 10.71 (s, 1H), 8.52-8.69 (m, 3H), 8.25-8.31 (m, 1H), 8.07-8.11 (m, 1H), 7.92-7.96 (m, 1H), 4.12-4.15 (m, 1H), 3.58-3.89 (m, 4H), 1.91-2.09 (m, 2H). ES: m/z 481.1 [M+H]⁺.

Example 52: 4-((R)-3-cyanopyrrolidin-1-yl)-6-(6-(trifluoromethyl)pyridin-2-yl)-N-(2-(trifluoromethyl)pyridin-4-yl)-1,3,5-triazin-2-amine

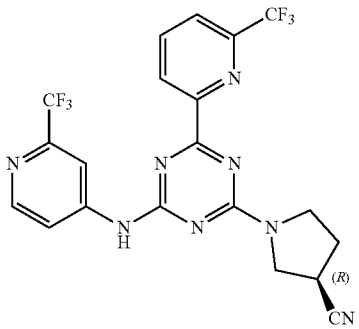

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (R)-3-cyanopyrrolidine (11.5 mg, 0.12 mmol) and sodium carbonate (16 mg, 0.15 mmol) were added. The mixture was heated under reflux for 16 h. The resultant solution was filtered, and the filtrate was purified by column chromatography to give the title compound. ¹H NMR (500 MHz, DMSO-d₆): δ 10.71 (s, 1H), 8.52-8.69 (m, 3H), 8.25-8.31 (m, 1H), 8.07-8.11 (m, 1H), 7.92-7.96 (m, 1H), 4.12-4.15 (m, 1H), 3.58-3.89 (m, 4H), 1.91-2.09 (m, 2H). ES: m/z 481.1 [M+H]⁺.

Example 53: 4-((3S,4S)-3-hydroxy-4-cyanopyrrolidin-1-yl)-6-(6-(trifluoromethyl) pyridin-2-yl)-N-(2-(trifluoromethyl)pyridin-4-yl)-1,3,5-triazin-2-amine

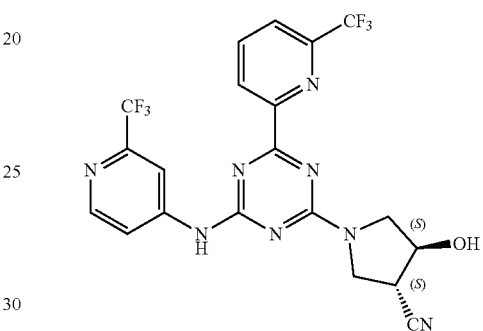

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and (3S,4S)-3-hydroxy-4-cyanopyrrolidine (13.4 mg, 0.12 mmol) and sodium carbonate (16 mg, 0.15 mmol) were added. The mixture was heated under reflux for 16 h. The resultant solution was filtered, and the filtrate was purified by column chromatography to give the title compound. ¹H NMR (500 MHz, DMSO-d₆): δ 10.75 (s, 1H), 8.55-8.75 (m, 3H), 8.23-8.35 (m, 1H), 8.10-8.11 (m, 1H), 7.97-8.00 (m, 1H), 5.40-5.53 (m, 1H), 5.07-5.30 (m, 1H), 4.32 (s, 1H), 3.65-3.97 (m, 4H). ES: m/z 497.1 [M+H]⁺.

Example 54: 4-(3-Hydroxy-3-cyanopyrrolidin-1-yl)-6-(6-(trifluoromethyl) pyridin-2-yl)-N-(2-(trifluoromethyl)pyridin-4-yl)-1,3,5-triazin-2-amine

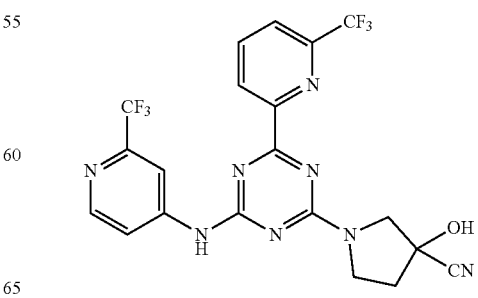

Step 1 Preparation of 3-hydroxy-3-cyanopyrrolidine

3-Hydroxy-3-cyanopyrrolidine-1-carboxylic acid tert-butyl ester (200 mg, 0.94 mmol) was dissolved in 5 mL of dichloromethane, and 5 mL of trifluoroacetic acid was added. The mixture was stirred at room temperature for 12 h, and then concentrated until dry to give the title compound.

Step 2 Preparation of 4-(3-hydroxy-3-cyanopyrrolidin-1-yl)-6-(6-(trifluoromethyl) pyridin-2-yl)-N-(2-(trifluoromethyl)pyridin-4-yl)-1,3,5-triazin-2-amine

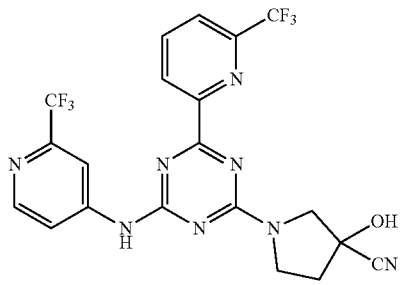 [SMILES: N#CC1(O)CCN(c2nc(Nc3ccnc(C(F)(F)F)c3)nc(-c3cccc(C(F)(F)F)n3)n2)C1]

4-Chloro-6-(6-(trifluoromethyl)pyridin-2-yl)-N-(2-(trifluoromethyl)pyridin-4-yl)-1,3,5-triazin-2-amine (43 mg, 0.10 mmol) prepared in step 4 of Example 1 was dissolved in 5 mL of tetrahydrofuran, and 3-hydroxy-3-cyanopyrrolidine (13.4 mg, 0.12 mmol) and sodium carbonate (16 mg, 0.15 mmol) were added. The mixture was heated under reflux for 16 h. The resultant solution was filtered, and the filtrate was purified by column chromatography to give the title compound. $^1$H NMR (500 MHz, DMSO-$d_6$): δ 10.60 (s, 1H), 8.53-8.83 (m, 3H), 8.21-8.30 (m, 1H), 8.07-8.13 (m, 1H), 7.76-8.01 (m, 1H), 6.55 (s, 1H), 3.77-4.21 (m, 4H), 2.12-2.29 (m, 2H). ES: m/z 497.1 [M+H]$^+$.

Example 55: 4-(3,3,4,4-Tetrafluoropyrrolidin-1-yl)-6-(6-(trifluoromethyl)pyridin-2-yl)-N-(2-(trifluoromethyl)pyridin-4-yl)-1,3,5-triazin-2-amine

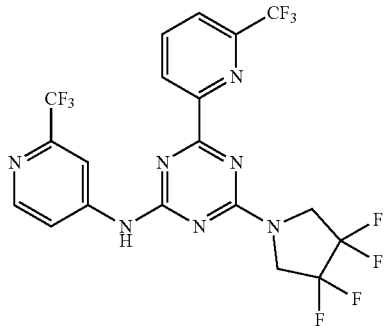 [SMILES: FC(F)(F)c1cc(Nc2nc(-c3cccc(C(F)(F)F)n3)nc(N3CC(F)(F)C(F)(F)C3)n2)ccn1]

4-Chloro-6-(6-(trifluoromethyl)pyridin-2-yl)-N-(2-(trifluoromethyl)pyridin-4-yl)-1,3,5-triazin-2-amine (420 mg, 1.00 mmol) prepared in step 4 of Example 1 was added to 10 mL of tetrahydrofuran, and 3,3,4,4-tetrafluoropyrrolidine hydrochloride (219 mg, 1.22 mmol) and sodium carbonate (212 mg, 2.02 mmol) were added. The mixture was heated under reflux and reacted for 16 h, and then cooled. The resultant solution was filtered by suction, and silica gel was added to the filtrate to make a mixture for chromatography. The resultant mixture was purified by column chromatography to give the title compound. $^1$H NMR (300 MHz, DMSO-$d_6$): δ 10.88 (s, 1H), 8.65 (d, 2H), 8.57 (d, 1H), 8.31 (t, 1H), 8.10 (d, 1H), 7.99 (d, 1H), 3.85-3.61 (m, 4H). ES: m/z 528.1 [M+H]$^+$.

Experimental Example 1 Evaluation of Inhibitory Activity of Compounds on Enzyme in Vitro

1. Experimental Materials

The control compound is Compound 409 disclosed in WO 2013/102431 (see page 134 of the application specification), chemical name 2-methyl-1-(4-(6-(trifluoromethyl)pyridin-2-yl)-6-(2-(trifluoromethyl)pyridin-4-yl amino)-1,3,5-triazin-2yl amino)propan-2-ol (AG-221), prepared by the method described in WO2013/102431 and identified by hydrogen spectroscopy and mass spectrometry.

Compounds: the compounds of the present disclosure prepared in the above examples, each of which was formulated into 20 mM with DMSO, and then sequentially diluted to 10 μM, 3.33 μM, 1.11 μM, 370.37 nM, 123.46 nM, 41.15 nM, 13.72 nM, 4.57 nM, 1.52 nM, and 0.51 nM.

Reagents: 1× reaction buffer (50 mM KH2PO4, 10% glycerol, 150 mM NaCl, 0.05% BSA, 2 mM 2-mercaptoethanol), prepared before use; IDH2 wild-type enzyme (IDH2-WT), purchased from BPS, Cat. No. 71074-1; IDH2-R140Q mutant enzyme (IDH2-R140Q), purchased from BPS, Cat. No. 71100-1; NADPH, purchased from Sigma, Cat. No. N5130; NADP, purchased from Sigma, Cat. No. N5755; dimethyl sulfoxide (DMSO), purchased from Sigma, USA; α-ketoglutarate, purchased from Sigma, Cat. No. K1875; Isocitrate, purchased from Sigma, Cat. No. 11252; Diaphorase, purchased from Worthington Biochemical, Cat. No. LS004327.

Instrument: SpectraMax M3 Multi-Mode Microplate Reader, purchased from Molecular Devices.

2. Experimental Methods

2.1. Enzyme Reaction System

In the IDH2-WT reaction system, the final concentration of IDH2-WT enzyme was 0.06 ng/ml, the final concentration of the reaction substrate Isocitrate was 150 μM, and the final concentration of the reaction cofactor NADP was 25 μM; in the IDH2-R140Q reaction system, the final concentration of IDH2-R140Q enzyme was 0.3 ng/ml, the final concentration of the reaction substrate α-ketoglutarate was 4 mM, and the final concentration of the reaction cofactor NADPH was 15 μM.

2.2. Method of Performing Enzyme Reaction

In a 96-well plate, 40 μL of reaction buffer containing 2× enzyme (IDH2-WT or IDH2-R140Q) and cofactor (NADP or NADPH) was added to each well of the compound group and the DMSO control group, and 40 μL of reaction buffer containing 2× cofactor (NADP or NADPH) was added to each well of the enzyme-free control group.

20 μL of reaction buffer containing 4× compound to be tested was added to each well of the compound group. The compound was pre-formulated into 200× mother liquor with 100% DMSO; in the final reaction system, the concentration of DMSO was 0.5%. 20 μL of reaction buffer containing DMSO was added to each well of the DMSO control group; in the final reaction system, the concentration of DMSO was 0.5%.

The compound was mixed well with the enzyme and cofactor, and pre-incubated at room temperature for 16 h;

20 μL of reaction buffer containing 4× reaction substrate was added to each well. After mixed uniformly, the mixture was reacted at room temperature for 1 h.

2.3. Termination of the Reaction

3× termination and detection solution (it was prepared with reaction buffer, the final concentration of Diaphorase was 0.015 mg/mL, and the final concentration of Resazurin was 0.03 mM) was prepared. 40 μL of 3× termination and detection solution was added to each well of the enzyme reaction system. After mixed uniformly, the mixture was incubated at room temperature for 10 min;

40 μL of the above mixture was pipetted into each well of a 384-well plate, pipetted twice, and placed on a Microplate Reader to obtain the fluorescence value (Ex/Em=544/590 nm).

2.4. Data Processing

Fluorescence values of two wells were obtained and averaged and the activity rate (Activity %) was calculated. The calculation formula: Activity %=(Measured data−Subtract background)/(DMSO Control−Subtract background)× 100, wherein "Measured data" is fluorescence value of the compound in the pre-incubated wells, "Subtract background" is the fluorescence value of the enzyme-free control wells, and "DMSO Control" is the fluorescence value in the DMSO pre-incubated wells. Data was processed by GraphPad Prism v5.0 software and fitted to obtain $IC_{50}$. The experimental data is shown in Table 1.

TABLE 1

| Compound | R140Q $IC_{50}$ (nM) | Compound | R140Q $IC_{50}$(nM) |
| --- | --- | --- | --- |
| Example 1 | 11 | Example 2 | 23 |
| Example 3 | 22 | Example 4 | 15 |
| Example 5 | 25 | Example 7 | 20 |
| Example 8 | 18 | Example 9 | 22 |
| Example 10 | 19 | Example 11 | 14 |
| Example 12 | 25 | Example 13 | 15 |
| Example 15 | 18 | Example 17 | 23 |
| Example 18 | 26 | Example 19 | 14 |
| Example 21 | 25 | Example 22 | 24 |
| Example 23 | 30 | Example 25 | 15 |
| Example 26 | 21 | Example 27 | 12.5 |
| Example 28 | 12.2 | Example 29 | 5.8 |
| Example 31 | 21.3 | Example 32 | 26.5 |
| Example 33 | 29.2 | Example 34 | 14.1 |
| Example 35 | 8.3 | Example 38 | 25.2 |
| Example 41 | 16.1 | Example 42 | 5.1 |
| Example 43 | 5.8 | Example 44 | 8.8 |
| Example 45 | 6.3 | Example 48 | 19 |
| Example 50 | 22 | Example 51 | 18 |
| Example 52 | 23 | Example 55 | 10.1 |
| AG-221 | 21 | | |

The experimental results show that the $IC_{50}$ values of the compounds of the present disclosure are in nM level, and the $IC_{50}$ values of some compounds are better than that of the control drug AG-221, and especially, some compounds have more than three times the activity against the R140Q mutant enzyme.

Experimental Example 2 Evaluation of Cell Activity of Compounds In Vitro

1. Experimental Materials 1.1 Compounds to be tested: the compounds of the present disclosure prepared in the above examples, each of which was formulated into 20 mM with DMSO, and then sequentially diluted 3 times to 10 μM, 3.33 μM, 1.11 μM, 370.37 nM, 123.46 nM, 41.15 nM, 13.72 nM, 4.57 nM and 1.52 nM.

1.2 Cells: human glioblastoma cell line U87-MG, purchased from the American Type Culture Collection (ATCC); U87-MG cell line of overexpressed mutant IDH2 (R140Q), which was constructed by Nanjing Kingsray Biotechnology Co., Ltd. using conventional molecular biology method, in brief, the method comprises the following steps:

(1) Subclone wild type IDH2 into Lenti-Puro vector (purchased from GenScript's MGC library, Slot: IRAU-112-d-10, IRAT-17-b-7), obtain IDH2 (R140Q) mutant by point mutation, and prepare transfection grade recombinant lentiviral vector carrying IDH2 (R140Q).

(2) Test the titer of the virus.

(3) Transduct U87-MG host cells with the constructed recombinant lentiviral vector, screen for stable cells with puromycin, and confirm the expression of IDH2 (R140Q) by qPCR and Western blotting.

(4) Obtain monoclone by limiting dilution and confirm by qPCR and Western blotting, and detect 2-hydroxyglutarate (2-HG) level by using LC-MS.

1.3 Reagents:

MEM medium, purchased from Invitrogen, USA;

Fetal bovine serum (FBS), purchased from Invitrogen, USA;

Trypsin, purchased from Invitrogen, USA;

2-D-α-hydroxyglutaric acid disodium salt (2-HG) standard, purchased from Sigma, Cat. No. SLBD 8946V, purity≥95%;

Phenacetin standard (internal standard/IS): purchased from Sigma, purity≥98%;

Acetonitrile/methanol (chromatographically pure), purchased from Merck;

All the remaining reagents are commercially available (analytical grade).

1.4 Instruments:

AB SCIEX API4500 liquid chromatograph/mass spectrometer (LC-MS/MS) with Japan Shimadzu Ultra High Performance Liquid Chromatography System (LC-30A), American AB Mass Spectrometry System (API4500), Electrospray Ion Source and Analyst 1.6.2 workstation;

Milli-Q Ultra Pure Water Machine (Millipore Inc);

TARGIN VX-II oscillator;

HITACHI CF 16RXII desktop high speed refrigerated centrifuge;

Thermo electric pipette.

2. Experimental Methods 2.1 Cell culture:

The U87-MG cells without transfected IDH2 (R140Q) was used in the non-mutation control group, and the U87-MG cells overexpressed mutant IDH2 (R140Q) [U87-MG (IDH2-R140Q)] was used in the compound groups and the DMSO control group.

Cell recovery: U87-MG (IDH2-R140Q) cells and U87-MG cells were put into a 37° C. water bath, then transferred to 15 mL of pre-warmed medium, centrifuged at 1000 rpm for 5 minutes, and the medium was discarded. The cells were resuspended in 15 mL of fresh medium, transferred to a T75 flask and cultured in a 37° C. incubator with 5% $CO_2$. After 24 hours, the medium was changed to fresh medium.

Cell passage: The above-mentioned recovered cells were transferred to a 50 mL sterile centrifuge tube, centrifuged at 1000 rpm for 5 minutes, and the medium was discarded. The cells were resuspended evenly and counted. The cell density was adjusted appropriately in a 15 mL fresh medium, and then added to T75 culture flask. The culture flask was incubated in an incubator with 5% $CO_2$ at 37° C.

2.2 Experimental Steps

After cells grown to a relatively high density in the culture dish, the cells were trypsinized, resuspended in medium (MEM+10% FBS), and counted. After adjusting the cell concentration, the resuspended cells were seeded in a 96-well plate at $5 \times 10^3$ cells per well. After inoculation, the cells were cultured for 24 hours until the cells adhered. The medium were sucked out, and the medium containing gradient concentration of compound was added, 100 µL per well. The cells were further cultured for 72 hours. The s 20 µL of upernatant was taken and put into a 2 mL 96-well sample-processing plate. 480 µL of dilution solution was added and shaken for mixing, and then centrifuged at 4500 rpm for 5 minutes. 200 µL of supernatant was transferred for LC-MS/MS injection analysis.

2.3 LC-MS/MS Analysis Conditions 2.3.1 Chromatographic Conditions

Column: Shim-pack XR-ODS 30L*2.0; mobile phase: acetonitrile-0.2% ammonia, 5 mM ammonium acetate aqueous solution; column temperature: 30° C.; flow rate: 0.4 mL/min; gradient elution conditions are as follows:

TABLE 2

| Chromatographic elution conditions | |
|---|---|
| Time(min) | Acetonitrile(%) |
| 0.01 | 2 |
| 0.20 | 2 |
| 1.00 | 70 |
| 2.00 | 70 |
| 2.01 | 2 |
| 3.00 | | retention time: t R, 2-HG ≈ 0.21 min; t R, IS ≈ 1.41 min.

2.3.2 Mass Spectrometry Conditions

Atmospheric piezoelectric chemical ionization (APCI) was used. Source parameters was set as follows: IonSpray Voltage/IS-4500V; auxiliary gas 1 (Ion Source Gas 1/GS 1, N2), 55Arb; auxiliary gas 2 (Ion Source Gas 2, N2), 55Arb; auxiliary gas heating temperature (Temperature/TEM), 500° C.; curtain gas/CUR, 25Arb; collision gas/CAD, N2, 8 Pa.

Multi-ion reaction monitoring (MRM) in negative ion mode (Negative) was used. The MRM parameters for 2-HG: parent ion (Q 1 Mass), 146.9 Da; daughter ion (Q 3 Mass), 129.0 Da; Declusting Potential (DP), −15.3V; and collision voltage (Collision Energy/CE), −14.5 eV. The internal standard (IS) MRM parameters: parent ion (Q 1 Mass), 178.0 Da; daughter ion (Q3 Mass), 149.0 Da; Declustor Potential (DP), −51V; collision voltage (Collision Energy/CE), −17 eV 2.4 Data Processing By determining the 2-HG content in the cell culture supernatant of each well using LC-MS/MS, the mutant enzyme activity (2-HG remaining compared to untreated %) was calculated. The calculation formula: 2-HG remaining compared to untreated %=(Measured 2-HG level—U87-MG control 2-HG level)/(Untreated 2-HG level—U87-MG control 2-HG level)×100. Wherein, "Measured 2-HG level" is 2-HG content in the medium supernatant of the U87-MG (IDH2-R140Q) well incubated with the compounds, "U87-MG control 2-HG level" is the 2-HG content in the medium supernatant of the U87-MG well, "Untreated 2-HG level" is the 2-HG content in the medium supernatant of U87-MG (IDH2-R140Q) well pre-incubated with equal concentration of DMSO. Data were processed by GraphPad Prism v5.0 software and fitted to obtain $IC_{50}$. $IC_{50}$ is the concentration of the compounds which are able to inhibit mutant enzyme activity by 50% in cells. The $IC_{50}$ results of some compounds are shown in Table 3.

TABLE 3

| Compound | $IC_{50}$(nM) | Compound | $IC_{50}$(nM) |
|---|---|---|---|
| Example 1 | 15 | Example 2 | 27 |
| Example 3 | 24 | Example 4 | 21 |
| Example 27 | 31.2 | Example 28 | 25.1 |
| Example 29 | 17.1 | Example 31 | 38.1 |
| Example 32 | 36.1 | Example 33 | 10.2 |
| Example 34 | 17.1 | Example 35 | 9.8 |
| Example 38 | 59.1 | Example 40 | 33.1 |
| Example 41 | 10.1 | Example 42 | 8.1 |
| Example 43 | 9.6 | Example 44 | 5.1 |
| Example 45 | 10.2 | Example 55 | 15.0 |
| AG-221 | 30.2 | | |

The experimental results show that the $IC_{50}$ values of the compounds of the present disclosure are in nM level, and the $IC_{50}$ values of some compounds are much better than that of the control drug AG-221, showing a very good inhibitory ability against IDH2.

Experimental Example 3 Efficacy Evaluation on Subcutaneous Xenograft Tumor Caused by U87-MG (IDH2-R140Q) Mutant Cells in Vivo 1. Experimental Materials 1.1 Compound to be tested: the compounds of the present disclosure prepared in the above examples, each of which was formulated into a solution in corresponding concentrations by using a vehicle (2% absolute ethanol:10% Solutol®:88% physiological saline (v/v/v)).

1.2 Cells and reagents: see the experimental materials section of Experimental Example 2.

1.2 Animals: BALB/c nude mice, 6-7 weeks old, female, 18-22 g, purchased from Nanjing Jinlaichang Company.

1.3 Cells, reagents and instruments: see the experimental materials section of Experimental Example 2

2. Experimental Methods 2.1 Animal Inoculation

U87-MG (IDH2-R140Q) cells and U87-MG cells (wild type) were expanded, and cells in logarithmic growth phase were used for tumor inoculation in vivo. 16 mice were inoculated subcutaneously into the right lower back of the body at an amount of $2 \times 10^6$ cells/mouse (the volume ratio of cell suspension to Matrigel was 1:0.8).

2.2 Grouping and Administration

The non-mutation control group was nude mice inoculated with U87-MG cells, and the test compound groups and vehicle control group were nude mice inoculated with U87-MG (IDH2-R140Q) cells.

Each group was intragastrically administered with a corresponding concentration of the compound solution, the administration volume was 100 μL/10 g body weight, and the control group was administered the same volume of blank vehicle.

After 10 days of administration, the mice were sacrificed. The tumors were exfoliated, homogenized, and the 2-HG content in the tumor was examined.

2.3 LC-MS/MS Analysis Conditions

As for chromatographic and mass spectrometry conditions, see the experimental method section of Experimental Example 2.

2.4 Data Processing

The 2-HG concentration in the homogenate of each animal tumor in each group was determined by LC-MS/MS. The percentage (2-HG %) was calculated; the calculation formula is as follows 2-HG %=(2-HG concentration of administration group tumor−2-HG concentration of U87-MG control group tumor)/(2-HG concentration of U87-MG(IDH2-R140Q) control group tumor−2-HG concentration of U87-MG control group tumor)×100%.

The relative percentages (mean) of 2-HG levels in the tumors of mice after administration of some compounds are shown in Table 5.

TABLE 5

Intratumor 2-HG(%) after 10 days of administration

| Groups | Dose(mg/kg) | 2-HG(%) |
|---|---|---|
| U87-MG control group | — | 0 |
| U87-MG (IDH2-R140Q) control group | — | 100 |
| AG-221 | 25 | −4 |
| AG-221 | 12.5 | 9 |
| AG-221 | 6.25 | 58 |
| Example 1 | 25 | 22 |
| Example 2 | 12.5 | 14 |
| Example 3 | 12.5 | 22 |
| Example 22A | 6.25 | 31 |
| Example 22B | 6.25 | −2 |
| Example 23 | 6.25 | 67 |
| Example 34 | 12.5 | 24 |
| Example 45 | 6.25 | 17 |
| Example 51 | 6.25 | 38 |
| Example 55 | 6.25 | 1 |

Experimental results show that in the U87-MG (IDH2-R140Q) mutation subcutaneous xenograft model, the compounds of the present disclosure have very good ability of lowering high level of 2-HG caused by IDH2 mutations in tumors, and some compounds such as the compounds of examples 22A, 22B, 45, 51, 55 have substantially superior ability of lowering 2-HG level while compared with that of positive compound AG-221. The compounds of the present disclosure are expected to have a good inhibitory effect on the production and progression of tumors caused by IDH2 mutations.

Experimental Example 4 Human Acute Myeloid Leukemia NOD/SCID Animal Model

1. Experimental Materials 1.1 Compounds to be tested: the compounds of the present disclosure prepared in the above examples, each of which was formulated into a solution in corresponding concentrations by using a vehicle (2% absolute ethanol:10% Solutol™: 88% physiological saline (v/v/v)).

1.2 Cells: human acute myeloid leukemia AM7577 cells, provided by Sino-American Crown Biotechnology (Beijing) Co., Ltd 1.3 Reagent: FITC anti-human CD45, purchased from Biolegend 1.4 Animals: NOD/SCID mice, 3-4 weeks old, female, purchased from Beijing Huakangkang Biotechnology Co., Ltd 1.5 Instrument: flow cytometer FACSCalibur, BD 2. Experimental Methods 2.1 Animal Inoculation Each mouse was inoculated through the tail vein at an amount of $2\times10^6$ cells resuspended in 100 uL of PBS.

2.2 Grouping and Administration

Orbital blood samples of animals were collected weekly, labeled with human CD45, and the percentage of positive cells was detected. The animals were grouped when the percentage of peripheral blood CD45+ cells reached 5%. The proportion of peripheral blood CD45+ cells reached 5% on the 40th day after inoculation. After grouping, drugs were administered by gastric gavageonce a day for 14 days. The grouping and administration are shown in Table 6

TABLE 6

| Group | Number of animals | Administration group | Dose(mg/kg)* |
|---|---|---|---|
| 1 | 8 | Vehicle control | — |
| 2 | 4 | AG -221 | 45 |
| 3 | 8 | AG -221 | 15 |
| 4 | 8 | Example 22B | 45 |
| 5 | 8 | Example 22B | 15 |

*Note:
The administration volume to animals was adjusted according to 10 μL/g body weight.

2.3 Survival Rate and Survival Period Observations:

The mortality rate of the animals after administration and the survival period of the surviving animals were observed. The number of surviving animals in each group 14 days after administration is shown in Table 7. The survival period of each group of animals after administration is shown in FIG. 1.

TABLE 7

| Group | Administration group | Dose(mg/kg) | Number of animals | Numbers of surviving animals |
|---|---|---|---|---|
| 1 | Vehicle control | — | 8 | 1 |
| 2 | AG -221 | 45 | 4 | 3 |
| 3 | AG -221 | 15 | 8 | 6 |
| 4 | Example 22B | 45 | 8 | 7 |
| 5 | Example 22B | 15 | 8 | 7 |

The results of the experiment show that only one animal in the vehicle control group survived after 14 days of administration, 3 of the 4 animals in the high dose group (45 mg/kg) of the positive compound AG-221 survived, 6 of the 8 animals in the low dose group (15 mg/kg) of the positive compound AG-221 survived, while 7 animals in both low and high dose group of the compounds of the present disclosure survived. As can be seen from FIG. 1, as compared with the vehicle control group, the survival period of the mice treated with the compounds of the present disclosure was significantly prolonged, and with a increasing dose, the efficacy of the compounds of the present disclosure was significantly superior to that of the positive compound AG-221, and the survival periods of the animals have increased significantly. The compounds of the present disclosure can significantly improve the survival rate and survival period of tumor-bearing mice.

Although the present disclosure has been described hereinabove, it should be understood by those skilled in the art that various modifications and changes to the present disclosure may be made without departing from the spirit and scope of the present disclosure. The scope of the present disclosure is not limited to the details described above, but rather to the claims.

What is claimed is:

1. A compound represented by formula (I) or a pharmaceutically acceptable salt, crystal, solvate or prodrug thereof,

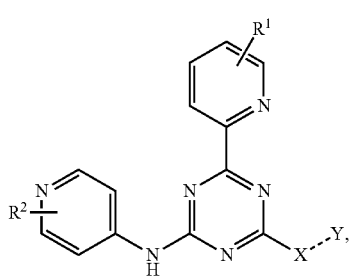

(I)

wherein $R^1$ and $R^2$ are each independently selected from the group consisting of hydrogen, halogen, hydroxyl, alkyl, cycloalkyl, heterocyclyl, haloalkyl, hydroxyalkyl, alkoxy, haloalkoxy, amino, alkylamino, alkylacylamino, alkylacyl, aminoacyl, alkylaminoacyl, carboxyl, nitro and cyano, wherein the hydroxyl, alkyl, cycloalkyl, heterocyclyl, haloalkyl, hydroxyalkyl, alkoxy, haloalkoxy, amino, alkylamino, alkylacylamino, alkylacyl, aminoacyl, alkylaminoacyl, and carboxyl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl; and X is selected from the group consisting of $N(R^3)$, O, S, and $C(R^4)$, wherein when X is $N(R^3)$, $R^3$ and Y together with the nitrogen atom to which they are attached form azacyclopropyl, azacyclobutyl, tetrahydropyrrolyl, piperidinyl, dihydropyrrolyl, tetrahydropyridyl, azathiaheterocyclyl, pyrazolidinyl, dihydropyrazolyl, imidazolidinyl, dihydroimidazolyl, pyrazolyl, thiazolidinyl, dihydrothiazolyl, isoxazolidinyl, dihydroisoxazolyl, isothiazolidinyl, dihydroisothiazolyl, hexahydropyrimidinyl, tetrahydropyrimidinyl, dihydropyrimidinyl, hexahydropyridazinyl, tetrahydropyridazinyl, dihydropyridazinyl or thiomorpholinyl, each which is optionally substituted with one or more groups selected from the group consisting of oxo group, alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl; when X is $C(R^4)$, $R^4$ and Y together with the carbon atom to which they are attached form carbocyclyl or heterocyclyl, each of which is optionally substituted with one or more groups selected from the group consisting of oxo group, alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl;

when X is selected from the group consisting of O and S, Y is selected from the group consisting of alkyl, cycloalkyl, heterocyclyl, haloalkyl, hydroxyalkyl, alkoxy, haloalkoxy, alkylamino, alkylacylamino, alkylacyl, aminoacyl and alkylaminoacyl, and the dotted line between X and Y represents a single bond.

2. The compound or the pharmaceutically acceptable salt, crystal, solvate or prodrug thereof according to claim 1, wherein the formula (I) has a structure represented by formula (Ia):

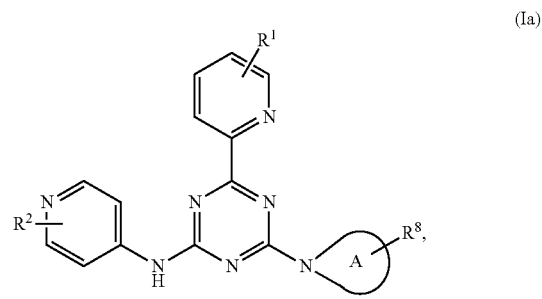

(Ia)

wherein $R^1$ and $R^2$ are each independently selected from the group consisting of hydrogen, halogen, hydroxyl, alkyl, cycloalkyl, heterocyclyl, haloalkyl, hydroxyalkyl, alkoxy, haloalkoxy, amino, alkylamino, alkylacylamino, alkylacyl, aminoacyl, alkylaminoacyl, carboxyl, nitro and cyano, wherein the hydroxyl, alkyl, cycloalkyl, heterocyclyl, haloalkyl, hydroxyalkyl, alkoxy, haloalkoxy, amino, alkylamino, alkylacylamino, alkylacyl, aminoacyl, alkylaminoacyl, and carboxyl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;

ring A is heterocyclyl selected from the group consisting of $C_{3-8}$ azathiaheterocyclyl azacyclopropyl, azacyclobutyl, tetrahydropyrrolyl, piperidinyl, dihydropyrrolyl, tetrahydropyridyl, and pyrazolidinyl; and $R^8$ is one or more groups selected from the group consisting of hydrogen, oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl, wherein the oxo group, alkyl, haloalkyl, hydroxyalkyl, cycloalkyl, heterocyclyl, alkoxy, haloalkoxy, hydroxyalkoxy, alkylamino, hydroxyl, amino, carboxyl, alkylacyl, aminoacyl, alkylaminoacyl, sulfonyl, sulfinyl, mercapto, aryl and heteroaryl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl.

3. The compound or the pharmaceutically acceptable salt, crystal, solvate or prodrug thereof according to claim 1, wherein R³ and Y together with the nitrogen atom to which they are attached form azacyclopropyl, azacyclobutyl, tetrahydropyrrolyl, piperidinyl, dihydropyrrolyl, tetrahydropyridyl, pyrazolidinyl, dihydropyrazolyl, imidazolidinyl, dihydroimidazolyl, pyrazolyl, thiazolidinyl, dihydrothiazolyl, isoxazolidinyl, dihydroisoxazolyl, isothiazolidinyl, dihydroisothiazolyl, hexahydropyrimidinyl, tetrahydropyrimidinyl, dihydropyrimidinyl, hexahydropyridazinyl, tetrahydropyridazinyl, dihydropyridazinyl, or thiomorpholinyl, wherein said groups are optionally substituted with one or more groups selected from the group consisting of oxo group, $C_{1-3}$ alkyl, $C_{3-6}$ cycloalkyl, $C_{3-6}$ heterocycloalkyl, halo $C_{1-3}$ alkyl, hydroxy $C_{1-3}$ alkyl, $C_{1-3}$ alkoxy, $C_{1-3}$ alkylamino, halogen, hydroxyl, amino, carboxyl, nitro, cyano, $C_{1-3}$ alkylacyl, aminoacyl, $C_{1-3}$ alkylaminoacyl, sulfonyl, sulfinyl, mercapto, phenyl and heteroaryl.

4. The compound or the pharmaceutically acceptable salt, crystal, solvate or prodrug thereof according to claim 2, wherein the formula (I) has a structure represented by formula (Iaa):

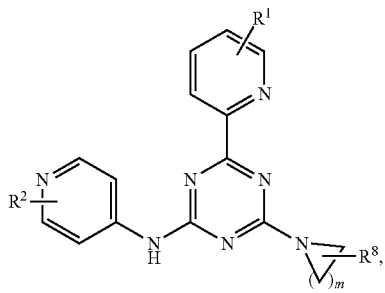

(Iaa)

wherein
R¹ and R² are each independently selected from the group consisting of hydrogen, halogen, hydroxyl, alkyl, cycloalkyl, heterocyclyl, haloalkyl, hydroxyalkyl, alkoxy, haloalkoxy, amino, alkylamino, alkylacylamino, alkylacyl, aminoacyl, alkylaminoacyl, carboxyl, nitro and cyano, wherein the hydroxyl, alkyl, cycloalkyl, heterocyclyl, haloalkyl, hydroxyalkyl, alkoxy, haloalkoxy, amino, alkylamino, alkylacylamino, alkylacyl, aminoacyl, alkylaminoacyl, and carboxyl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl;
R⁸ is one or more groups selected from the group consisting of hydrogen, oxo group, alkyl, haloalkyl, hydroxyalkyl, cycloalkyl, heterocyclyl, alkoxy, haloalkoxy, hydroxyalkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl, wherein the oxo group, alkyl, haloalkyl, hydroxyalkyl, cycloalkyl, heterocyclyl, alkoxy, haloalkoxy, hydroxyalkoxy, alkylamino, hydroxyl, amino, carboxyl, alkylacyl, aminoacyl, alkylaminoacyl, sulfonyl, sulfinyl, mercapto, aryl and heteroaryl are optionally substituted with one or more groups selected from the group consisting of halogen, hydroxyl, alkyl, haloalkyl, hydroxyalkyl, alkoxy, haloalkoxy, hydroxyalkoxy, nitro, carboxyl, cyano, amino, monoalkylamino, dialkylamino, cycloalkyl, heterocyclyl, aryl and heteroaryl; and m is 1, 2, 3, 4, 5 or 6.

5. The compound or the pharmaceutically acceptable salt, crystal, solvate or prodrug thereof according to claim 1, wherein the formula (I) has a structure represented by formula (Ib):

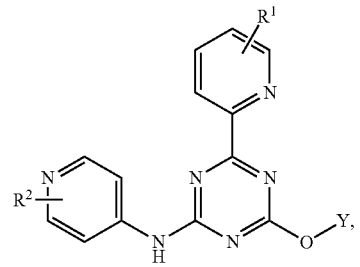

(Ib)

wherein Y is selected from the group consisting of alkyl, haloalkyl, hydroxyalkyl, alkoxy, haloalkoxy, alkylamino, alkylacylamino, alkylacyl, aminoacyl and alkylaminoacyl.

6. The compound or the pharmaceutically acceptable salt, crystal, solvate or prodrug thereof according to claim 1, wherein
X is C(R⁴), R⁴ and Y together with the carbon atom to which they are attached form $C_{3-8}$ carbocyclyl or $C_{3-8}$ heterocyclyl, wherein the heterocyclyl further contains one or more heteroatoms selected from the group consisting of N, O and S, and the carbocyclyl or heterocyclyl are optionally substituted with one or more groups selected from the group consisting of oxo group, alkyl, cycloalkyl, heterocycloalkyl, alkoxy, alkylamino, halogen, hydroxyl, amino, carboxyl, nitro, cyano, alkylacyl, aminoacyl, alkylaminoacyl, sulfonyl, sulfinyl, mercapto, aryl and heteroaryl.

7. A compound or the pharmaceutically acceptable salt, crystal, solvate or prodrug thereof, wherein the compound is selected from:

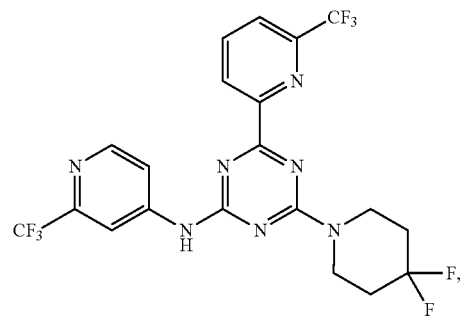

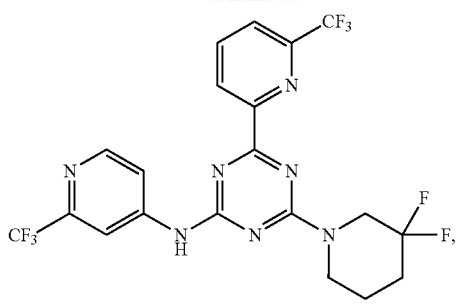
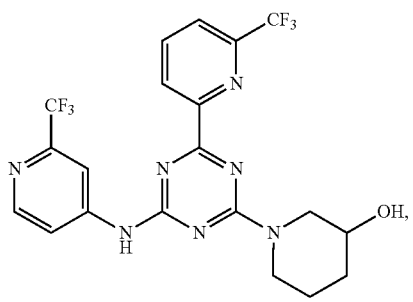
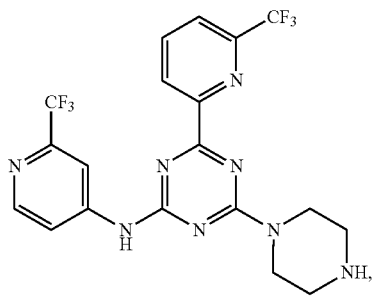
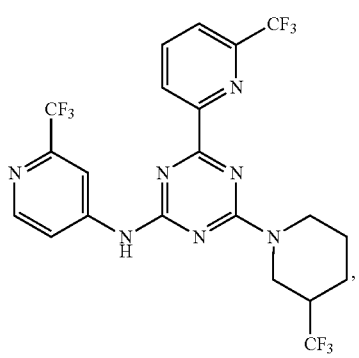
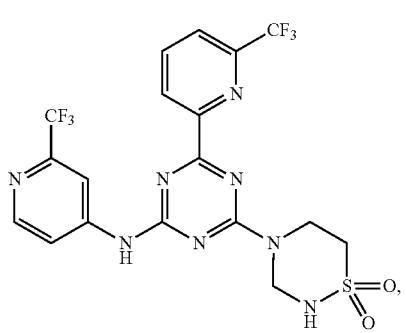
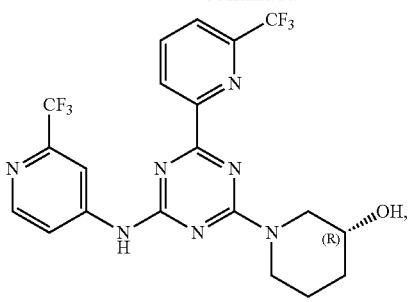
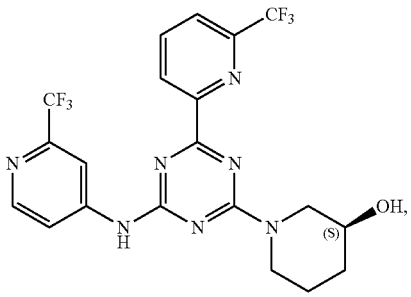
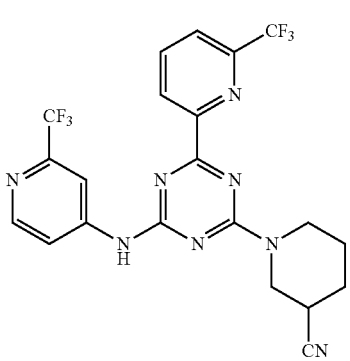
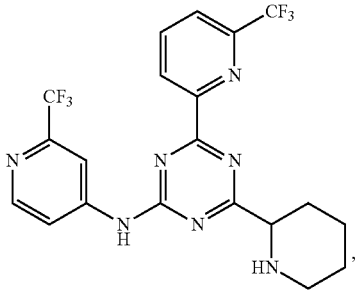

-continued
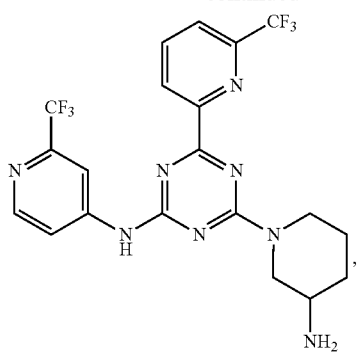
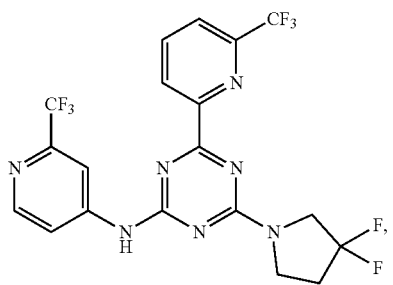
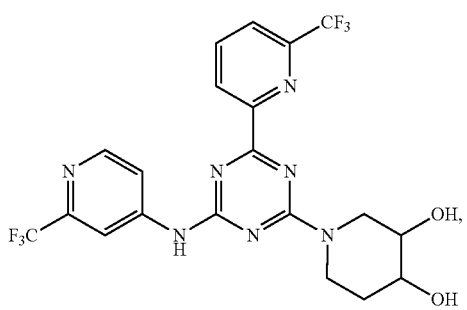
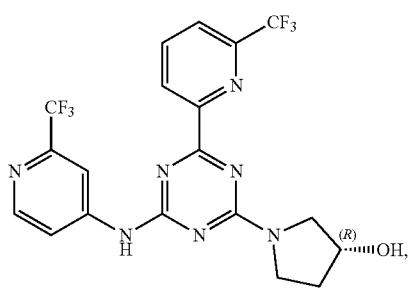
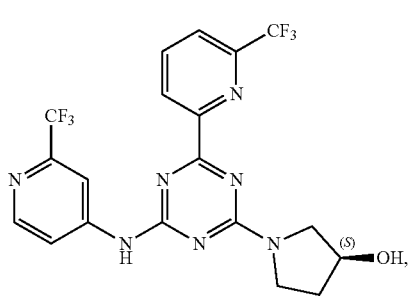
-continued
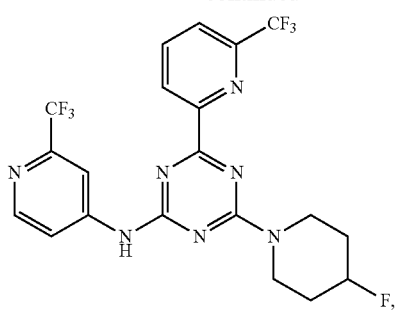
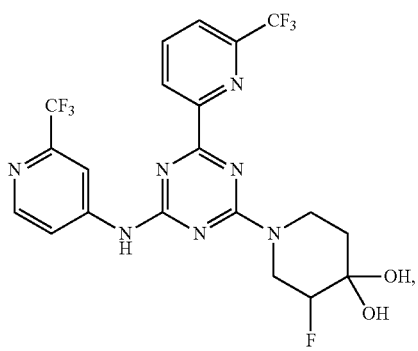
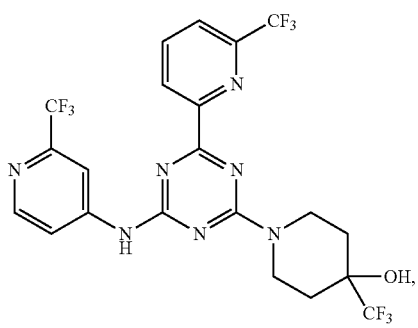
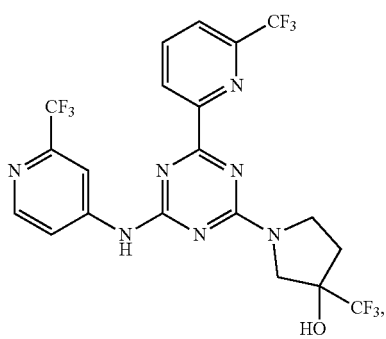
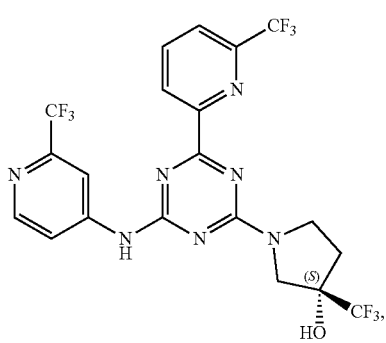

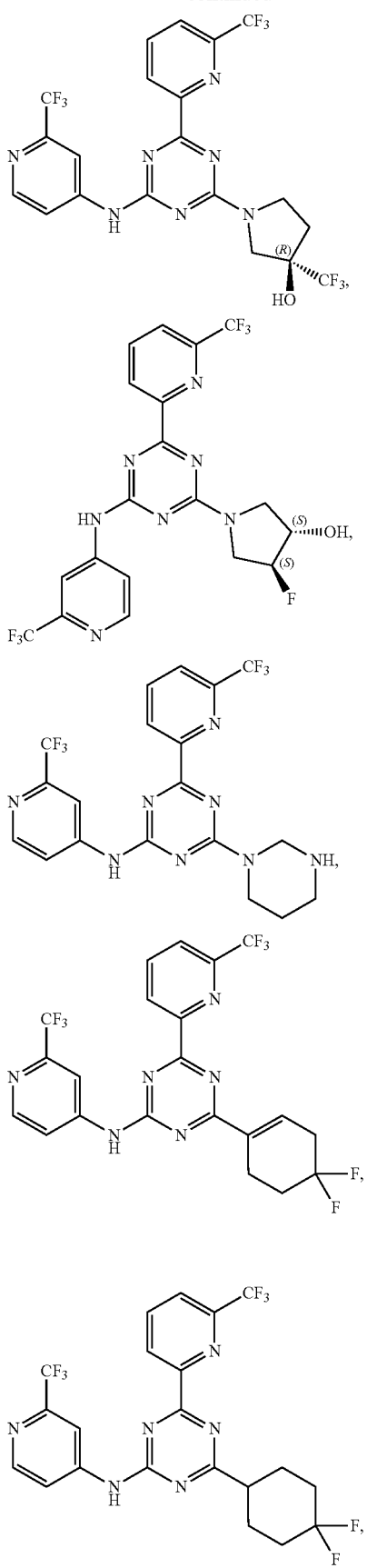
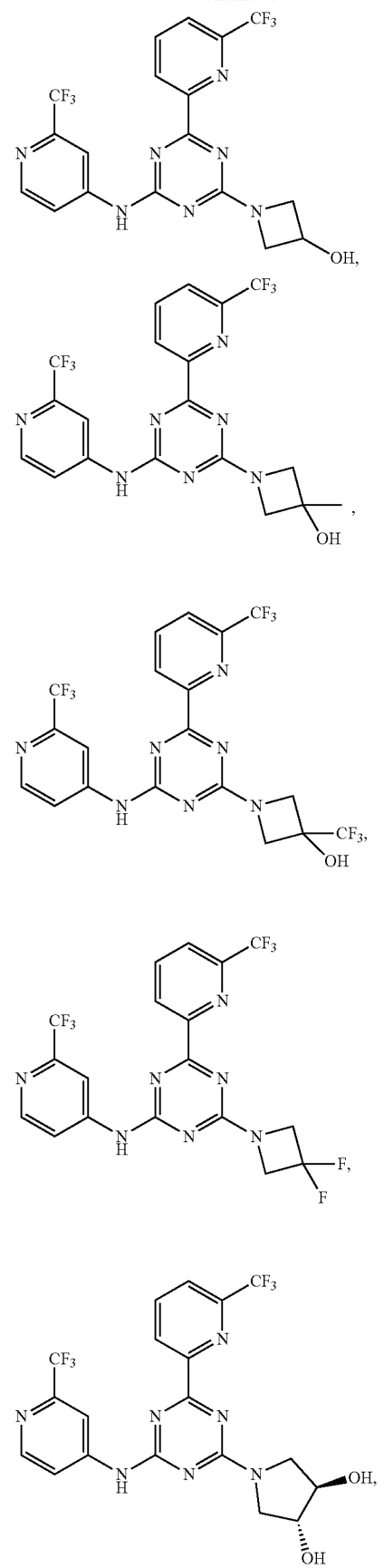

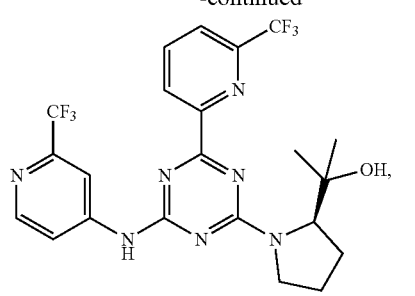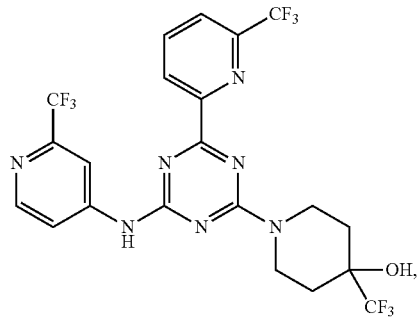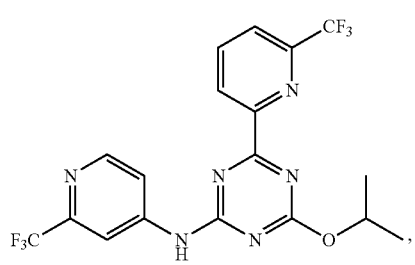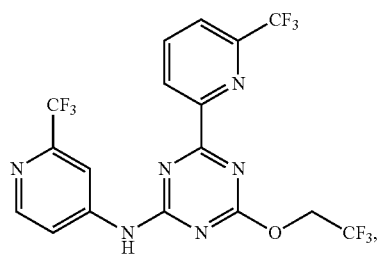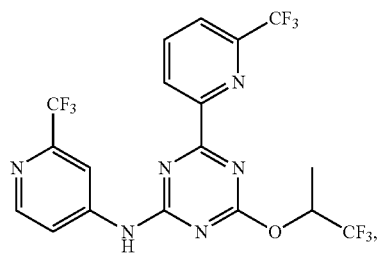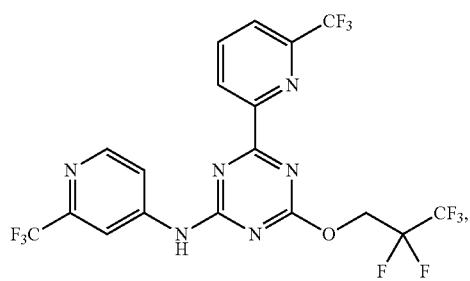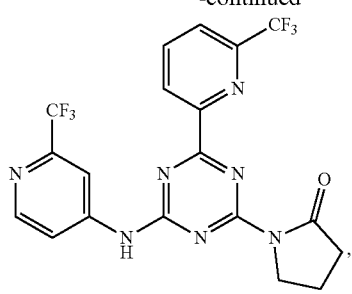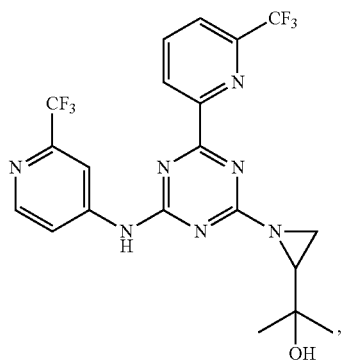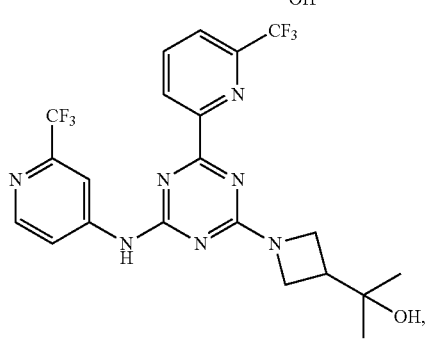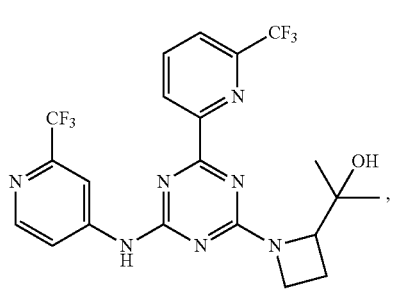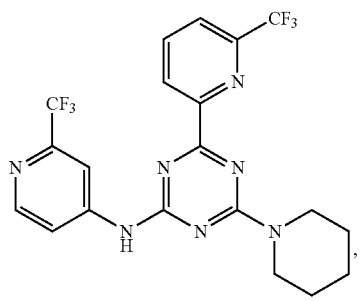

-continued

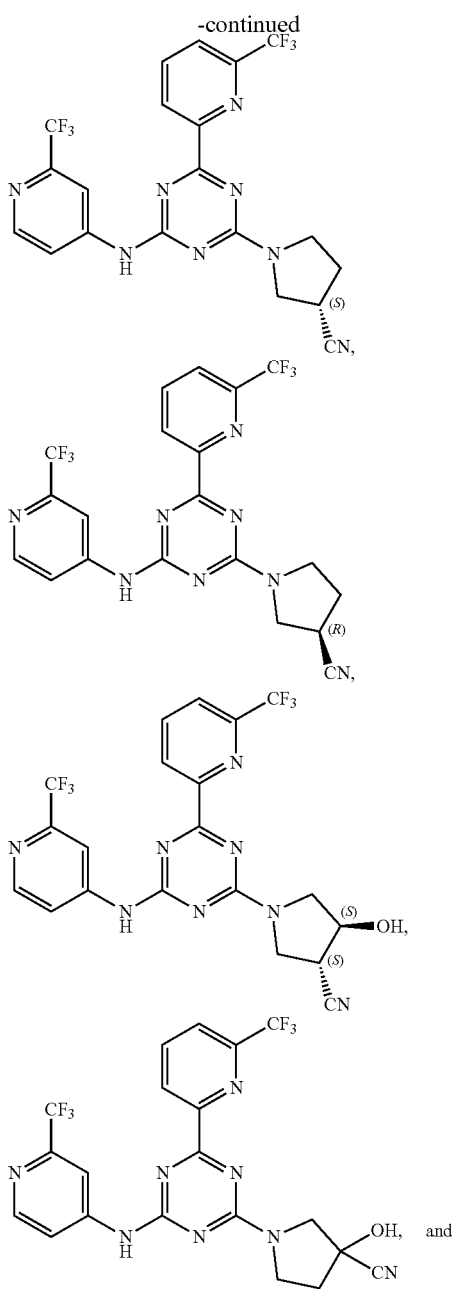

-continued

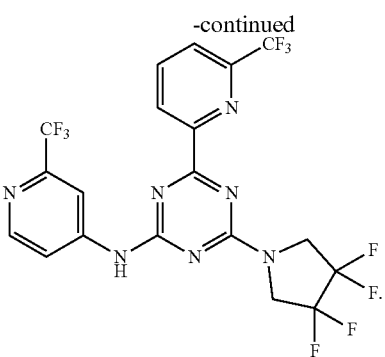

8. A pharmaceutical composition, comprising the compound or the pharmaceutically acceptable salt, crystal, solvate or prodrug thereof according to claim 1, and a pharmaceutically acceptable carrier.

9. A method for treating cancer characterized by the presence of mutant IDH2 in a subject in need thereof comprising administering to the subject a therapeutically effective amount of the compound or the pharmaceutically acceptable salt, crystal, solvate or prodrug thereof according to claim 1, wherein the cancer is selected from the group consisting of glioblastoma, myelodysplastic syndrome, myeloid proliferative neoplasm, acute myeloid leukemia, sarcoma, melanoma, non-small cell lung cancer, chondrosarcoma, cholangiocarcinoma and angioimmunoblastic lymphoma.

10. A method for treating cancer characterized by the presence of mutant IDH2 in a subject in need thereof comprising administering to the subject a therapeutically effective amount of the compound or the pharmaceutically acceptable salt, crystal, solvate or prodrug thereof according to claim 7, wherein the cancer is selected from the group consisting of glioblastoma, myelodysplastic syndrome, myeloid proliferative neoplasm, acute myeloid leukemia, sarcoma, melanoma, non-small cell lung cancer, chondrosarcoma, cholangiocarcinoma and angioimmunoblastic lymphoma.

* * * * *

UNITED STATES PATENT AND TRADEMARK OFFICE
CERTIFICATE OF CORRECTION

PATENT NO. : 10,961,222 B2
APPLICATION NO. : 16/312666
DATED : March 30, 2021
INVENTOR(S) : Yong Wang et al.

Page 1 of 2

It is certified that error appears in the above-identified patent and that said Letters Patent is hereby corrected as shown below:

On the Title Page

Item (73) Assignee, delete "NANJING SANHOME PHARMACEUTICAL CO., LTD., Jiangsu, (CN)" and replace with --NANJING SANHOME PHARMACEUTICAL CO., LTD., Nanjing, Jiangsu, (CN)-- therefor.

In the Claims

In Claim 7, Column 87, Lines 15-27, delete the entire contents and insert

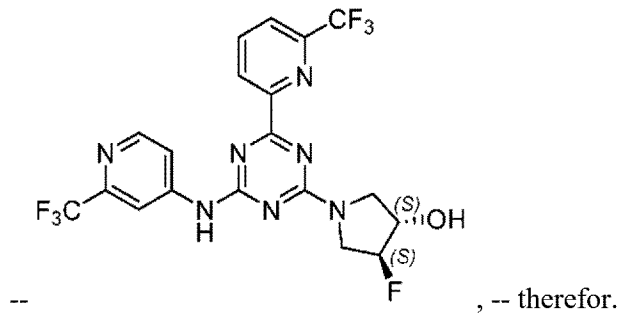

-- , -- therefor.

In Claim 7, Column 89, Lines 25-35, delete the entire contents and insert

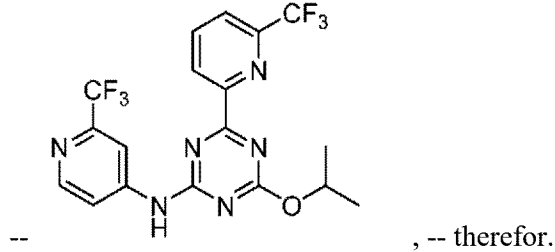

-- , -- therefor.

Signed and Sealed this
First Day of June, 2021

Drew Hirshfeld
*Performing the Functions and Duties of the
Under Secretary of Commerce for Intellectual Property and
Director of the United States Patent and Trademark Office*

In Claim 7, Column 89, Lines 56-65, delete the entire contents and insert
-- 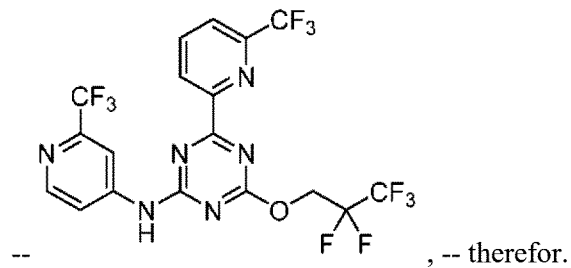 , -- therefor.